US011998742B1

(12) United States Patent
Choi et al.

(10) Patent No.: US 11,998,742 B1
(45) Date of Patent: Jun. 4, 2024

(54) ANTIVIRAL DIGITAL DEVICE

(71) Applicant: S-Alpha Therapeutics, Inc., Seoul (KR)

(72) Inventors: Seung Eun Choi, Seoul (KR); Yong Sun Lee, Princeton, NJ (US); Ja Rang Hahm, Seoul (KR)

(*) Notice: Subject to any disclaimer, the term of this patent is extended or adjusted under 35 U.S.C. 154(b) by 0 days.

(21) Appl. No.: 18/234,456

(22) Filed: Aug. 16, 2023

Related U.S. Application Data

(63) Continuation of application No. 17/512,579, filed on Oct. 27, 2021, which is a continuation-in-part of application No. PCT/KR2021/005448, filed on Apr. 29, 2021.

(60) Provisional application No. 63/051,358, filed on Jul. 13, 2020, provisional application No. 63/017,413, filed on Apr. 29, 2020.

(51) Int. Cl.
*A61N 1/36* (2006.01)
*A61B 5/00* (2006.01)

(52) U.S. Cl.
CPC .......... *A61N 1/3606* (2013.01); *A61B 5/4833* (2013.01); *A61N 1/36053* (2013.01)

(58) Field of Classification Search
CPC . A61N 1/3606; A61N 1/36053; A61B 5/4833
See application file for complete search history.

(56) References Cited

U.S. PATENT DOCUMENTS

| | | | |
|---|---|---|---|
| 2008/0242954 A1 | 10/2008 | Naya et al. | |
| 2009/0024187 A1* | 1/2009 | Erickson | A61N 1/37247 607/59 |
| 2010/0114195 A1 | 5/2010 | Burnes et al. | |
| 2010/0292600 A1 | 11/2010 | Dibenedetto et al. | |
| 2012/0330373 A1 | 12/2012 | Ternes et al. | |
| 2013/0193351 A1 | 8/2013 | Cheng et al. | |
| 2013/0245486 A1 | 9/2013 | Simon et al. | |
| 2014/0142654 A1 | 5/2014 | Simon et al. | |
| 2014/0172442 A1 | 6/2014 | Broderick et al. | |
| 2014/0214135 A1 | 7/2014 | Ben-David et al. | |
| 2015/0012284 A1 | 1/2015 | Schenk et al. | |
| 2016/0220868 A1 | 8/2016 | Noorzai et al. | |
| 2016/0234595 A1 | 8/2016 | Goran et al. | |
| 2016/0339300 A1 | 11/2016 | Todasco | |
| 2016/0365006 A1 | 12/2016 | Minturn | |
| 2016/0378608 A1 | 12/2016 | Kong et al. | |
| 2017/0128356 A1 | 5/2017 | Lin et al. | |

(Continued)

FOREIGN PATENT DOCUMENTS

| | | |
|---|---|---|
| JP | 2013-31665 A | 2/2013 |
| JP | 2017-162442 A | 9/2017 |

(Continued)

OTHER PUBLICATIONS

International Search Report and Written Opinion issued in corresponding International Patent Application No. PCT/KR2021/005448 dated Aug. 13, 2021.

(Continued)

*Primary Examiner* — Amanda K Hulbert
*Assistant Examiner* — Philip C Edwards
(74) *Attorney, Agent, or Firm* — Morgan, Lewis & Bockius LLP

(57) ABSTRACT

The present disclosure provides systems and methods for treating a virus disease in a subject in need thereof.

21 Claims, 68 Drawing Sheets

(56) References Cited

U.S. PATENT DOCUMENTS

| | | | |
|---|---|---|---|
| 2017/0188976 A1 | 7/2017 | Kalra et al. | |
| 2017/0112390 A1 | 8/2017 | Cho et al. | |
| 2017/0228229 A1 | 8/2017 | Jain et al. | |
| 2017/0286622 A1 | 10/2017 | Cox et al. | |
| 2018/0001184 A1* | 1/2018 | Tran | G16H 50/20 |
| 2019/0001135 A1* | 1/2019 | Yoo | A61N 1/36132 |
| 2019/0321633 A1 | 10/2019 | Simon et al. | |
| 2020/0335191 A1 | 10/2020 | Brown et al. | |
| 2022/0115108 A1* | 4/2022 | Choi | G16H 20/70 |

FOREIGN PATENT DOCUMENTS

| | | |
|---|---|---|
| KR | 10-2002-0035030 A | 5/2002 |
| KR | 10-2020-0042372 A | 4/2020 |
| WO | 2015/179744 A | 11/2015 |

OTHER PUBLICATIONS

Be Well Bodyworks, Should you exercise after a massage? http://bewellbody.com/should-you-exercise-after-a-massage/ (last visited Oct. 20, 2022) (2016).

International Search Report and Written Opinion issued in related International Patent Application No. PCT/KR2022/016607 dated Feb. 7, 2023.

\* cited by examiner

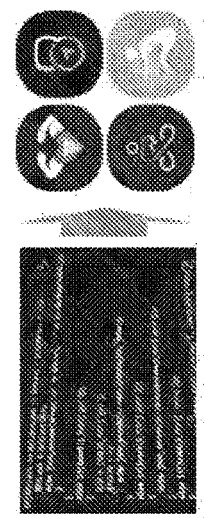
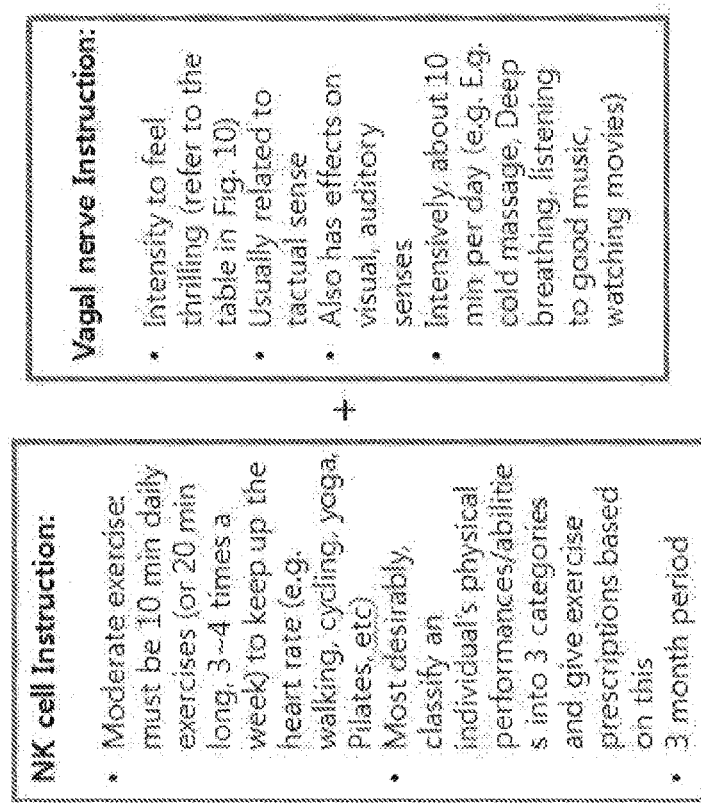
FIG. 9

| Visual | Auditory | Tactual (sense of pressure) | Gustatory | Olfactory | Etc. |
|---|---|---|---|---|---|
| • Erotic photos<br>• Cold photos (shrink sweat glands)<br>• Very hot photos (open sweat glands)<br>• Frightening photos | • Frightening sounds(chill, changes in skin)<br>• Raindrop sounds(relaxes, makes fall asleep) | • Deep breathing-stimulates diaphragm<br>• Breathing itself, short of breath<br>• Heart rate increases<br>• Movements in GI tract (until T colon)<br>• Stop breathing for 20–60sec*<br>• Suddenly bathing the face in cold water*<br>• Coughing*<br>• Massage, soft skin touch | • Delicious food (stimulates digestive glands inside the organs) | • Delicious smell (stimulates ANS to secrete saliva, etc. from the digestive glands inside the organs)<br>• Comfortable smell (relaxing, decreases the heart rate) | • When GI's EECell has alpha-synuclein, this goes to the cerebellum via vagal nerve to trigger PD |

*vagal maneuver

FIG. 11

| Acute exercise | Aerobic exercise | Anaerobic exercise |
|---|---|---|
| A single bout of exercise, 1-2 times per week | aerobic physical training (APT)<br>• Indoor: elliptical trainer, indoor rower, stationary bicycle, treadmill<br>• Outdoor: walking, cycling, running, cross-country skiing, cross-country running, Nordic walking, inline skating, skateboarding, rowing<br>• Indoor or outdoor: swimming, kickboxing, skipping rope or jump rope, circuit training, jumping jacks, water aerobics, jogging | short in duration (less than 60 seconds), no oxygen burden<br>• weight lifting<br>• running 100 meters<br>• climbing a flight of stairs |

ANTIVIRAL DIGITAL DEVICE

CROSS-REFERENCE TO RELATED APPLICATION

This application is a continuation of U.S. patent application Ser. No. 17/512,579 filed on Oct. 27, 2021, which is a continuation-in-part of International Application No. PCT/KR2021/005448 filed on Apr. 29, 2021, which claims the priorities to U.S. Patent Application No. 63/017,413, filed Apr. 29, 2020, and U.S. Patent Application No. 63/051,358, filed Jul. 13, 2020, the disclosures of which are incorporated herein by reference in their entireties.

BACKGROUND

Vaccination is a process of preemptively attaining immunity against the particular antigen by injecting dead or weakened antigen that causes the disease, or vaccine, into a human body. The vaccination has been successfully utilized in overcoming the diseases that have long troubled human (e.g., smallpox, polio, measles, etc.). However, there are cases where the vaccination cannot be employed. A good example of this is a new viral disease. A viral disease that is originated from animals may spread to humans and undergo mutation to cause a new viral disease. A highly virulent new viral disease spreads rapidly, shows severe symptoms, and is not treated easily. Furthermore, it can pose a new challenge to humans in terms of disease management in that it is not easily prevented or treated with the existing vaccines or the existing anti-virus drugs. At the status quo, there are no other practical prevention methods than individuals' paying particular attention to personal sanitation such as hand hygiene, wearing masks, practicing social distancing, self-quarantine, etc. However, when it exceeds a certain level of infected population and pandemic begins, the current method loses its efficacy. Excluding the current personal sanitation management and the passive prevention measures, there are no active prevention methods to manage the outbreak of the new viral disease. In addition, it usually takes 5-10 years to develop a safe and effective vaccine, costing more than $1.5 billion, and further, if pathogens cause mutation, the immune function by the vaccine may not work. Therefore, it is important to manage the individual's immune system to prepare for new and variant viruses in situations where it is difficult to rely solely on vaccines.

As a result of various studies on exercise and immune response in the body, it has been reported that NK cells, which kill cells infected with viruses or the like with the innate immune system, are regulated by medium-intensity exercise. Moderate exercise can lower the risk of infections such as URTIs, low-intensity exercise is ineffective, and excessive exercise can increase the likelihood of inflammation (see the graph below). Regular exercise increased anti-inflammatory cytokines such as Interleukin-10 (IL-10) and Regulatory T cells, and both long-term and short-term exercise improved innate and acquired immune responses by vaccination.

In addition to medium-intensity exercise, there are activities that stimulate the vagus nerve to strengthen the immune system. The vagus nerve is the tenth cranial nerve and is an important component of the parasympathetic branch of the autonomic nervous system that controls the unconscious movements of the heart, lungs, adrenal glands, and digestive tract. It is the most complexly distributed nerve among the cranial nerves, and unlike other cranial nerves, it extends throughout the body and has a wide distribution. Recent studies show that the vagus nerve can regulate cytokine production through the efferent arm, which uses neuroimmune communication called the 'Cholinergic anti-inflammatory pathway' of the vagus nerve. There is a review that this function of the vagus nerve is applied to rheumatoid arthritis (RA), one of chronic inflammatory autoimmune diseases, and plays a role in regulating RA. The vagus nerve can be stimulated by actions without using electrical signals, such as deep breathing. Deep breathing is an activity that is commonly included in many meditation techniques. Through deep breathing, the vagus nerve is stimulated and the parasympathetic nervous system is affected, so that through meditation, you can get a positive effect on physical and mental health.

Accordingly, one objective of the present disclosure is to help maintaining and managing health by inducing immune system reinforcement. As one aspect, the present disclosure provides a system and a method of enabling communication between patients and doctors in the form of mobile application in providing appropriate exercise and activities that stimulate the vagus nerve to strengthen the immune system of the patients. The patients can record activities which can be accessed and reviewed by the doctors through the web portal site in such a noninvasive and untact manner. As another aspect, the system enables the application to be used only when a doctor prescribes to a patient for specific needs.

BRIEF DESCRIPTION OF THE DRAWINGS

The above and other objects, features and advantages of the present disclosure will become more apparent to those of ordinary skill in the art by describing in detail exemplary embodiments thereof with reference to the attached drawings, in which:

FIG. 9 illustrates an example of ADD application;

FIG. 11 illustrates exemplary stimulation for Vagal nerve innervation;

FIG. 12 illustrates exemplary exercises suitable for T cells;

Figure 1:
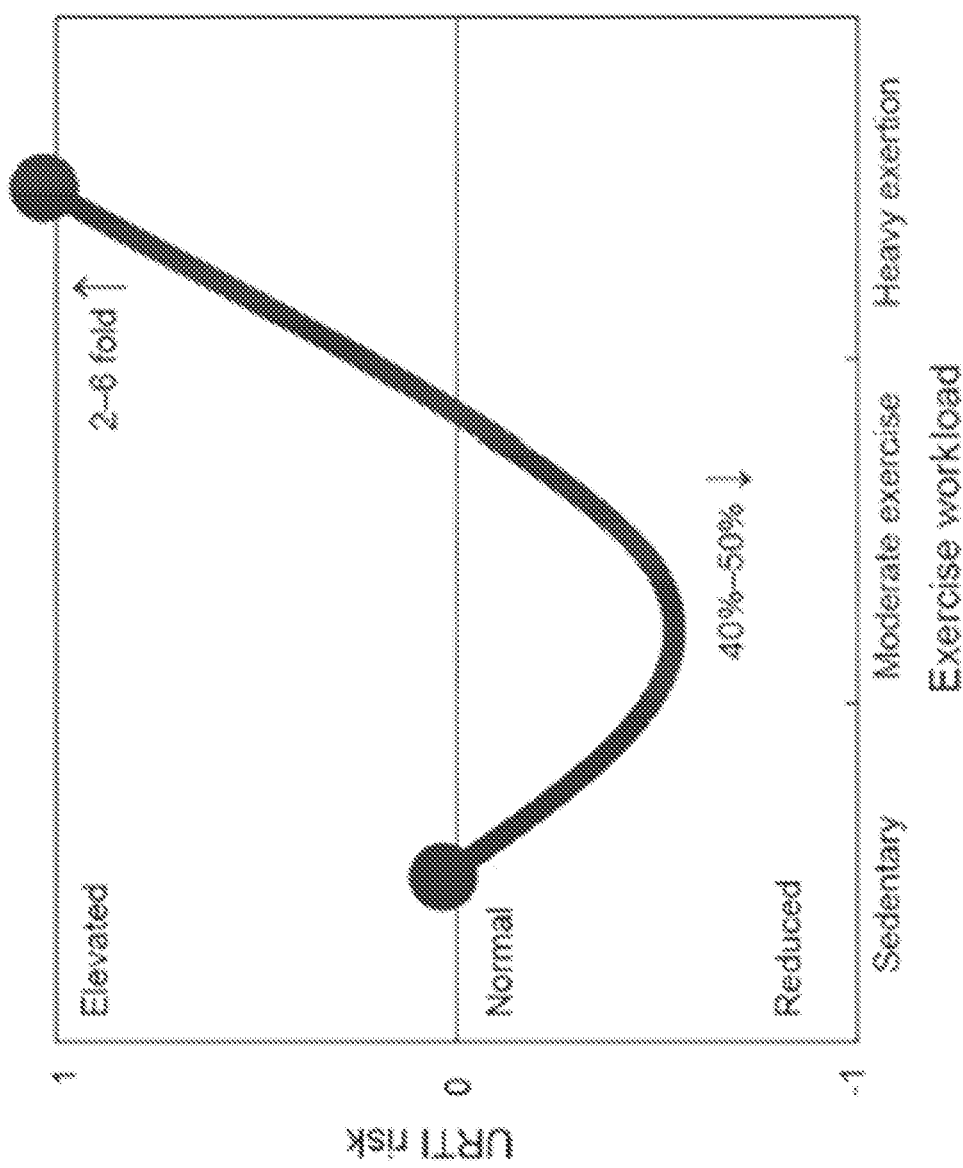
FIG. 1 shows a graph illustrating a relationship between exercise and upper respiratory tract infection (URTI)

While the above-identified drawings set forth presently disclosed embodiments, other embodiments are also contemplated, as noted in the discussion. This disclosure presents illustrative embodiments by way of representation and not limitation. Numerous other modifications and embodiments may be devised by those skilled in the art which fall within the scope and spirit of the principles of the presently disclosed embodiments.

DETAILED DESCRIPTION

Hereinafter, exemplary embodiments of the present disclosure will be described in detail. However, the present disclosure is not limited to the embodiments disclosed below, but may be implemented in various forms. The following embodiments are described in order to enable those of ordinary skill in the art to embody and practice embodiments of the present disclosure.

Definitions

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

The terminology used herein is for the purpose of describing particular embodiments only and is not intended to be limiting of exemplary embodiments. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof.

As used herein, the term "about" generally refers to a particular numeric value that is within an acceptable error range as determined by one of ordinary skill in the art, which will depend in part on how the numeric value is measured or determined, i.e., the limitations of the measurement system. For example, "about" may mean a range of +20%, +10%, or +5% of a given numeric value.

As used herein, the term "antiviral digital device application" generally refers to a health service which can help a subject or group of subjects to maintain, optimize, and/or strengthen their physical condition at its best by encouraging and suggesting appropriate exercises and vagal or vagus nerve stimulation (VNS). In some embodiments, the exercise may include moderate exercise, aerobic exercise, and/or acute exercise. In certain embodiments, the antiviral digital device application can record daily conditions of the patient, provide moderate and benchmark exercise schedule (e.g., 2~3 times a week), keep track of the heart rate (HR) with a wearable device while the patient performs exercise (e.g., moderate exercise), provide the target HR for exercises (e.g., moderate exercise), provide activity guidance such as taking a deep breath or listening to white noise in order to stimulate the vagal nerve, provide push alarms to make the patient continuously use the application.

As used herein, the term "maintaining, optimizing, or strengthening an immune system" means an improvement of a subject's immune system compared to a control subject not exposed to the method, device or system described herein. In some embodiments, the "maintaining" an immune system may be for a subject expected to have a decreasing immune system, for example, with an immune disease. The improvement may be verified based on the amounts of NK cells, CD4+ T cells, CD8+ T cells, B cell, pro-inflammatory cytokines (IL-6, TNF-a and IL-1b), anti-inflammatory cytokine (IL-10), and/or IFN-γ, whether antibodies are produced after vaccination against influenza, and/or expression and severity of upper respiratory tract infection symptoms as shown in the examples described herein.

As used herein, the term "moderate exercise" generally refers to performing exercise (e.g., aerobic exercises) at a moderate level (e.g., power walking), such that a target heart rate is maintained.

As used herein, the term "benchmark exercise" generally refers to performing the same type of exercise during a given time to determine a baseline level of fitness for adjusting the target heart rate (e.g., to correspond to moderate exercise). In some embodiments, a benchmark exercise can be performed by the subject at regular intervals (e.g., every 1 to 2 weeks).

As used herein, an exercise is considered "completed" if the subject performs an exercise for more than a predetermined period of time (e.g., 5 minutes). If the subject performs an exercise for less than the predetermined period of time, the data may not be saved, and the exercise is not considered to be completed.

As used herein, the term "target heart rate" generally refers to a heart rate or range of heart rates that correspond to a particular level of exercise (e.g. moderate exercise) considering the subject's age. Table 1 below shows the initial correspondence between age and target heart rate to achieve low, moderate, or vigorous exercise. Check for moderate heart rate range and refer to Table 1 on the right considering the patient's age when giving prescriptions. Each age group has a moderate heart rate range with different minimum and maximum value. The age group # refers to the oldest age of the given age group. For example, a subject older than 15 yet 20 or younger falls into the 20 age group. The average of the two values can be used as the first target heart rate. For example, in case of a 21-year-old subject that belongs to the 25 age group, the subject's moderate heart rate range becomes 122~145. The average of the two values is 133.5, so the first target heart rate can be 134 after rounding. Low intensity is determined as less than 64% of max HR. Moderate intensity is determined as 64~76% of max HR. Vigorous intensity is determined as more than 76% of max HR

TABLE 1

Target heart rate range depending on age and exercise intensity

| Age | Low | Moderate | Vigorous | Maximum HR |
|---|---|---|---|---|
| 15 | <126 | 126-150 | >150 | 197 |
| 20 | <124 | 124-147 | >147 | 194 |
| 25 | <122 | 122-145 | >145 | 190 |
| 30 | <120 | 120-142 | >142 | 187 |
| 35 | <117 | 117-139 | >139 | 183 |
| 40 | <115 | 115-137 | >137 | 180 |
| 45 | <113 | 113-134 | >134 | 177 |
| 50 | <111 | 111-132 | >132 | 173 |
| 55 | <109 | 109-129 | >129 | 170 |
| 60 | <107 | 107-127 | >127 | 167 |
| 65 | <105 | 105-124 | >124 | 163 |
| 70 | <102 | 102-122 | >122 | 160 |
| 75 | <100 | 100-119 | >119 | 157 |
| 80 | <98 | 98-117 | >117 | 153 |
| 85 | <96 | 96-114 | >114 | 150 |
| 95 | <92 | 92-109 | >109 | 143 |

As used herein, the term "vagal nerve stimulation" generally refers to one or more activities capable of stimulation the vagal nerve, including, for example, deep breathing, holding a subject's breath, listening to white noise, aroma meditation, bathing a subject's face in cold water, and/or experiencing fear. In certain embodiments, a single VNS module can last for 5 min. In certain embodiments, a subject needs to perform more than 10 min of VNS practice. Hence, the subject can have two different VNS modules (e.g., performing two sessions each lasting for 5 min). In certain embodiments, the first VNS module of the day is fixed as deep breathing. In certain embodiments, the two sets of VNS practice must be performed in consecutive order. If a patient stops while performing the second set of activity, the record of both the second set and the first set of activity may be deleted. In certain embodiments, performing the same set of VNS activities is not available (e.g., a subject cannot choose deep breathing for the second set of activities).

Overview

With reference to the appended drawings, exemplary embodiments of the present disclosure will be described in detail below. To aid in understanding the present disclosure, like numbers refer to like elements throughout the description of the figures, and the description of the same elements will be not reiterated.

The present disclosure relates to digital therapeutics (hereinafter referred to as DTx) intended for maintaining, optimizing, or strengthening an immune system of a subject. The present disclosure also relates to systems that integrate digital therapeutics with one or both of a healthcare provider portal and an administrative portal to maintain, optimize, or strengthen an immune system of a subject. Some embodiments of the present disclosure may comprise deducing a mechanism of action (hereinafter referred to as MOA) in immune health (e.g., immunity against an antigen or pathogen), and establishing a therapeutic hypothesis and a digital therapeutic hypothesis for maintaining, optimizing, or strengthening an immune system of a subject.

In some embodiments, the method described herein activates or increases production of natural killer (NK) cells in the subject. In some embodiments, the method reduces a change in a number of central T cells in the subject. In some embodiments, the method reduces a change in a number of effector T cells in the subject. In some embodiments, the method reduces a change in a number of effector memory T cells in the subject. In some embodiments, the method activates or increases production of naïve CD4 T cells in the subject. In some embodiments, the naïve T cells are activated or increased within one month from the providing. In some embodiments, the method reduces a change in a number of central CD4 T cells in the subject. In some embodiments, the method reduces a change in a number of effector CD4 T cells in the subject. In some embodiments, the method reduces a change in a number of effector memory CD4 T cells in the subject. In some embodiments, the method reduces a change in a number of naïve CD8 T cells in the subject. In some embodiments, the method reduces a change in a number of central CD8 T cells in the subject. In some embodiments, the method reduces a change in a number of effector CD8 T cells in the subject. In some embodiments, the method reduces a change in a number of effector memory CD8 T cells in the subject. In some embodiments, the method activates or increases production of CD4 Treg cells in the subject. In some embodiments, the method activates naïve B cells into maturation in the subject. In some embodiments, the method increases naïve B cells in the subject. In some embodiments, the method increases memory B cells in the subject. In some embodiments, the method decreases plasma B cells in the subject.

Furthermore, methods and apparatuses are described herein for active prevention of a virus outbreak and antiviral digital immunity (ADI). For example, a digital therapeutic module that comprises one or more digital instructions may be generated. The one or more digital instructions may cause a user's immune system at least one of natural killer (NK) cell recruitment via moderate exercise, T cell boosting, and B cell maturation and IgA secretion. The digital instructions related to the NK cell recruitment may comprise moderate exercise when we categorize the exercise as vigorous exercise, moderate exercise and light exercise. The instructions related to the T cell boosting may comprise aerobic exercise and/or acute exercise. The instructions related to the B cell maturation and IgA secretion may comprise instructions for VNS comprising at least one of visual, auditory, tactual, gustatory, and olfactory stimulations that increase sIgA secretion. The one or more digital instructions may be provided to a user via the user device.

Some embodiments disclosed herein relate to antiviral digital device (ADD) for active prevention of a virus outbreak and antiviral digital immunity (ADI) through ADD. For example, a mechanism of action (MOA) of antivirus of a host's immune system may be deduced through literature search and expert reviews of basic scientific articles and related clinical trial articles concerning anti-viral immunity. A digital apparatus and/or an application may deliver the instructions intensifying the host's (simultaneously the user of the application) immune system with the digital application based on the MOA, collect the practice data of the user on the present instructions, and feedback the results of the instruction-practice sets.

ADI hereinafter may refer to antiviral digital immunity by one or more digital instructions used to stimulate the production of antibodies and provide innate and adaptive immunity against one or several viruses. The digital instructions may be prepared from the behavioral/environmental codes which have mode of action based on innate and adaptive immune system change, treated to act as an adjunct of antigenic activity without inducing the disease.

The vaccination so far has been a process of preemptively attaining immunity against the particular antigen by injecting dead or weakened antigen that causes the disease, or vaccine, into a human body. The vaccination has been successfully utilized in overcoming the diseases that have long troubled human (e.g., smallpox, polio, measles, etc.)

However, there are cases where the vaccination cannot be employed, an important axis of human's resisting against disease. A good example of this is a new viral disease. A viral disease originally from animals may spread to humans and undergo mutation to cause a new viral disease. A highly virulent new viral disease spreads rapidly, shows severe symptoms, and is not treated easily. In addition to these, it poses a new challenge to humans in terms of disease management in that it is not easily prevented or treated with the existing vaccines or the existing anti-virus drugs.

Particularly, because of rising risks of animal to human infection, due to destruction of animal habitats along with population increase, the activation of defrosted viruses as a result of permafrost's melting due to climate change, and intensified globalization which facilitates global pandemic, new viral diseases are predicted to constantly trouble humans in the future as well. In fact, the outbreak of infectious diseases (e.g., SARS, MERS, COVID-19) from the new mutated virus, coronavirus, is not only a problem in a particular region but to the entire global community, resulting in enormous medical, social and financial losses.

Unfortunately, however, the current vaccine technology cannot mass-produce vaccines against the rapidly spreading new viral disease.

At the status quo, there are no other practical prevention methods than individuals' paying particular attention to personal sanitation such as hand hygiene, wearing masks, practicing social distancing, etc.

As a response to the new viral disease outbreak, keeping infectees in quarantine and recommending self-quarantine to contacts are carried at early infection period, when community infection is not starting yet, based on epidemiological survey. However, the current method loses its efficacy when it exceeds a certain level and pandemic begins.

Excluding the current personal sanitation management and the passive prevention measures, there are no active prevention methods to manage the outbreak of the new viral disease. Particularly, for healthcare professionals (HCPs) or caregivers of patients who are continuously exposed to the source of infection, effective prevention and management means are urgently needed.

For all times and places, the notion of boosting immunity or providing immunity to prevent diseases have universally existed. In particular, there is a long history of folk remedies such the intake of particular food (e.g., red ginseng) or practicing particular exercise (e.g., yoga). However, in the perspective of modern science, there are no sufficient clinical grounds that support the medical efficacy of the aforementioned foods or exercises.

Digital therapeutics aims to improve or treat a patient's disease by providing digital instructions to the patient via the doctor's prescription on the application, monitoring the patient's practice on the instructions regularly, and collecting the patient's instruction-practice data. At the status quo, active research and development on digital therapeutics are being proceeded.

Figure 2:
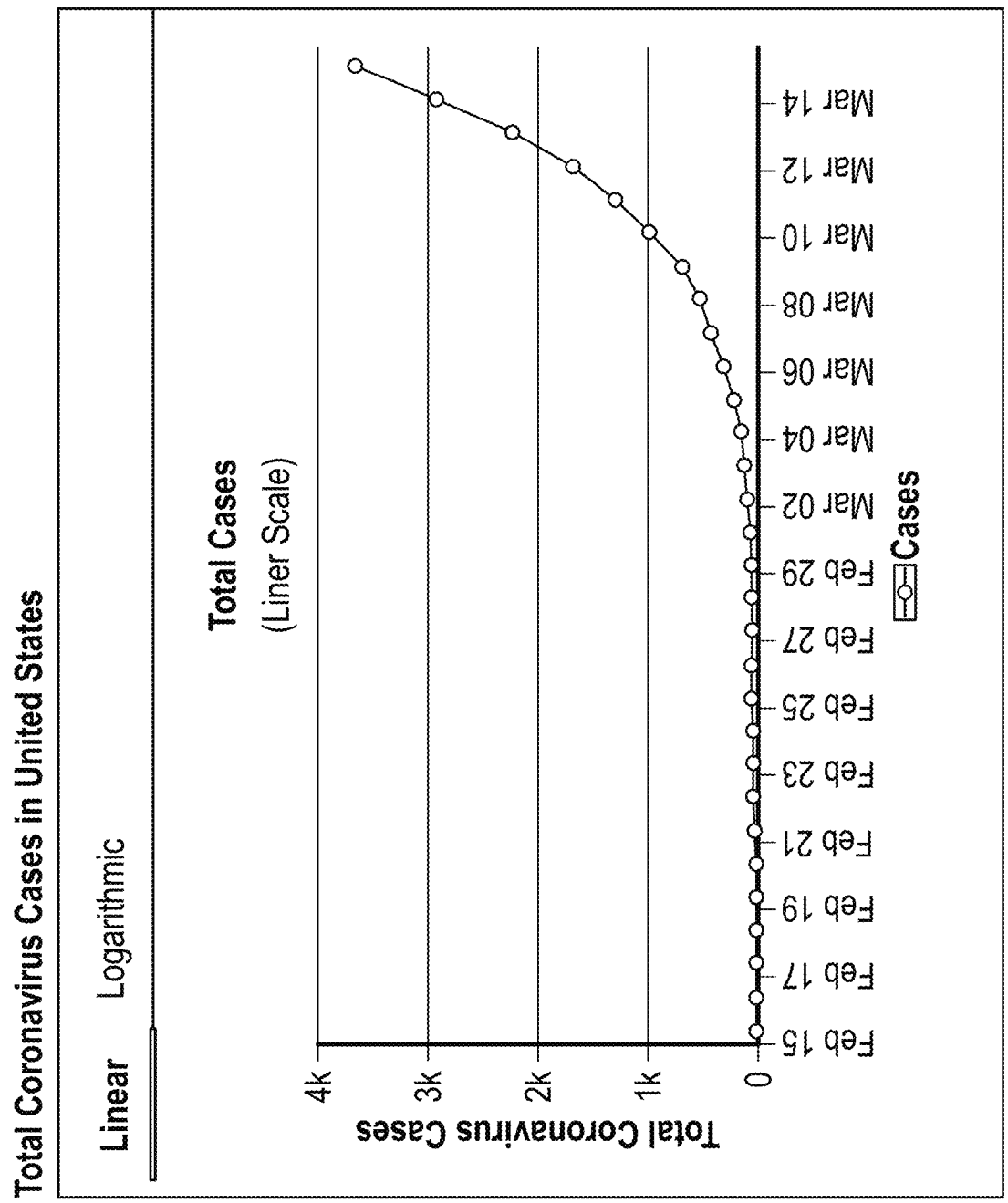
FIG. 2 illustrates an example of exponential growth, epidemics of a virus, and a golden time for antiviral defense.

FIG. 2 is a diagram illustrating an example exponential growth and epidemics of virus and a golden time for antiviral defense. The graph in FIG. 2 illustrates the increase of the number of the total COVID-19 cases in the U.S. So far the management of new viral diseases of which the vaccine had not been developed has based on passive prevention, that is, preventing the physical contact between the new virus and host. Examples of passive prevention include wearing masks and practicing hand hygiene at the personal level, and practicing social distancing.

As can be seen from FIG. 2, there is some degree of time gap between the period when the dangerousness of the new virus was alerted to the society (▼) and the period when the number of confirmed cases increases drastically (▽). Particularly, if active prevention, which enhances the body's immunity to react, is practiced during this time period, the spread of the new viral disease can be more effectively controlled.

Figure 3:
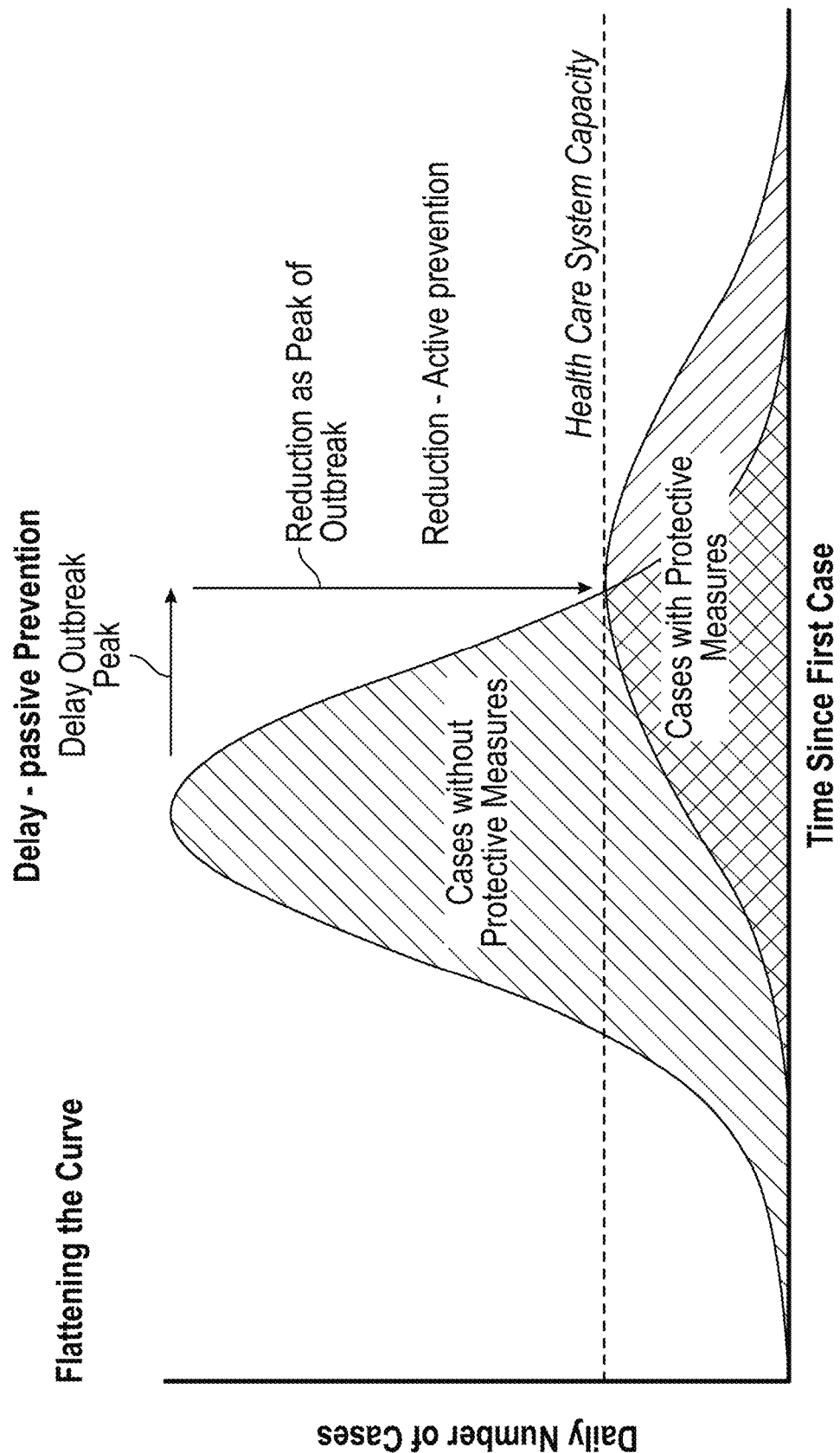
FIG. 3 illustrates an exemplary delayed outbreak peak, and reduction in peaks of outbreak to control the virus disease within health care system capacity.

FIG. 3. is a diagram illustrating an example delay outbreak peak and reduction in peaks of outbreak to control the virus disease within health care system capacity. In FIG. 3, the macroscopic disease management strategy is shown in cases of a virus outbreak. The "Delay outbreak peak" strategy reduces the speed of which the epidemic spreads, and thereby gives time to strengthen the response capacity of the health care systems to prepare for a severe epidemic. Also, the "Reduction in peaks of outbreak" strategy alleviates the increase of confirmed cases to help manage the epidemic within the response capacity of the health care system. For the management of new viral diseases, active prevention is necessary which bases on the "Reduction in peaks of outbreak" strategy along with the passive prevention based on the established "Delay outbreak peak" strategy. However, in cases of new viral diseases of which the vaccine has not been developed, the discussion on individuals' providing immunity for effective active prevention is at an elementary level.

Embodiments disclosed herein may include measures to reduce the prevalence of the virus without the spatiotemporal limits and financial burden in a virus outbreak situation (ADI) in the digital device application (ADD).

Viral infection shows host dependence. This host dependence can firstly be explained in terms of innate immunity which results from the host's genetic factors, and acquired immunity which is attained from the host's prior experience with similar viruses. An infected subject with acquired immunity tends not to show any particular symptoms or to only show mild symptoms, and overcome the viral infection.

Realistically approaching, as the vaccine against the present new viral disease has not been developed in the new virus disease outbreak situation, the vaccination strategy involving the acquired immunity is not valid.

Host dependence against viruses cannot be explained with the sole factor of the aforementioned innate and acquired immunity. In fact, in case of highly contagious coronavirus which is infected through upper respiratory tract mucosa, the elderly are particularly vulnerable. The epidemiological fact may imply that the host's overall immune system involving particular organs (spleen, bone marrow, and thymus), lymphocytes (B-cells, T-cells and natural killer cells) and antibody, along with particular mechanisms such as the aforementioned innate and acquired immunity, is important in understanding the new viral disease outbreak.

The immune system of the throat and upper respiratory tract, where the coronavirus first comes in contact, is called mucosal immunity. Mucosal monocyte, polymorphonuclear leukocyte (PMN), macrophage and natural killer (NK) cells practice primary defense against the virus. However, if the host's immune system fails to practice the defense (host factor) or the virus avoids mucosal immune system, the infection of the virus may extend to further areas such as pulmonary alveoli.

If the host's immune system is broken down, the infection of the new coronavirus may result in severe symptoms such as pneumonia. However, if the host's immune system is strong, the host may experience little or no symptoms at all.

The MOA of antivirus of a host's immune system deduced from literature search and expert reviews of basic scientific articles and related clinical trial articles concerning anti-viral immunity may include, but is not limited to, activation of NK cells, T cell boosting, and/or increasing secretory Immunoglobulin A (sIgA) secretion by activating mucosal B cells. Activated NK cells can non-specifically kill the infected cells, and boosted T cells can specifically kill the infected cells. Also, sIgA as antibody playing an important role immunity in mucosa may increase musical immunity. As a result, the host's immune system may intensify to fight against viruses without undergoing severe symptoms in case of infection.

Embodiments for antiviral digital device are described herein. For example, the embodiments may include, but are not limited to: 1) deducing instructions which help intensify a host's immune system based on the aforementioned antiviral MOA, and 2) developing a digital apparatus and an application which include UI/UX which can deliver the instructions to the host (simultaneously the user of the application) and receive feedback.

The instructions which help intensify a host's immune system may indicate the host's specific practice or intervention in realizing the aforementioned antiviral MOA. The instructions to realize the ADI MOA of the present invention may include, but are not limited to, exercises for NK cell recruitment, exercises for T cell boosting, and/or vagal nerve innervation (VNI) for increase in sIgA secretion.

In one aspect, the present disclosure provides a method of maintaining, optimizing, or strengthening an immune system of a subject, the method comprising: providing, by an electronic device to the subject, an exercise module and/or a vagal nerve stimulation (VNS) module, each of the modules comprising one or more instructions for the subject to follow.

In some embodiments, the method described herein activates or increases production of natural killer (NK) cells in the subject. In some embodiments, the method reduces a change in a number of central T cells in the subject. In some embodiments, the method reduces a change in a number of effector T cells in the subject. In some embodiments, the method reduces a change in a number of effector memory T cells in the subject. In some embodiments, the method activates or increases production of naïve CD4 T cells in the subject. In some embodiments, the naïve T cells are activated or increased within one month from the providing. In some embodiments, the method reduces a change in a number of central CD4 T cells in the subject. In some embodiments, the method reduces a change in a number of effector CD4 T cells in the subject. In some embodiments, the method reduces a change in a number of effector memory CD4 T cells in the subject. In some embodiments, the method reduces a change in a number of naive CD8 T cells in the subject. In some embodiments, the method reduces a change in a number of central CD8 T cells in the subject. In some embodiments, the method reduces a change in a number of effector CD8 T cells in the subject. In some embodiments, the method reduces a change in a number of effector memory CD8 T cells in the subject. In some embodiments, the method activates or increases production of CD4 Treg cells in the subject. In some embodiments, the method activates naïve B cells into maturation in the subject. In some embodiments, the method increases naïve B cells in the subject. In some embodiments, the method increases memory B cells in the subject. In some embodiments, the method decreases plasma B cells in the subject.

The subject described herein may be human. The subject may be human of any age. A particular group of subject's that may benefit include humans that are less than or equal to about 45 years old as these subjects may have more effective response to VNS described herein. The subject may be older than about 3, 4, 5, 6, 7, 8, 9, or 10 years old for the subject to effectively follow the instructions described herein. In some embodiments, the subject may be a subject that is in need of maintaining, optimizing, or strengthening an immune system. In further embodiments, the subject may be diagnosed with an immune disease, may be on chemotherapy, may be a cancer patient, or may be a healthy subject.

The exercise module may stimulate sympathetic nerve system while the VNS module may stimulate parasympathetic nerve system. Thus, the effect of each of these two modules may be increased by having a lag time between the two modules. In certain embodiments, the exercise module and the vagal nerve stimulation module are provided with a lag time of about 2, 3, 4, 5, 6, 7, 8, 9, 10, 11, 12, 13, 14, 15 hours or more and of about 16, 15, 14, 13, 12, 11, 10, 9, 8, 7, 6, 5, 4, 3 hours or less. In certain embodiments, the exercise module and the vagal nerve stimulation module are provided with a lag time preferably of from about 3 hours to about 10 hours, preferably of from about 4 hours to about 8 hours, preferably of from about 4 hours to about 6 hours, preferably of from about 3 hours to about 6 hours, preferably of from about 2 hours to 5 hours, preferably of from about 3 hours to 5 hours, preferably about 8 hours to 10 hours, preferably of about 4 hours, preferably of about 5 hours, preferably of about 6 hours, or about 7 hours.

In certain embodiments, when the exercise module is provided, the exercise module comprises one or more instructions to stimulate a parasympathetic nervous system of the subject. In certain embodiments, when the exercise module is provided, the exercise module comprises at least one of moderate, aerobic and acute exercise instructions. In certain embodiments, when the exercise module comprising moderate exercise instructions is provided, maintaining, optimizing, or strengthening an immune system of the subject comprises stimulating NK cells. In certain embodiments, when the exercise module comprising moderate exercise instructions is provided, maintaining, optimizing, or strengthening an immune system of the subject comprises stimulating one or more of thymus cells, liver cells, bone marrow cells, tonsil cells, lymph node cells, spleen cells, blood cells, red blood cells, white blood cells, stem cells, B-cells, cytotoxic T-cells, Helper T-cells, plasma cells, immunoglobulins, natural killer (NK) cells, neutrophils, monocytes, platelets, and dendritic cells. In certain embodiments, when the exercise module comprising aerobic exercise and/or acute exercise instructions is provided, maintaining, optimizing, or strengthening an immune system of the subject comprises T cell boosting. In certain embodiments, when the exercise module comprising aerobic exercise instructions is provided, maintaining, optimizing, or strengthening an immune system of the subject comprises emerging CD4+ T cells to activate the immune system. In certain embodiments, when the exercise module comprising acute exercise instructions is provided, maintaining, optimizing, or strengthening an immune system of the subject comprises removing pre-existing T cells to secure T cells zone for new T cells. In certain embodiments, maintaining, optimizing, or strengthening an immune system of the subject comprises accelerating maturation of B-cells and/or differentiation of B cells to plasma cells. In certain embodiments, maintaining, optimizing, or strengthening an immune system of the subject comprises increasing a number responsive cells of the subject's immune system.

The instructions described herein can be specified and categorized as the following instructions to be embodied as an application through computer programming.

Moderate exercise: Moderate exercises may recruit NK cells. Intensive exercise, however, may make the host vulnerable to virus infection. Therefore, exercises hereinafter refer to moderate exercise which help keep up the heart rate. Generally, moderate exercise takes place about 10 minutes every day or 20 minutes 3-4 times per week. In certain embodiments, a method of the present disclosure can comprise repeating the method 2 times per week, 3 times per week, or more than 3 times per week. Examples of the exercise may include, but are not limited to, walking, cycling, yoga and Pilates. Depending on individuals' exercise performances and abilities, intensive/moderate exercise window varies. Hence, exercise prescriptions reflecting individuals' physical ability are needed. (A survey or simple physical test can be performed to diagnose individuals' exercise performances and physical abilities, or data analysis on prior exercise performances can be utilized to diagnose individuals' exercise performances and physical abilities.)

In certain embodiments, moderate exercise is determined based on one or both of age and target heart rate. In certain embodiments, moderate exercise is determined based on an ability or a disability. In certain embodiments, moderate exercise is determined based on weight. In other embodiments, moderate exercise is determined based on at least one of a heart rate (HR), a repetition maximum (RM), metabolic equivalents (METs), a maximal oxygen uptake capacity ($VO_{2max}$)/oxygen uptake reverse ($VO_2R$), or a rating of perceived exertion (RPE). In certain embodiments, the exercise module comprising aerobic exercise and/or acute exercise instructions is provided, and a level of the aerobic exercise and/or the acute exercise is determined prior to the providing. In certain embodiments, the exercise module comprising aerobic exercise and/or acute exercise instructions is provided, and a level of the aerobic exercise and/or the acute exercise is determined based on at least one of a HR, a RM, METs, a $VO_{2max}$/$VO_2R$, or a RPE.

In certain embodiments, moderate exercise for an about 15 year old subject comprises a target heart rate of between about 126 and about 150 beats per minute (bpm), moderate exercise for an about 20 year old subject comprises a target heart rate of between about 124 and about 147 bpm, moderate exercise for an about 25 year old subject comprises a target heart rate of between about 122 and about 145 bpm, moderate exercise for an about 30 year old subject comprises a target heart rate of between about 120 and about 142 bpm, moderate exercise for an about 35 year old subject comprises a target heart rate of between about 117 and about 139 bpm, moderate exercise for an about 40 year old subject comprises a target heart rate of between about 115 and about 137 bpm, moderate exercise for an about 45 year old subject comprises a target heart rate of between about 113 and about 134 bpm, moderate exercise for an about 50 year old subject comprises a target heart rate of between about 111 and about 132 bpm, moderate exercise for an about 55 year old subject comprises a target heart rate of between about 109 and about 129 bpm, moderate exercise for an about 60 year old subject comprises a target heart rate of between about 107 and about 127 bpm, moderate exercise for an about 65 year old subject comprises a target heart rate of between about 105 and about 124 bpm, moderate exercise for an about 70 year old subject comprises a target heart rate of between about 102 and about 122 bpm, moderate exercise for an about 75 year old subject comprises a target heart rate of between about 100 and about 119 bpm, moderate exercise for an about 80 year old subject comprises a target heart rate of between about 98 and about 117 bpm, moderate exercise for an about 85 year old subject comprises a target heart rate of between about 96 and about 114, and moderate exercise for an about 95 year old subject comprises a target heart rate of between about 92 and about 109.

In certain embodiments, the target heart rate is determined, at least in part, based on feedback from exercise performed prior to the providing. It is contemplated that a subject who is athletic (e.g., routinely performs exercise) can have a higher target heart rate to experience moderate exercise than a subject who does not regularly exercise. Similarly, it is contemplated that a subject that is healthy (e.g., has no physical disability) can have a higher target heart rate to experience moderate exercise than a subject that does have a physical disability. In certain embodiments, an increase in the subject's heart rate by about 1, 2, 3, 4, 5, 6, 7, 8, 9, 10, 11, 12, 13, 14, 15, 16, 17, 18, 19, 20 bpm or greater and about 21, 20, 19, 18, 17, 16, 15, 14, 13, 12, 11, 10, 9, 8, 7, 6, 5, 4, 3, 2 bpm or less relative to the target heart rate for the moderate exercise module results in a decrease in the target heart rate for a subsequent moderate exercise module. In certain embodiments, a decrease in the subject's heart rate by greater than 1, 2, 3, 4, 5, 6, 7, 8, 9, 10, 11, 12, 13, 14, 15, 16, 17, 18, 19 or 20 bpm and about 21, 20, 19, 18, 17, 16, 15, 14, 13, 12, 11, 10, 9, 8, 7, 6, 5, 4, 3, 2 bpm or less relative to the target heart rate for the moderate exercise module results in an increase in the target heart rate for a subsequent moderate exercise module.

Aerobic and/or acute exercises: Aerobic and/or acute exercises may boost T cells. Stimuli through aerobic exercises may create a desirable immune environment for young T cells, and acute exercises may help secure T cell zones for the young T cells.

In some embodiments, the same exercise instruction(s) may serve as moderate, acute and/or aerobic exercise instructions simultaneously. In certain embodiments, the exercise module describe herein comprises at least one exercise instructions for simultaneous aerobic and acute exercise. In certain embodiments, one or more instructions comprise instructions for resistance exercise, concurrent exercise, and/or benchmark exercise. In certain embodiments, the benchmark exercise comprises one or more selected from the group consisting of jumping jacks, squats, and pushups. In certain embodiments, the method further comprises repeating the benchmark exercise at least one times in succession, at least 2 times in succession, at least 3 times in succession, at least 4 times in succession, at least 5 times in succession, at least 6 times in succession, at least 7 times in succession, at least 8 times in succession, at least 9 times in succession, or at least 10 times in succession.

In certain embodiments, the one or more instructions comprise one or more instructions for walking, biking, aerobic dance and/or swimming. It is contemplated that certain exercises can be suitable for low, moderate or vigorous exercise (e.g., depending on an intensity with which the subject performs the exercise). For example, running slowly (e.g., 2 miles per hour) can be suitable for a low intensity exercise, whereas running faster (e.g., 3-5 miles per hour) can be suitable for moderate or vigorous exercise.

Vagal nerve stimulation (VNS): VNS may increase sIgA secretion. There are a lot of immune cells near gastrointestinal mucosa. Through VNS mucosal lymphoid follicle becomes B cell maturation, and after B cell migration to mucosal action point, it develops into a plasma cell to increase the secretion of sIgA. VNS can be comprised of the stimuli on the five senses, for example, including 10-minute of intensive cold massage or deep breathing.

In certain embodiments, as described herein, when the vagal nerve stimulation module is provided, the vagal nerve stimulation module comprises one or more instructions to stimulate a sympathetic nervous system of the subject. In certain embodiments, the vagal nerve stimulation module is provided, and the vagal nerve stimulation module comprises at least one instructions selected from the group consisting of sense stimulation instructions for sight, sound, touch, taste, and smell.

In some embodiments, measures to practice various exercises and VNS for boosting immunity without the intervention of the application may be included (e.g., training, exercise manual, and YouTube videos.). In other embodiments, measures to deliver exercises and VNS instructions through a simple application without evidence based on MOA or the results of clinical trials based on the MOA (such as a health application) may be provided.

In certain embodiments, the vagal nerve stimulation module described herein comprises one or more sense stimulation instructions for sight, and the one or more sense stimulation instructions for sight include one or more instructions to view one or more figures to stimulate autonomic nervous system. In certain embodiments, the electronic device receives and displays the figures. In certain embodiments, the figures comprise one or more images for inducing fear in the subject. In certain embodiments, the vagal nerve stimulation module comprises one or more sense stimulation instructions for sound, and the one or more sense stimulation instructions for sound include one or more instructions to hear one or more sounds to cause horror or relaxation. In certain embodiments, the one or more sounds to cause relaxation comprise white noise. In certain embodiments, the electronic device receives and plays the sounds. In certain embodiments, the vagal nerve stimulation module comprises one or more sense stimulation instructions for touch, and the one or more sense stimulation instructions for touch include one or more instructions for abdominal breathing, controlling rate of breathing, holding breath, cold massage, bathing face in cold water, coughing, and skin massage. In certain embodiments, the vagal nerve stimulation module comprises one or more sense stimulation instructions for touch, and the one or more sense stimulation instructions for touch include one or more instructions for controlling rate of breathing. In certain embodiments, the rate of breathing can be 3 breaths per minute, 4 breaths per minute, 5 breathes per minute, 6 breaths per minute, 7 breaths per minute, 8 breaths per minute, 9 breaths per minute, 10 breaths per minute, 15 breaths per minute, 20 breaths per minute, or greater than 20 breaths. In certain embodiments, the vagal nerve stimulation module comprises one or more sense stimulation instructions for smell, and the one or more sense stimulation instructions for smell include one or more instructions to relax. In certain embodiments, the electronic device is configured to release a scent for aroma therapy.

In certain embodiments, the exercise module is provided prior to the vagal nerve stimulation module. The exercise module may be provided after the vagal nerve stimulation module.

Embodiments described herein may extend the effects of boosting the immune system not only to viral diseases but to other infectious diseases as well. For example, not only UR (upper respiratory tract) but also GI (Gastrointestinal infections) infection is included.

Figure 4:
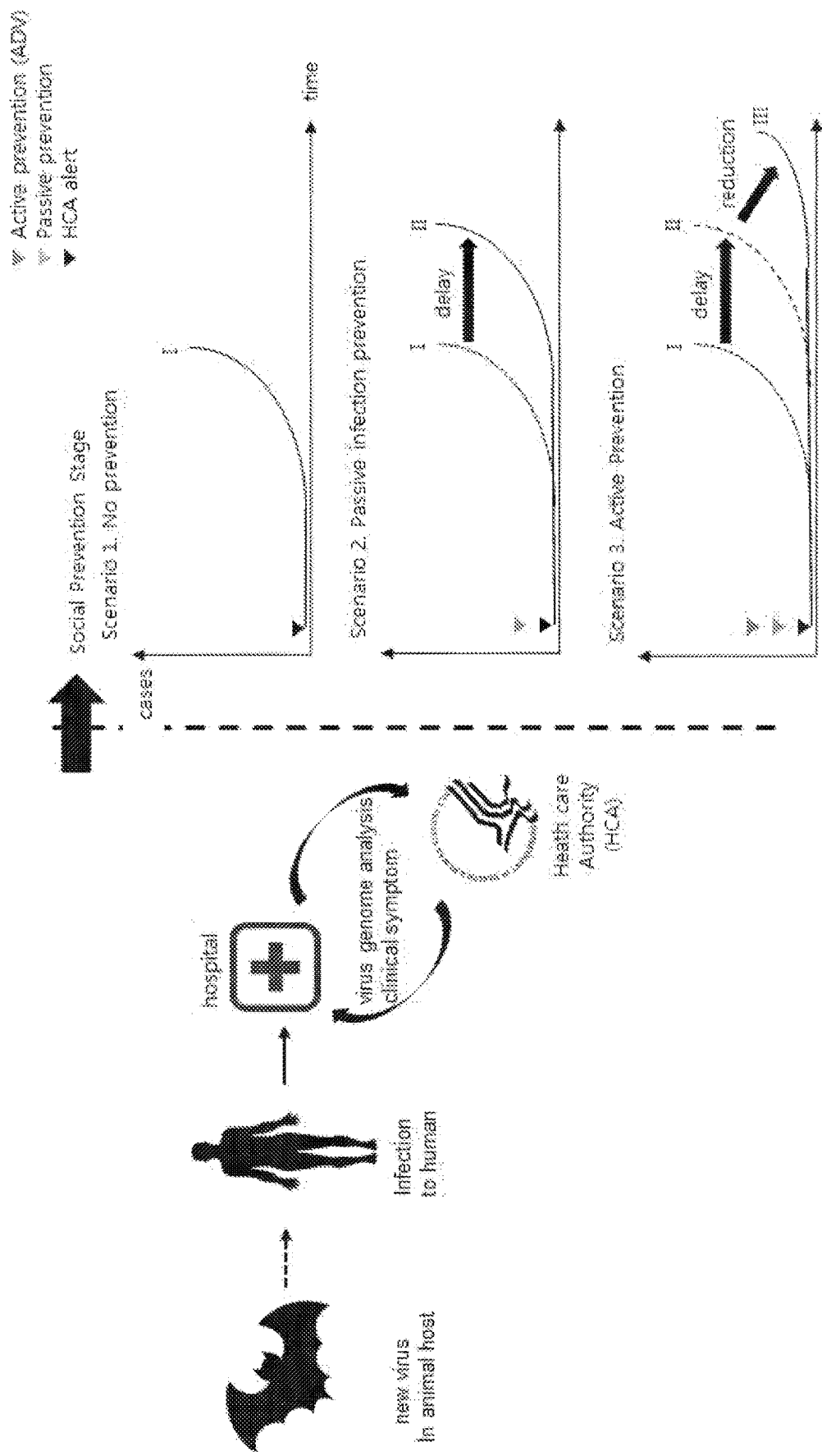
FIG. 4 illustrates an example of active antiviral digital immunity (ADI) effect on reduction in peaks of outbreak in viral disease epidemics.

FIG. 4 is a diagram illustrating an example active antiviral digital immunity (ADI) effect on reduction in peaks of outbreak in viral disease epidemics. In FIG. 4, the activation of ADI (antiviral digital immunity) through ADD (antiviral digital device) is shown with the progress of the virus outbreak. Hospitals and the health care authorities perform analyses of the symptoms of infected patients and the sources of infection after the mutated virus from the animals had infected humans. The responsible health care authorities may judge the analyzed results, alert the society of the disease's dangerousness, properties, symptoms and others, and enter into the passive prevention of the disease. I of Scenario 1 is a graph showing the increase of the number of patients when no preemptive measures were taken for the spread of the epidemic. As mentioned in FIG. 2, the number of patients dramatically increases when a given amount of time passes after the alert. II of Scenario 2 is a graph showing the increase of the number of patients when passive prevention methods such as wearing masks, practicing hand hygiene and performing social distancing were employed. It is observed that the virus outbreak peak is delayed for a certain period of time.

III of Scenario 3 is a graph showing the increase of the number of patients when active prevention methods such as the activation of ADI through ADD were employed along with passive prevention methods. Not only the delay in the virus outbreak peak but also the reduction in outbreak peak is expected. The activation of ADI through ADD enhances individuals' providing immunity by performing particular instructions using the application during the golden time of the disease management, that is, between the time when the alert was made and the time when mass infection cases increase drastically. Ultimately, it serves to enable the management of the new viral disease within the health care system capacity by raising the proportion of asymptomatic and lowering that of severe symptomatic.

Figure 5:
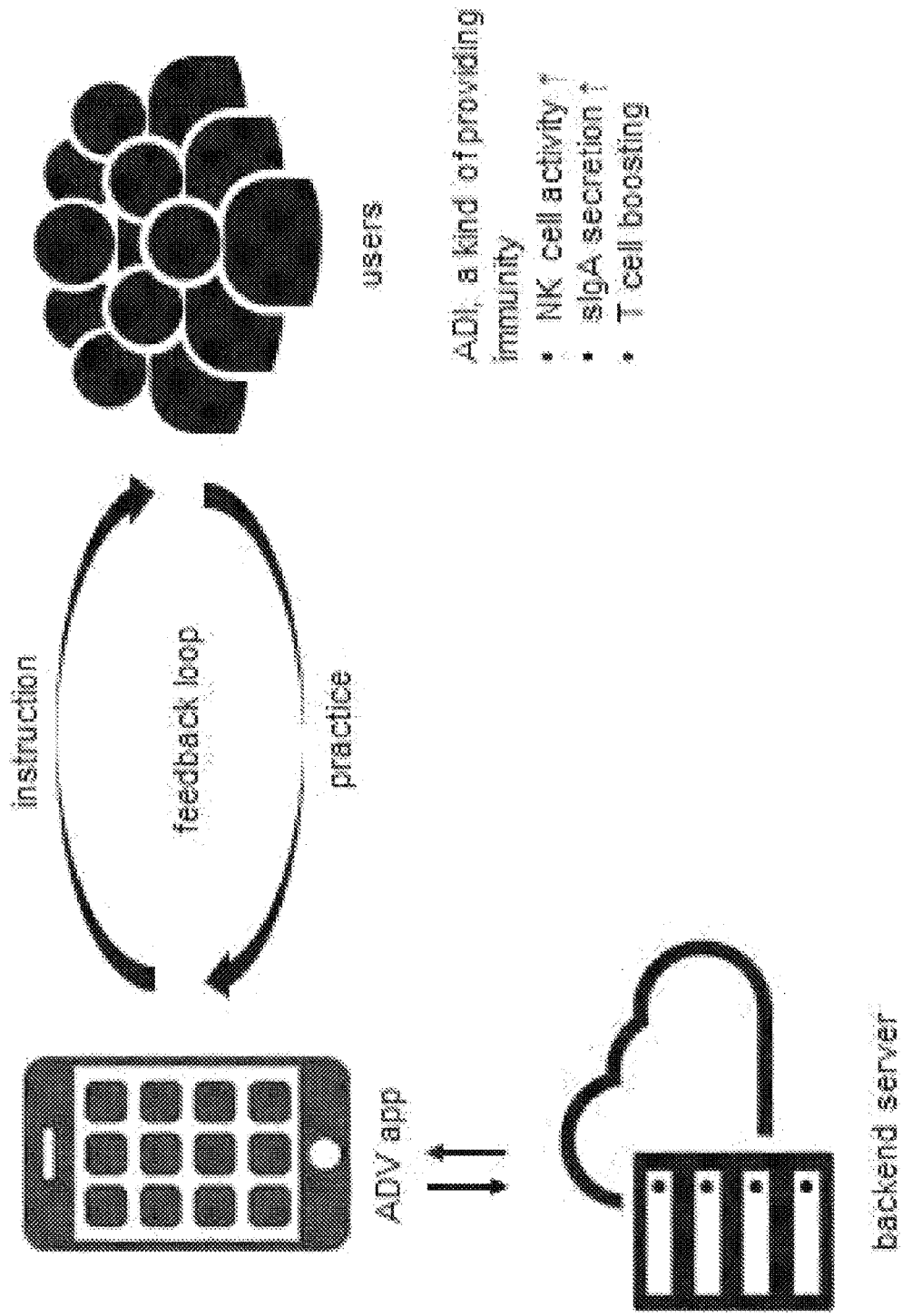
FIG. 5 illustrates an example of antiviral digital device (ADD) application to personnel interaction.

FIG. 5 is a diagram illustrating an example antiviral digital device (ADD) application to personnel interaction. In FIG. 5, the process of how ADD activates an individual's ADI is shown. ADD may be embodied in the application of digital devices such as a desktop computer, a laptop computer, a tablet or a smartphone. The user may download the app to receive instructions through ADD UI and practice them. The user's practice may give feedback to the application through various means such as log-in/out information, users' ratings and reviews/records, and passive data gathering via sensors. This instruction-practice feedback loop may enhance the user's providing immunity and hence the user's resistance towards the infection. Taking a look at a more specific response of the immune system to ADD, the process of instruction-practice feedback may improve the user's NK cell activation, increase the secretion of slgA, and boost T cells. ADD may be designed based on the MOA which leads the aforementioned responses of the immune system. Consequently, the instructions that a user practices may result in the individual's providing immunity, and therefore the goal of active prevention is achieved.

Figure 6:
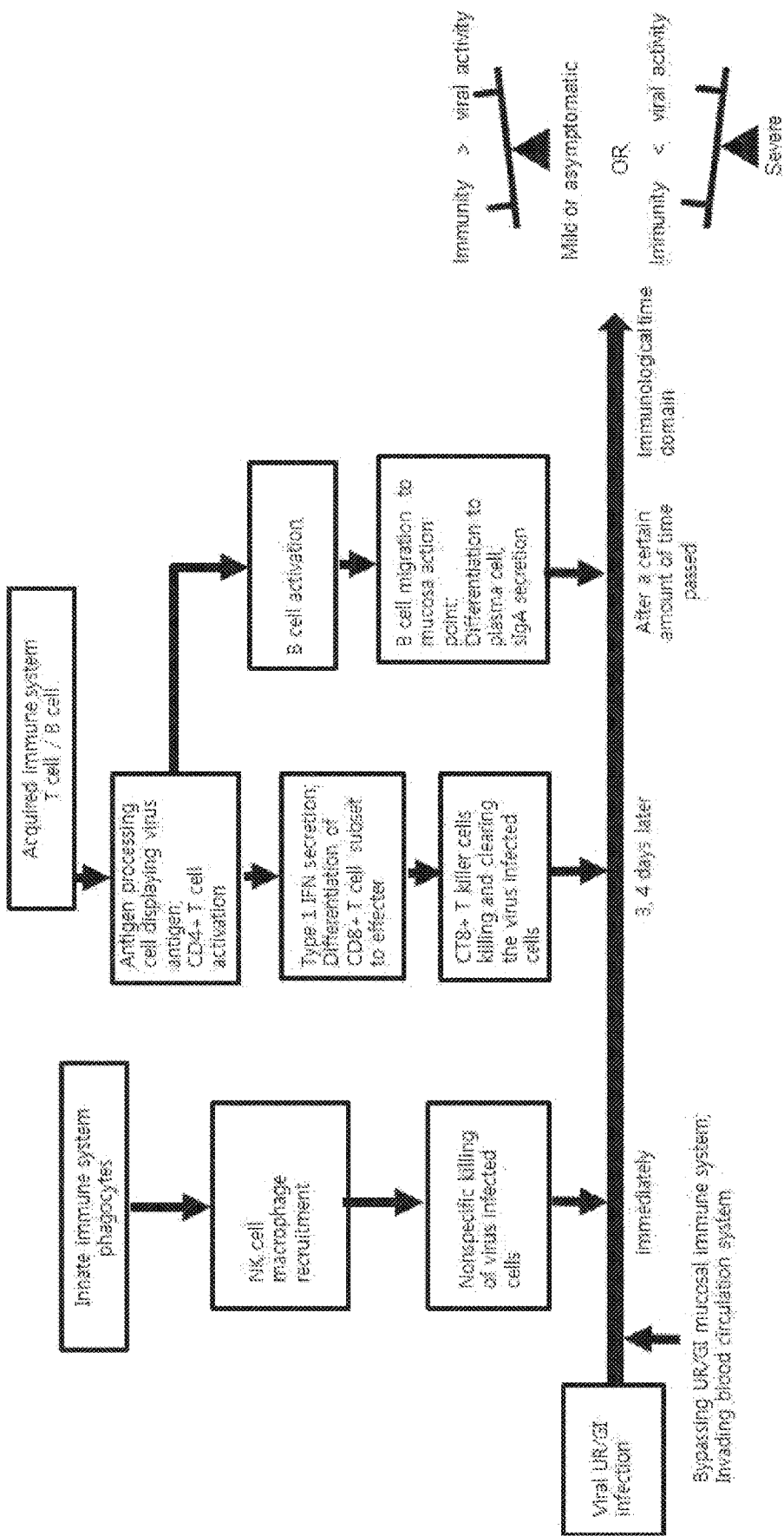
FIG. 6 illustrates an example of immune response to viral infection depending on immunological time domain.

FIG. 6 is a diagram illustrating an example immune response to viral infection depending on immunological time domain. In FIG. 6, the sequential responses of a host's immune system in general virus infection is shown. URT (upper respiratory tract)/GI (gastrointestinal) infection caused by viruses may immediately cause phagocytosis of phagocytes and NK cells in the innate immune system. The viruses that have avoided or incapacitated this stage may be attacked by viral antigen specific acquired immune system, which is connected with APC (antigen processing cell)-CD4+ T-cells and CD8+T killer cells. This process may take place in 3-4 days after the infection, and overwhelming cytokine response in the process results in cytokine storm. Some parts of CD4+ T cells may activate B cells to induce antibody-secreting cells which produce viral antigen specific antibody. Some B cells may then develop into memory B cells which have the antibody production capacity against the particular antigen to later gain acquired immunity against the same infection. This process may take a longer time than the aforementioned two processes. After the immunity of the innate immune system and the acquired immune system overcome the virus activities, the host may become a mild symptomatic or asymptomatic. Reversely, if the virus activities overwhelm the immunity of the innate immune system and the acquired immune system, the host may become a severe symptomatic.

Figure 7:
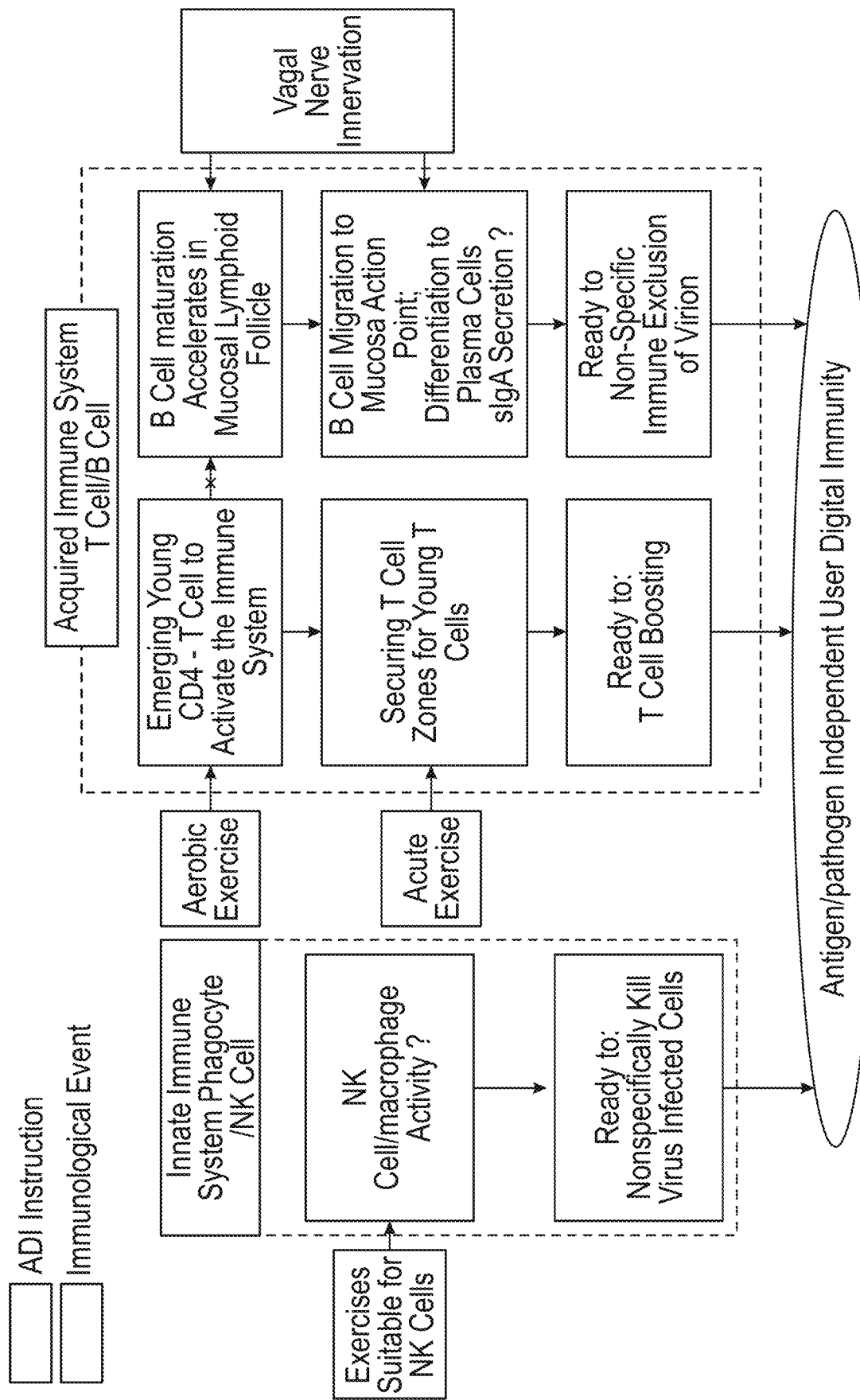
FIG. 7 illustrates an example of mechanism of antiviral digital immunity (ADI)

FIG. 7 is a diagram illustrating an example mechanism of antiviral digital immunity (ADI). In FIG. 7, the mechanism how ADD produces a user's ADI is illustrated. The blue boxes represent a series of behaviors that a user practices through the instructions on ADD, and the green boxes present the immune system of FIG. 6 and its results in accordance with the user's behaviors. Exercises suitable for NK cells may activate NK cells to non-specifically kill the infected cells through the innate immune system. Aerobic and acute exercises may help secure T cell zones for young T cells and boost T cells in cases of infection. Lastly, vagal nerve innervation may create an environment where non-specific antigen immune exclusion can effectively take place by activating B cells at the mucosa and increasing the secretion of sIgA, which plays an important role in mucosal immunity.

Hence, ADI, which enhances the host's immunity against the virus through the user's instructions on ADD, can be defined.

Figure 8:
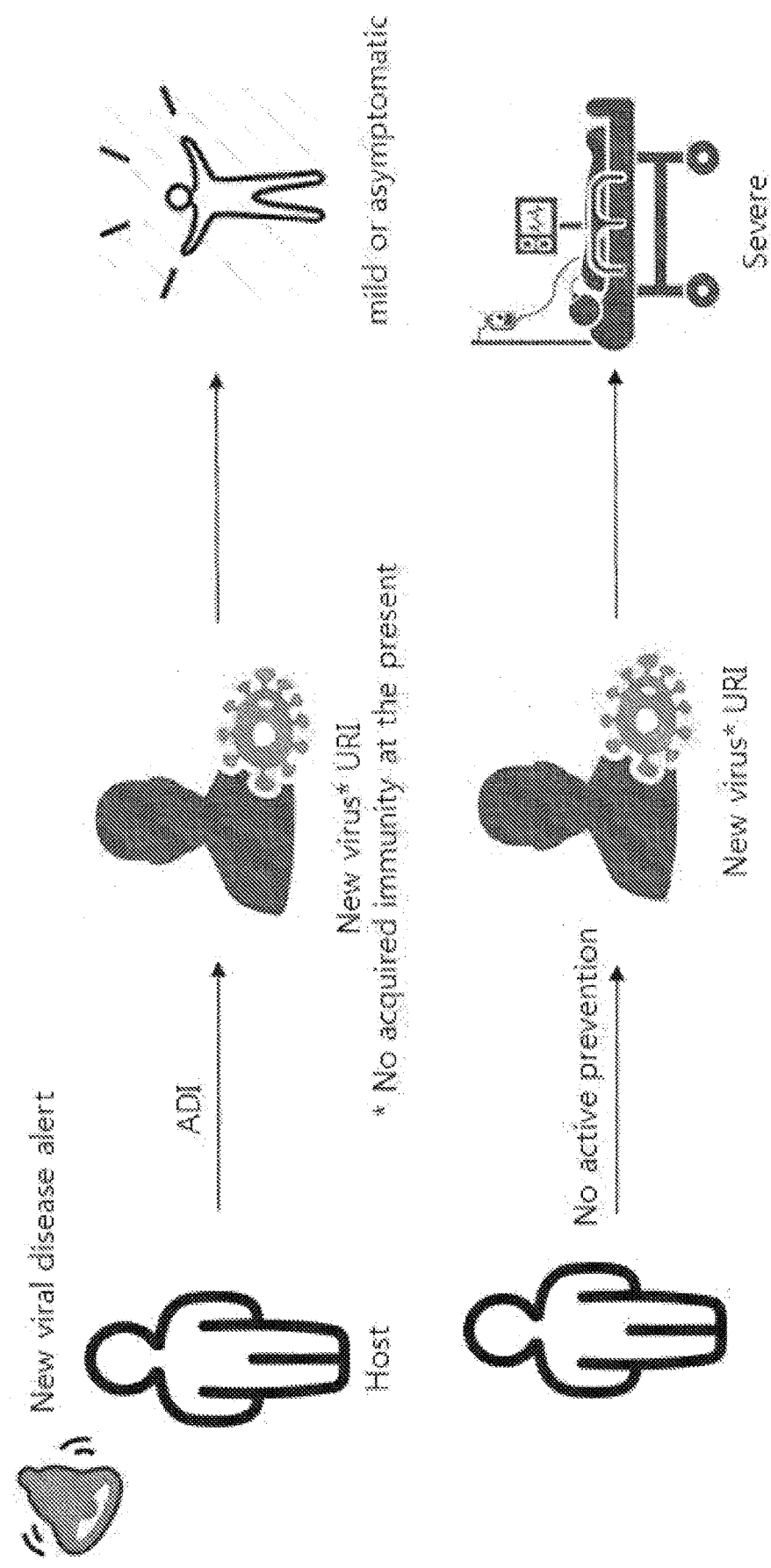
FIG. 8 illustrates an example of ADI prevention effect on new virus infection.

FIG. 8 is a diagram illustrating an example ADI prevention effect on new virus infection. When the dangerousness of the new viral disease is alerted to the society, ADD may enhance an individual's providing immunity by stimulating and activating the individual's immune system until the viral infection increases drastically. This enhancement in the individual's providing immunity may intensify the patient's immunity so that the patient only experiences mild symptoms when infected and easily recovers from the infection.

FIG. 9 is a diagram illustrating an example ADD application. In FIG. 9, NK cell instructions, vagal nerve innervation instructions, and T cell instructions that are introduced in FIG. 7 are specified, and these are further reflected in the application planning. The application programming and the application design based on the planning can successfully embody the ADD application.

Figure 10:
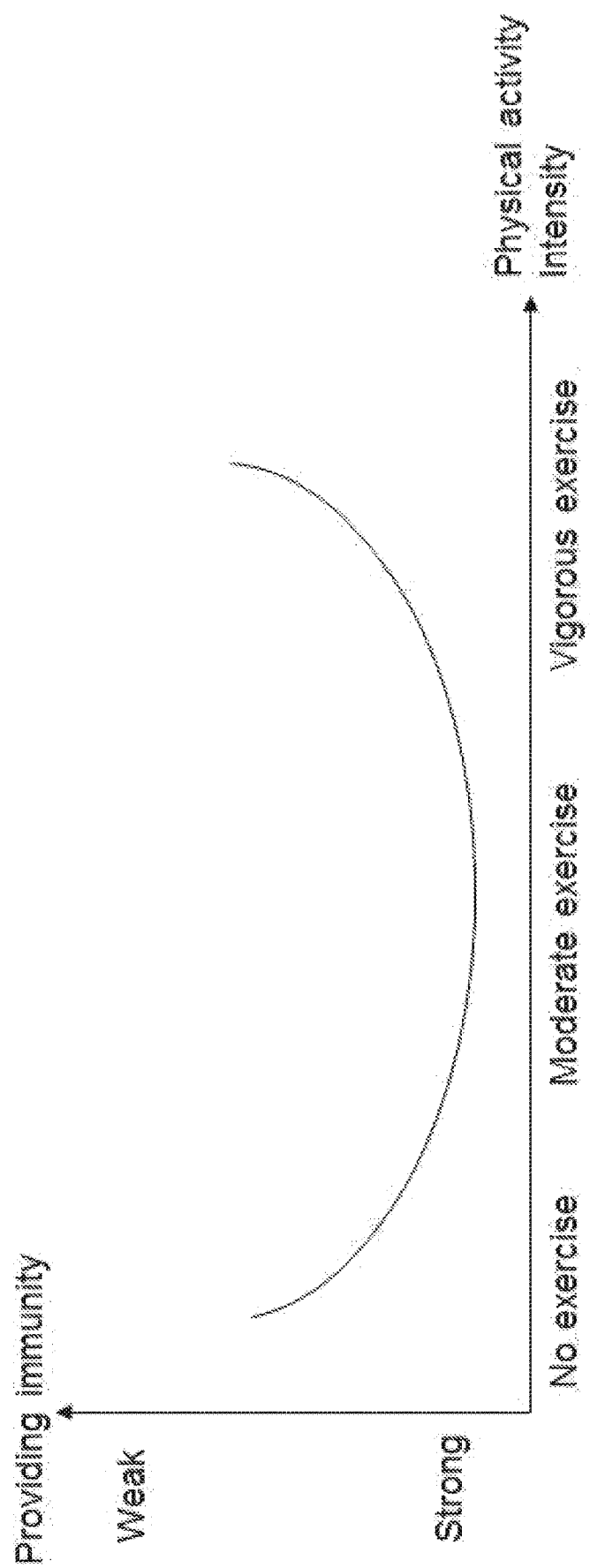
FIG. 10 illustrates exemplary exercises suitable to natural killer (NK) cells.

FIG. 10 is a diagram illustrating example exercises suitable to natural killer (NK) cells. Exercises suitable for NK cells may indicate 10-minute long moderate exercises per day which help keep up the heart rate (20 minutes, 3-4 times a week). Examples may include, but are not limited to, walking, cycling, yoga and/or Pilates. It is desirable to classify individuals' physical strengths into three categories based on their physical fitness, and prescribe exercises using the classification.

Practicing moderate exercise may be important when it comes to exercises suitable for NK cells. No exercise or intensive exercise can weaken the immune system as can be seen from FIG. 10.

FIG. 11 is a diagram illustrating example stimulation for vagal nerve innervation. In FIG. 11, a table organizing various means to stimulate the vagal nerve is described. The vagal nerve stimulation can be practiced, for example, by involving visual, auditory, tactual, gustatory and olfactory senses, molecules, or the like. Vagal nerve innervation instructions may include, but are not limited to, cold massage, deep breathing, abdominal breathing, listening to music, watching movies, and/or the like.

FIG. 12 is a diagram illustrating example exercises suitable for T cells. The "acute exercise" can be defined as a single bout of exercise. Acute exercise may impact on circulation and leave blood to travel to tissues where they are more likely to encounter infected cells. In addition, the acute effects of exercise can stimulate a mobilization of senescent immune cells and secure T cell zones for young T cells. As illustrated in FIG. 12, the exercises suitable for T cells may include, but is not limited to, both aerobic and anaerobic exercise. However, it is noted that chronic exercise may be a safe mode of intervention to improve the effectiveness of flu vaccination in elderly populations without harmful side effects.

Figure 13:
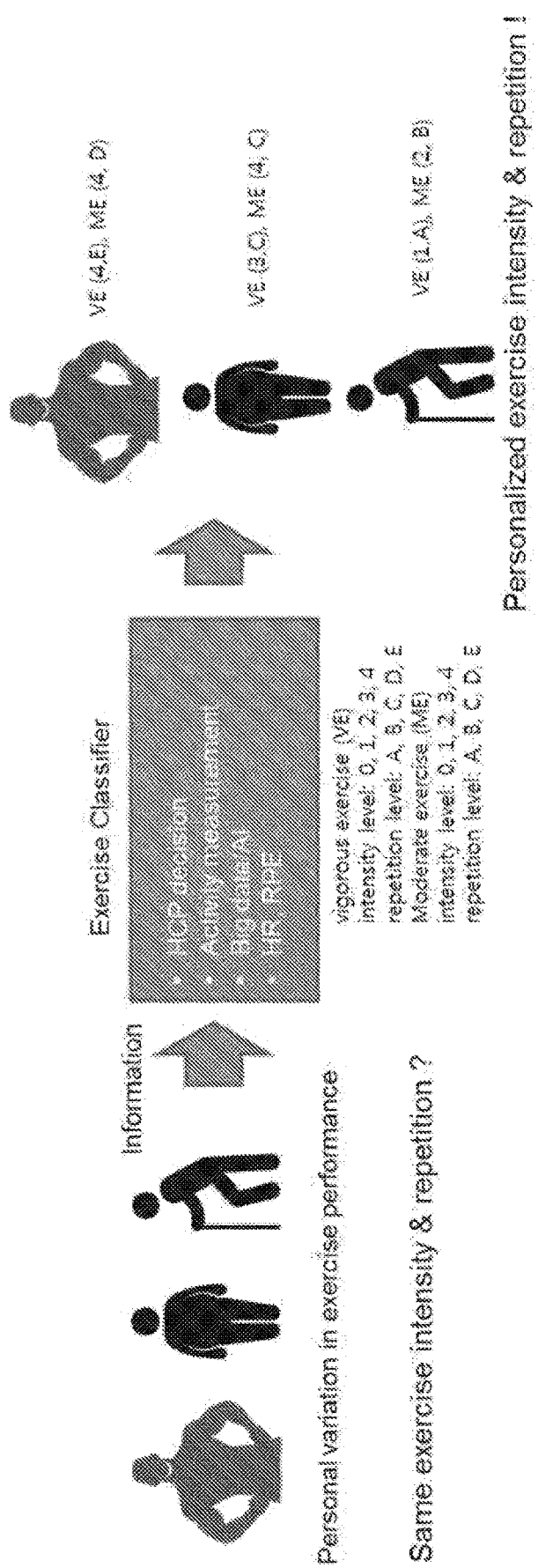
FIG. 13 illustrates an exemplary exercise classifier.

FIG. 13 is a diagram illustrating an example exercise classifier. There may be various exercise classifiers, and the examples may include, but are not limited to, HR (heart rate), RM (repetition maximum), METs (metabolic equivalents), VO2max/VO2R (maximal oxygen uptake capacity/oxygen uptake reverse), RPE (rating of perceived exertion) or the like.

Exercise performances may vary from users to users due to various factors such as age, sex, exercise ability, exercise history and underlying diseases (e.g., cardiovascular diseases, hypertension, diabetes).

The ADD instruction which can induce ADI may cover "Exercise Classifier," which suggests personalized exercise intensity and repetition.

"Exercise Classifier" may operate as follows to provide personalized exercise prescription. For example, 1) If physically visiting a hospital: the HCP (healthcare professionals) judge the user's exercise performances based on the data of prior visits or physical tests before prescribing/recommending an ADD, 2) if using Activity tracker (e.g., HR detector): the algorithm judges the user's exercise performances based on the user's activity data, 3) AI judges the user's exercise performances based on the analysis of long time tracing data (Big data), 4) if taking self-care: as there are no HCP or subsidiary devices, a survey in the format of RPE can be utilized.

Figure 14:
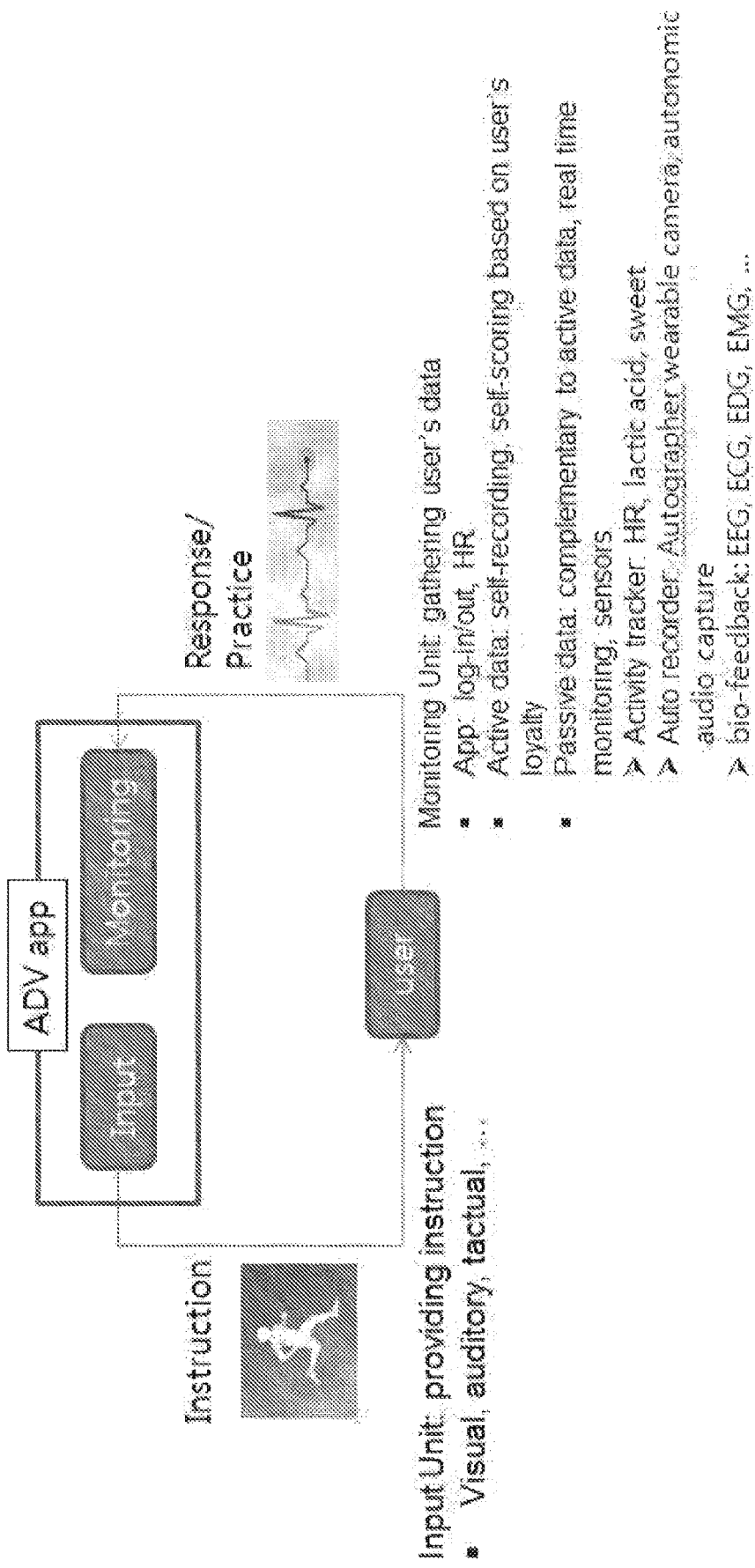
FIG. 14 illustrates an exemplary instruction input and practice monitoring of ADD application.

FIG. 14 is a diagram illustrating an example instruction input and practice monitoring of ADD application. In FIG. 14, various combination between input and monitoring of ADD app is described. The instruction input might be provided to user by visual display, auditory narration, touch/vibration, etc. The practice can be classified to three categories: 1) application log-in/out information; 2) active data which are generated by user's typing or recording; and 3) passive data which are gathered by sensors. The sensors for passive data gathering may include activity trackers, auto recorders, bio-feedback instruments, or the like.

Figure 15:
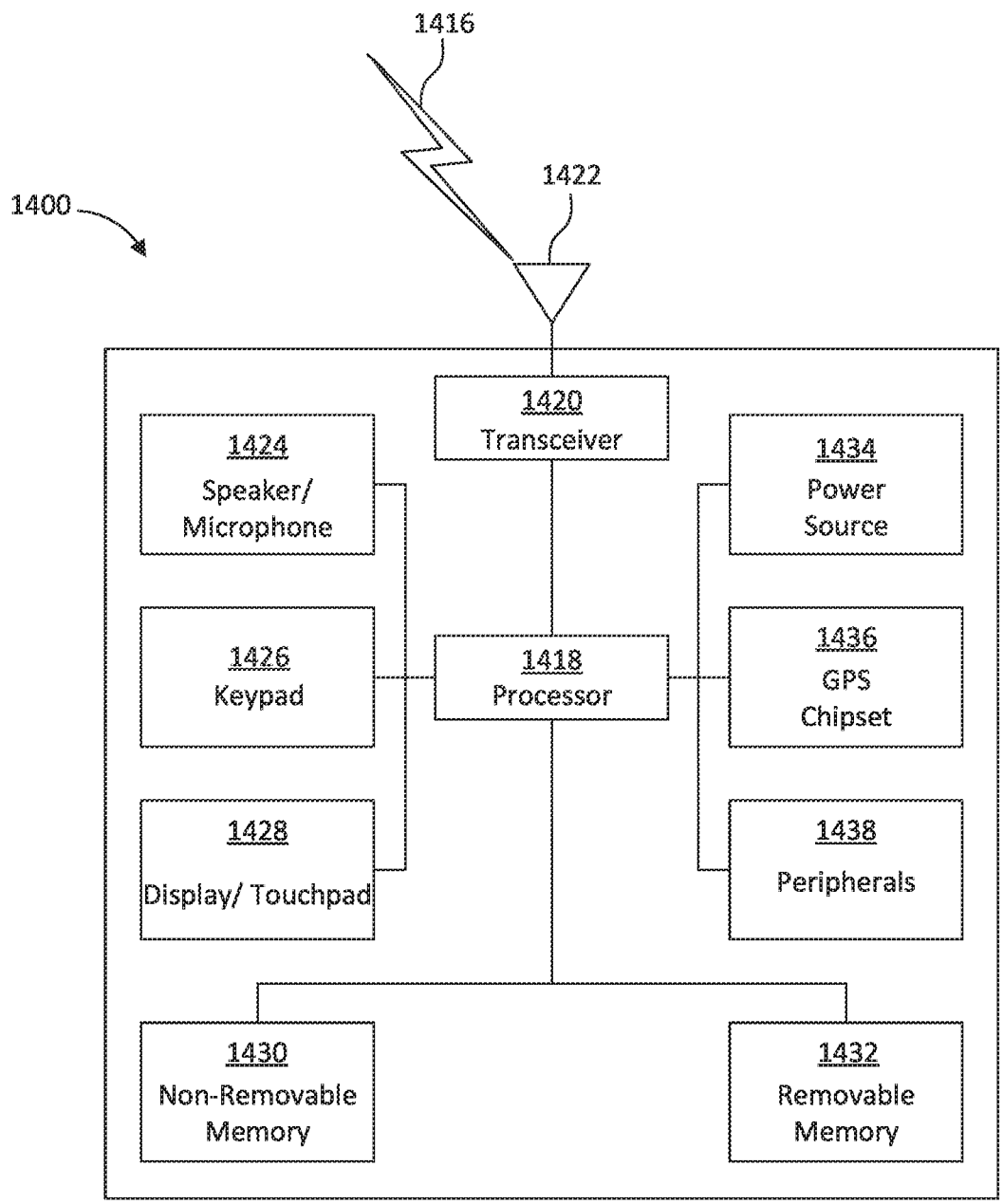
FIG. 15 illustrates an example device that can be used for antiviral digital device (ADD)

FIG. 15 is a system diagram illustrating an example device 1400 that can be used for providing antiviral digital immunity (ADI), which may be used in combination with any of other embodiments described herein. As shown in FIG. 15, the device 1400 may include a processor 1418, a transceiver 1420, a transmit/receive element 1422, a speaker/microphone 1424, a keypad 1426, a display/touchpad 1428, non-removable memory 1430, removable memory 1432, a power source 1434, a global positioning system (GPS) chipset 1436, and/or other peripherals 1438, among others. It will be appreciated that the device 1400 may include any sub-combination of the foregoing elements while remaining consistent with an embodiment. By way of example, the device 1400 may include a mobile device, a user equipment (UE), a mobile station, a fixed or mobile subscriber unit, a subscription-based unit, a pager, a cellular telephone, a personal digital assistant (PDA), a smartphone, a laptop, a netbook, a personal computer, a wireless sensor, a hotspot or Mi-Fi device, an Internet of Things (IoT) device, a watch or other wearable, a head-mounted display (HMD), a vehicle, a drone, a medical device and applications (e.g., remote surgery), an industrial device and applications (e.g., a robot and/or other wireless devices operating in an industrial and/or an automated processing chain contexts), a consumer electronics device, a device operating on commercial and/or industrial wireless networks, and the like.

The processor 1418 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs), any other type of integrated circuit (IC), a state machine, and the like. The processor 1418 may perform data processing, power control, input/output processing, sensor date processing, and/or any other functionality that enables the device 1400 to provide antiviral digital device. The processor 1418 may be coupled to the transceiver 1420, which may be coupled to the transmit/receive element 1422. While FIG. 15 depicts the processor 1418 and the transceiver 1420 as separate components, it will be appreciated that the processor 1418 and the transceiver 1420 may be integrated together in an electronic package or chip.

The transmit/receive element 1422 may be configured to transmit data to, or receive data from a sever located in a medical institution. For example, medical instructions from a doctor/medical information sensed from a user may be received/transmitted from/to the server, via a base station over the air interface 1416. In one embodiment, the transmit/receive element 1422 may be an antenna configured to transmit and/or receive RF signals. In an embodiment, the transmit/receive element 1422 may be an emitter/detector configured to transmit and/or receive IR, UV, or visible light signals, for example. In yet another embodiment, the transmit/receive element 1422 may be configured to transmit and/or receive both RF and light signals. It will be appreciated that the transmit/receive element 1422 may be configured to transmit and/or receive any combination of wireless signals. The transceiver 1420 may be configured to modulate the signals that are to be transmitted by the transmit/receive element 1422 and to demodulate the signals that are received by the transmit/receive element 1422.

The processor 1418 of the device 1400 may be coupled to, and may receive user input data from, the speaker/microphone 1424, the keypad 1426, the display/touchpad 1428 (e.g., a liquid crystal display (LCD) display unit or organic light-emitting diode (OLED) display unit) and/or the peripherals 1438 (e.g., sensors or digital camera). The processor 1418 may also output user data or digital instructions to the speaker/microphone 1424, the keypad 1426, the display/touchpad 1428 and/or the peripherals 1438. In addition, the processor 1418 may access information from, and store data in, any type of suitable memory, such as the non-removable memory 1430 and/or the removable memory 1432. The non-removable memory 1430 may include random-access memory (RAM), read-only memory (ROM), a hard disk, or any other type of memory storage device. The removable memory 1432 may include a subscriber identity module (SIM) card, a memory stick, a secure digital (SD) memory card, and the like. In other embodiments, the processor 218 may access information from, and store data in, memory that is not physically located on the device 1400, such as on a server or a home computer (not shown).

The processor 1418 may receive power from the power source 1434, and may be configured to distribute and/or control the power to the other components in the device 1400. The power source 1434 may be any suitable device for powering the device 1400. For example, the power source 1434 may include one or more dry cell batteries (e.g., nickel-cadmium (NiCd), nickel-zinc (NiZn), nickel metal hydride (NiMH), lithium-ion (Li-ion), etc.), solar cells, fuel cells, and the like.

The processor 1418 may also be coupled to the GPS chipset 1436, which may be configured to provide location information (e.g., longitude and latitude) regarding the current location of the device 1400. In addition to, or in lieu of, the information from the GPS chipset 1436, the device 1400 may receive location information over the air interface 1416 from a base station and/or determine its location based on the timing of the signals being received from two or more nearby base stations. It will be appreciated that the device 1400 may acquire location information by way of any suitable location-determination method while remaining consistent with an embodiment.

The processor 1418 may further be coupled to other peripherals 238, which may include one or more software and/or hardware modules that provide additional features, functionality and/or wired or wireless connectivity. For example, the peripherals 238 may include an accelerometer, an e-compass, a satellite transceiver, a digital camera (for photographs and/or video), a universal serial bus (USB) port, a vibration device, a television transceiver, a hands free headset, a Bluetooth® module, a frequency modulated (FM) radio unit, a digital music player, a media player, a video game player module, an Internet browser, a Virtual Reality and/or Augmented Reality (VR/AR) device, an activity tracker, and the like. The peripherals 1438 may include one or more sensors. The sensors may be one or more of a gyroscope, an accelerometer, a hall effect sensor, a magnetometer, an orientation sensor, a proximity sensor, a temperature sensor, a time sensor; a geolocation sensor, an altimeter, a light sensor, a touch sensor, a magnetometer, a barometer, a gesture sensor, a biometric sensor, a humidity sensor and the like.

In one aspect, the present disclosure provides a method of maintaining, optimizing, or strengthening an immune system of a subject, the method comprising: providing, by an electronic device to the subject, a first exercise module and/or a first vagal nerve stimulation (VNS) module, each of the first modules comprising one or more first instructions for the subject to follow. In certain embodiments, the method comprises further providing, by the electronic device to the subject, a second exercise module and/or a second vagal nerve stimulation module, each of the second modules comprising one or more second instructions, wherein the electronic device (i) comprises a sensor sensing adherence by the subject to the first instructions of the first modules, (ii) transmits adherence information, based on the adherence, to a server, and (iii) receives the one or more second instructions from the server based on the adherence information.

In some embodiments, the method described herein activates or increases production of natural killer (NK) cells in the subject. In some embodiments, the method reduces a change in a number of central T cells in the subject. In some embodiments, the method reduces a change in a number of effector T cells in the subject. In some embodiments, the method reduces a change in a number of effector memory T cells in the subject. In some embodiments, the method activates or increases production of naïve CD4 T cells in the subject. In some embodiments, the naïve T cells are activated or increased within one month from the providing. In some embodiments, the method reduces a change in a number of central CD4 T cells in the subject. In some embodiments, the method reduces a change in a number of effector CD4 T cells in the subject. In some embodiments, the method reduces a change in a number of effector memory CD4 T cells in the subject. In some embodiments, the method reduces a change in a number of naive CD8 T cells in the subject. In some embodiments, the method reduces a change in a number of central CD8 T cells in the subject. In some embodiments, the method reduces a change in a number of effector CD8 T cells in the subject. In some embodiments, the method reduces a change in a number of effector memory CD8 T cells in the subject. In some embodiments, the method activates or increases production of CD4 Treg cells in the subject. In some embodiments, the method activates naïve B cells into maturation in the subject. In some embodiments, the method increases naïve B cells in the subject. In some embodiments, the method increases memory B cells in the subject. In some embodiments, the method decreases plasma B cells in the subject.

In another aspect, the server receives the one or more second instructions from an external reviewer. In some embodiments, the external reviewer comprises a health professional (e.g., a healthcare provider or doctor). In some embodiments, the external reviewer comprises an artificial intelligence (AI). The term "artificial intelligence" can refer to intelligence exhibited by machines. In computer science, an ideal "intelligent" machine is a flexible rational agent that perceives its environment and takes actions that maximize its chance of success at some goal (e.g., maintaining, optimizing, or strengthening an immune system of a subject). Colloquially, the term "artificial intelligence" is applied when a machine mimics "cognitive" functions that humans associate with other human minds, such as "learning" and "problem solving. The term artificial intelligence may refer to an algorithm that may apply learning skills on multiple types of information (such as physiological information, additional information and person's medical history).

In some embodiments, the digital device comprises a sensor, and the sensor comprises one or more of: a camera, an accelerometer, a magnetometer, a light sensor, a microphone, a proximity sensor, a touch sensor, a gyroscope, a Global Positioning System (GPS) sensor, an ambient light sensor, a fingerprint sensor, a pedometer, a heart rate sensor, and a thermometer. In some embodiments, the sensor comprises a touch sensor, and the subject provides the adherence information to the electronic device using the touch sensor. In certain embodiments, the digital device is selected from the group consisting of a smart phone, a smart watch, smart jewelry, and a head mounted display.

Based on the mechanism of action in and the therapeutic hypothesis and digital therapeutic hypothesis for maintaining, optimizing strengthening an immune system of a subject, a doctor (a second user) may prescribe digital therapeutics, which are realized in a digital apparatus and an application for treating maintaining, optimizing strengthening an immune system of a subject, for the corresponding patient. In this case, the digital instruction generation unit is a device configured to provide a prescription of the digital therapeutics to a patient as a specific behavioral instruction that the patient may execute based on the interaction between the biochemical factors for maintaining, optimizing strengthening an immune system of a subject and the patient's behaviors. For example, all types of biochemical factors that may cause maintaining, optimizing strengthening an immune system of a subject may be considered.

The digital instruction generation unit may generate digital instructions based on the inputs from the doctor. In this case, the digital instruction generation unit may generate digital instructions based on information collected by the doctor when diagnosing a patient. Also, the digital instruction generation unit may generate digital instructions based on the information received from the patient. For example, the information received from the patient may include the patient's basal factors, medical information, and digital therapeutics literacy. In this case, the basal factors may include amount of the patient's activity, heart rates, sleep, meals (nutrition and calories), and the like. The medical information may include the patient's electronic medical record (EMR), family history, genetic vulnerability, genetic susceptibility, and the like. The digital therapeutics literacy may include the patient's accessibility and an acceptance posture to the digital therapy instructions and the apparatus, and the like.

The digital instruction generation unit generates digital instructions particularly designed to allow a patient to have a therapeutic effect, and provides the instructions to the patient. For example, the digital instruction generation unit may generate specific digital instructions in each of digital therapeutic modules, such as exercise and VNS modules described herein.

The outcome analysis unit may collect the patient's behavior adherence or participation in predetermined periods and report the patient's behavior adherence or participation to external systems. Therefore, a doctor may continue to monitor an execution course of the digital instructions through the application even when a patient does not directly visit a hospital.

The database may store information related to maintaining, optimizing strengthening an immune system of a subject, such as the therapeutic hypothesis for maintaining, optimizing strengthening an immune system of a subject, the digital instructions provided to the user, and the user's execution outcome data. The database can be included in the digital apparatus for treating maintaining, optimizing strengthening an immune system of a subject. However, the database may be provided in an external server.

A session may comprise any number of digital therapeutic modules (e.g., VNS modules and/or exercise modules). In some embodiments, a session may comprise two or more digital therapeutic modules. In some embodiments, a session may comprise 3 or more, 4 or more, 5 or more, 6 or more, 7 or more, 8 or more, 9 or more, 10 or more, 11 or more, 12 or more, 13 or more, 14 or more, 15 or more, 20 or more, or 25 or more digital therapeutic modules. A session may comprise any number of digital therapeutic modules, and the digital therapeutic modules may be independently selected from vagal nerve stimulation module and an exercise module. A session can be repeated as frequently or as infrequently as needed. In some embodiments, a session can be repeated 5 times per day, 4 times per day, 3 times per day, 2 times per day, daily, every 2 days, every 3 days, every 4 days, every 5 days, every 6 days, every 7 days, every 2 weeks, every 3 weeks, or every 4 weeks.

Figure 16:
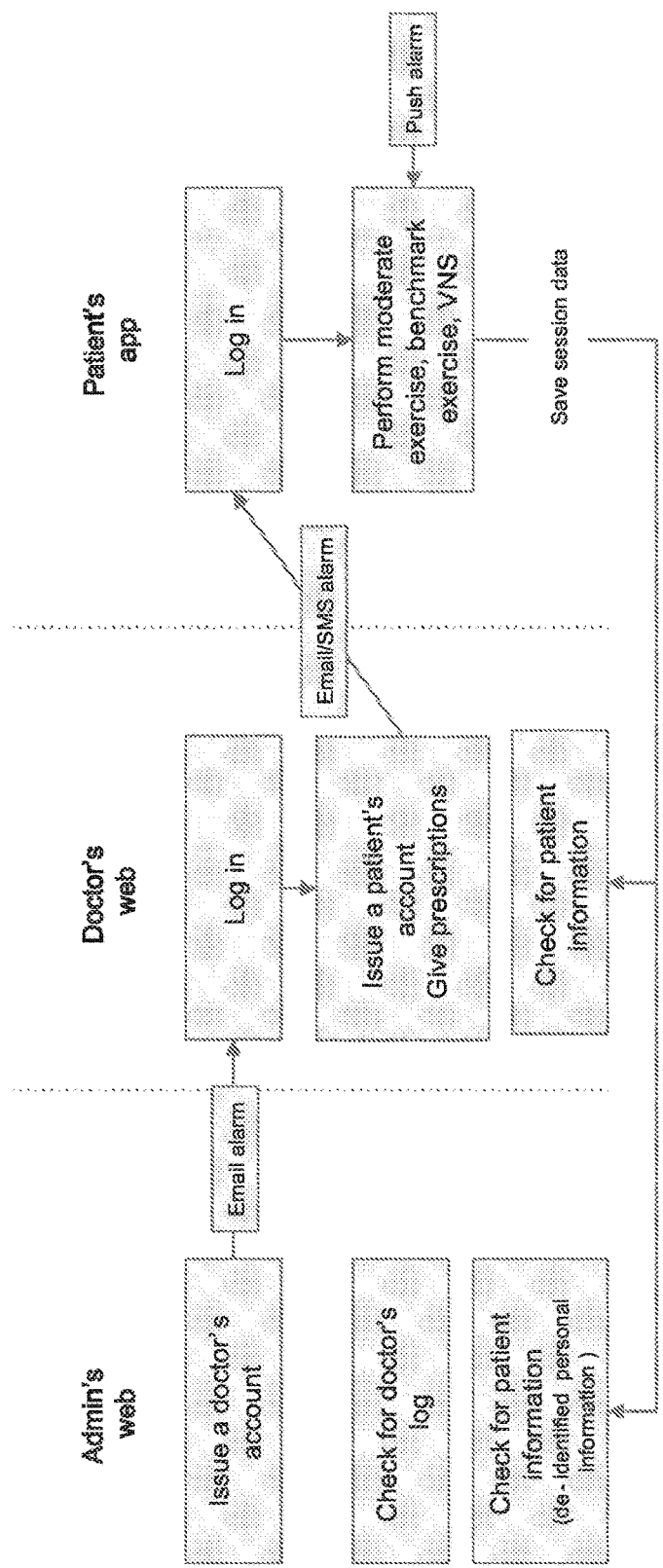
FIG. 16 illustrates a flow chart of an exemplary system for maintaining, optimizing, or strengthening an immune system of a subject, the system comprising an administrative portal (e.g., Administrator's web), a healthcare provider portal (e.g., Doctor's web) and a digital apparatus configured to execute a digital application (e.g., an application or 'app') for maintaining, optimizing, or strengthening an immune system of a subject.
Figure 17:
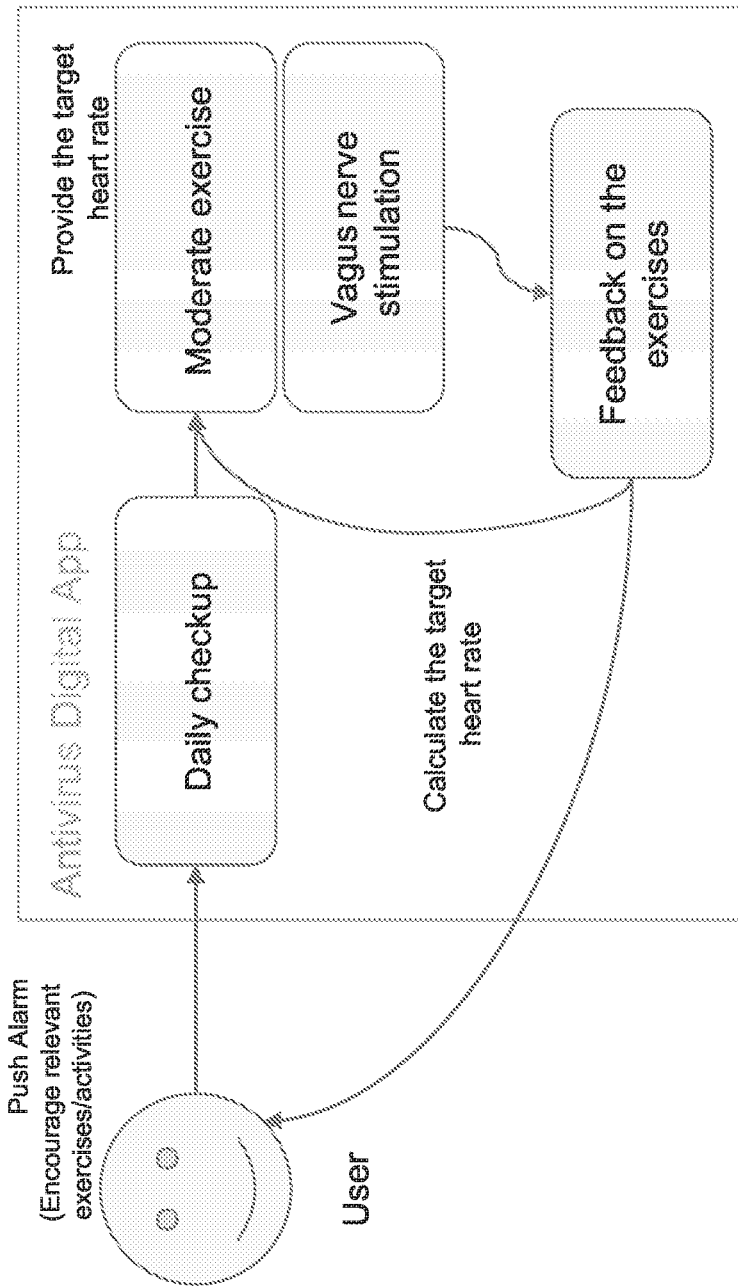
FIG. 17 illustrates a flow chart of service for a digital application of the present disclosure.
Figure 18:
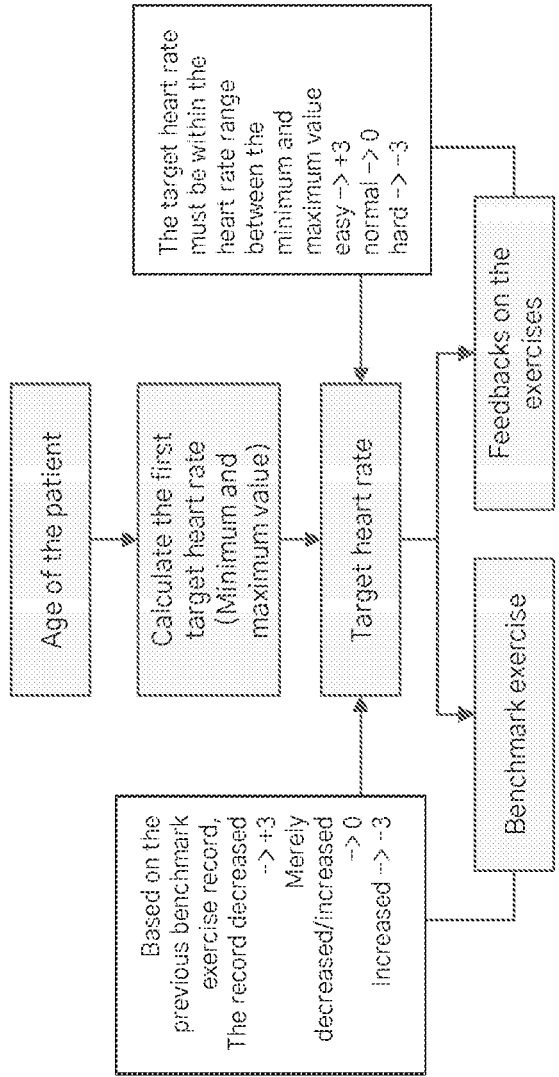
FIG. 18 illustrates a flow chart of an exemplary methods for determining target heart rate for a subject.
Figure 19:
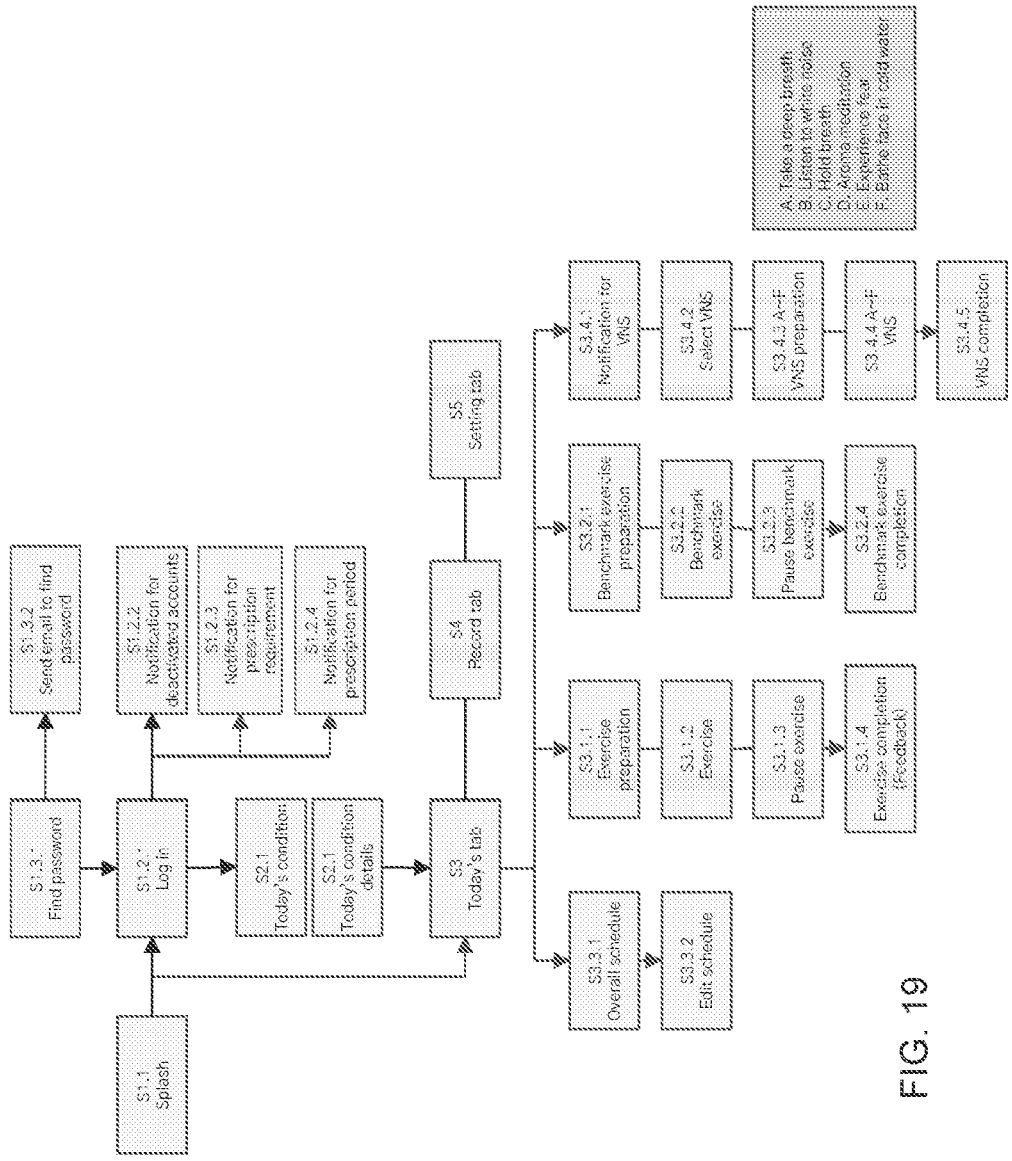
FIG. 19 illustrates a flow chart of an exemplary execution flow for a digital application of the present disclosure.
Figure 20:
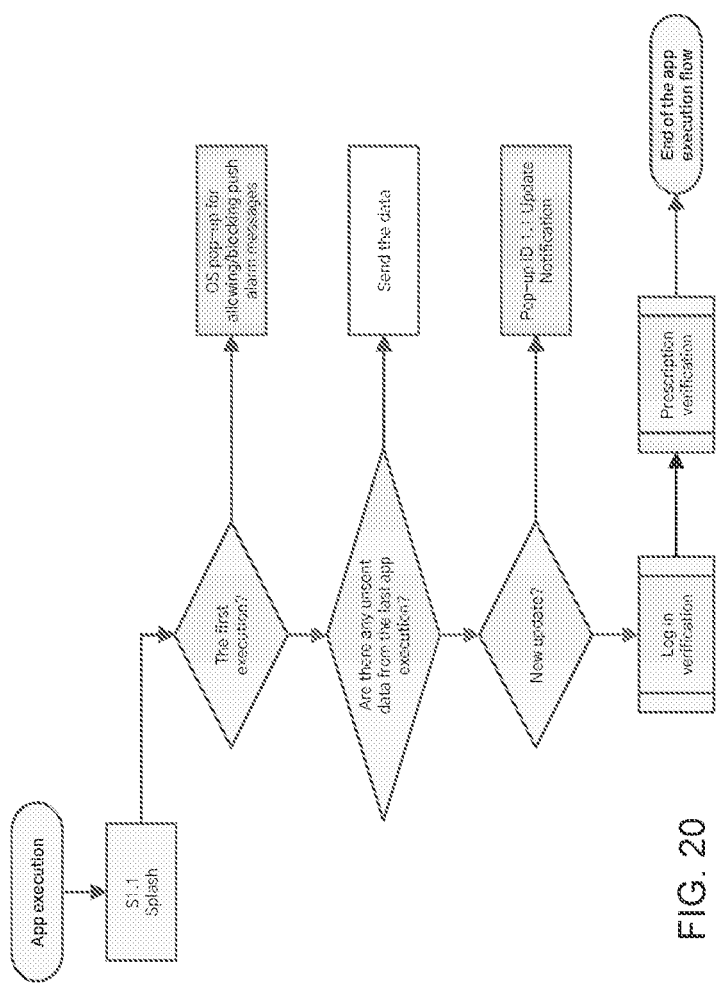
FIG. 20 illustrates a flow chart of service for a digital application of the present disclosure.

FIG. 16 depicts a flow chart illustrating a system for treating maintaining, optimizing strengthening an immune system of a subject, the system comprising an administrative portal (e.g., Administrator's web), a healthcare provider portal (e.g., Doctor's web) and a digital apparatus configured to execute a digital application (e.g., an application or 'app') for treating maintaining, optimizing strengthening an immune system of a subject in a subject. Among other things, the Administrator's portal allows an administrator to issue doctor accounts, review doctor information, and review de-identified patient information. Among other things, the Healthcare Provider's portal allows a healthcare provider (e.g., a doctor) to issue patient accounts, and review patient information (e.g., age, prescription information, and status for having completed one or more digital therapeutic modules or sessions). Among other things, the digital application allows a patent access to complete one or more digital therapeutic modules or sessions.

Figure 21B:
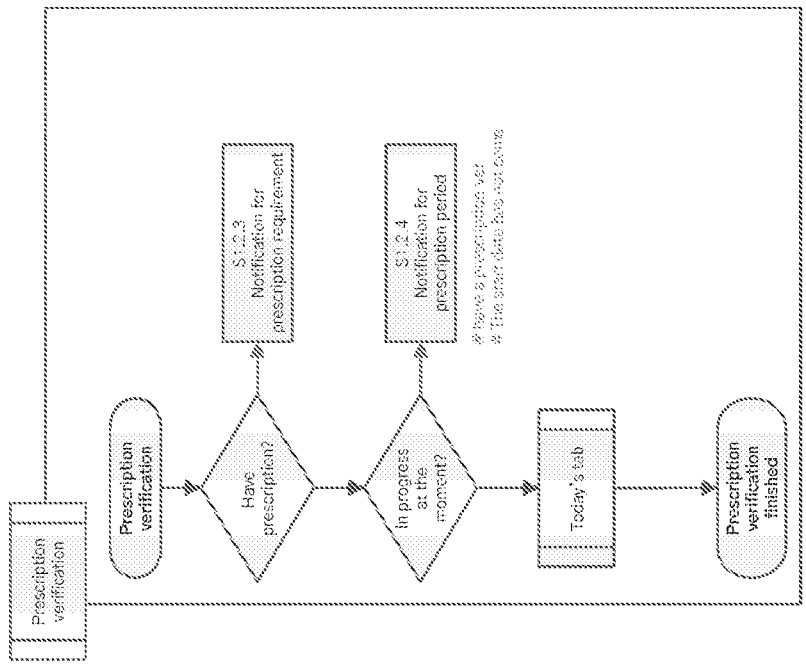
FIGS. 21A AND 21B illustrate an exemplary execution flow for a login verification during a splash process at the starting of a digital application of the present disclosure, and an exemplary execution flow for a prescription verification during a splash process at the starting of a digital application of the present disclosure, respectively.
Figure 21A:
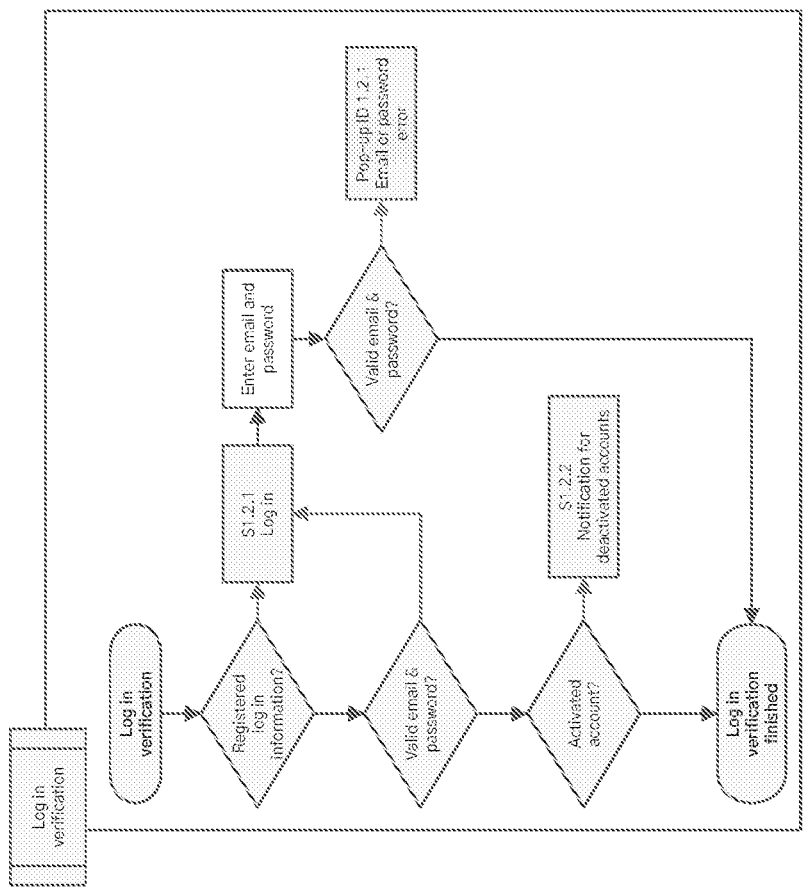
Figure 22:
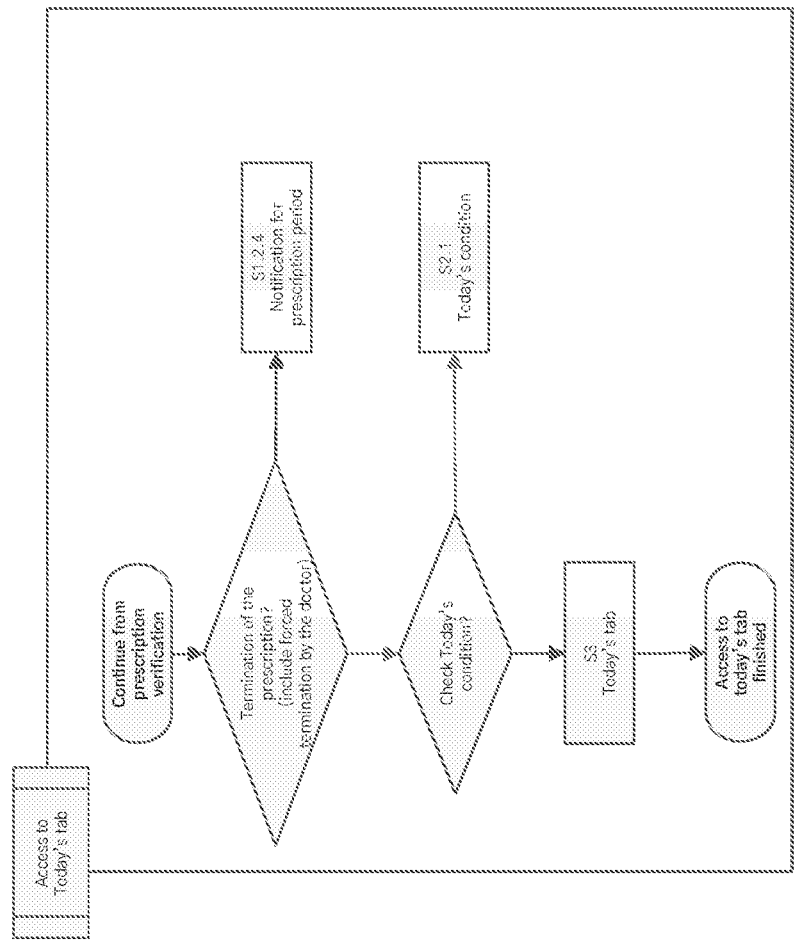
FIG. 22 illustrates an exemplary flow chart for a digital application of the present disclosure.
Figure 23:
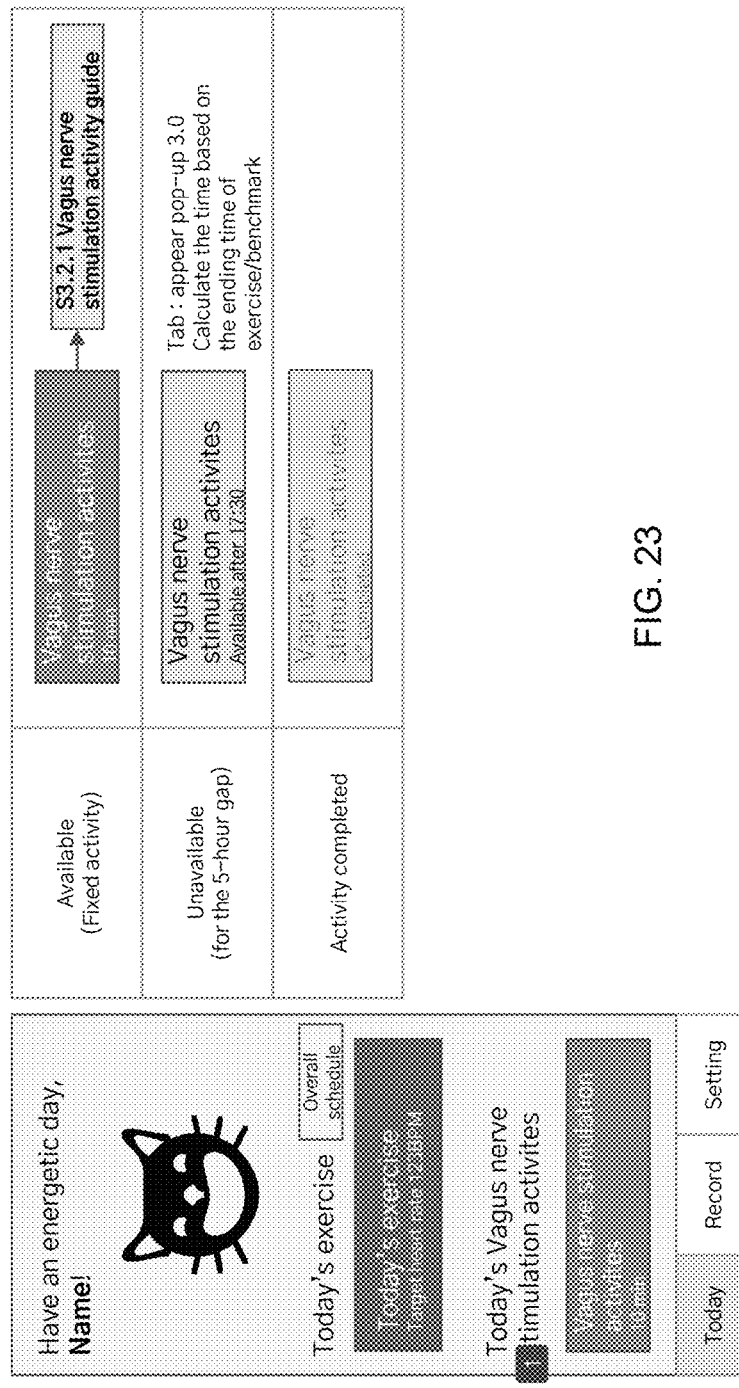
FIG. 23 illustrates an exemplary display of the daily modules to be performed by the subject.
Figure 24:
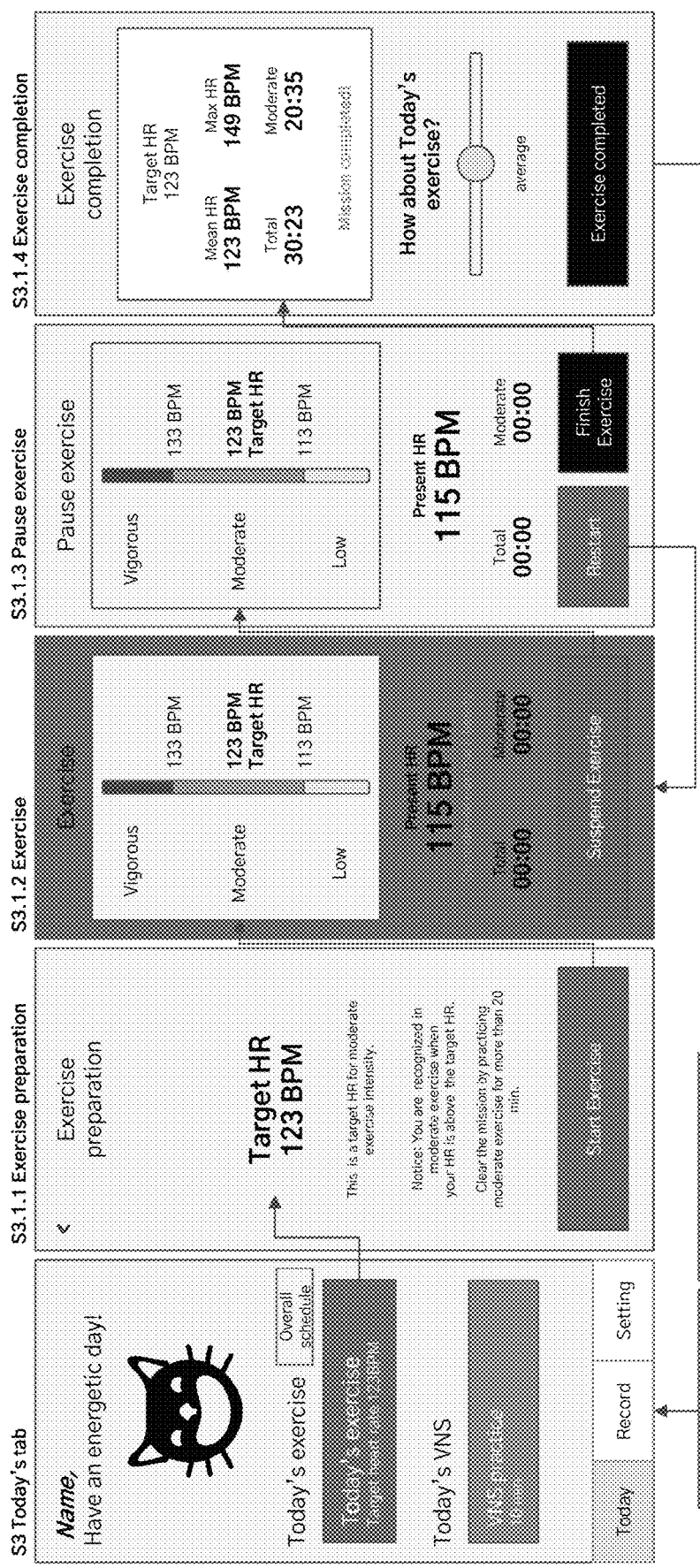
FIG. 24 illustrates exemplary series of displays within a moderate exercise module, including a display for exercise preparation, exercise, pausing the exercise, and exercise completion.
Figure 25:
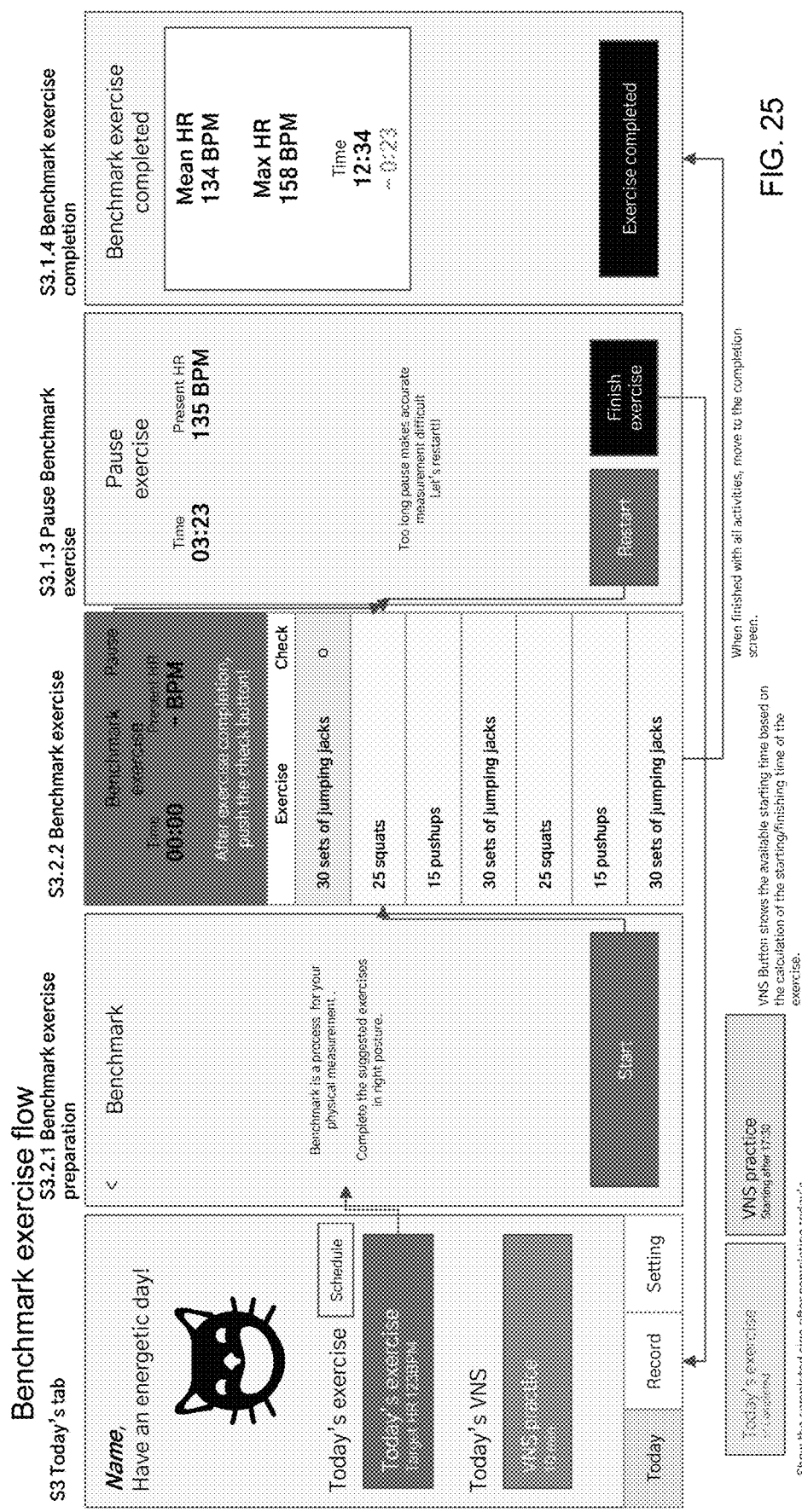
FIG. 25 illustrates an exemplary series of displays within a exercise module, including a display for benchmark exercise preparation, benchmark exercise, pausing the benchmark exercise, and benchmark exercise completion.
Figure 26:
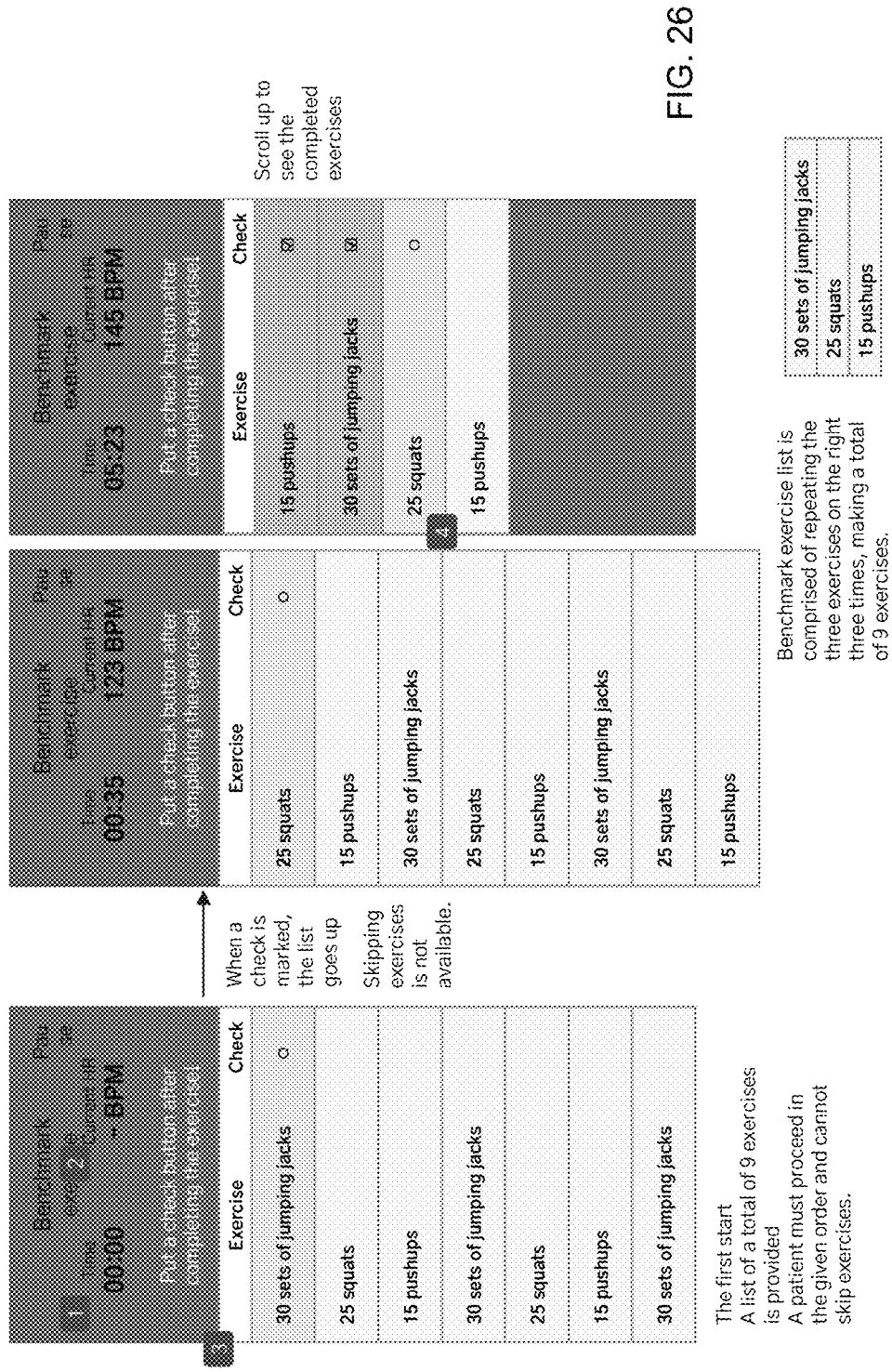
FIG. 26 illustrates an exemplary benchmark exercise display within an exercise module.
Figure 27:
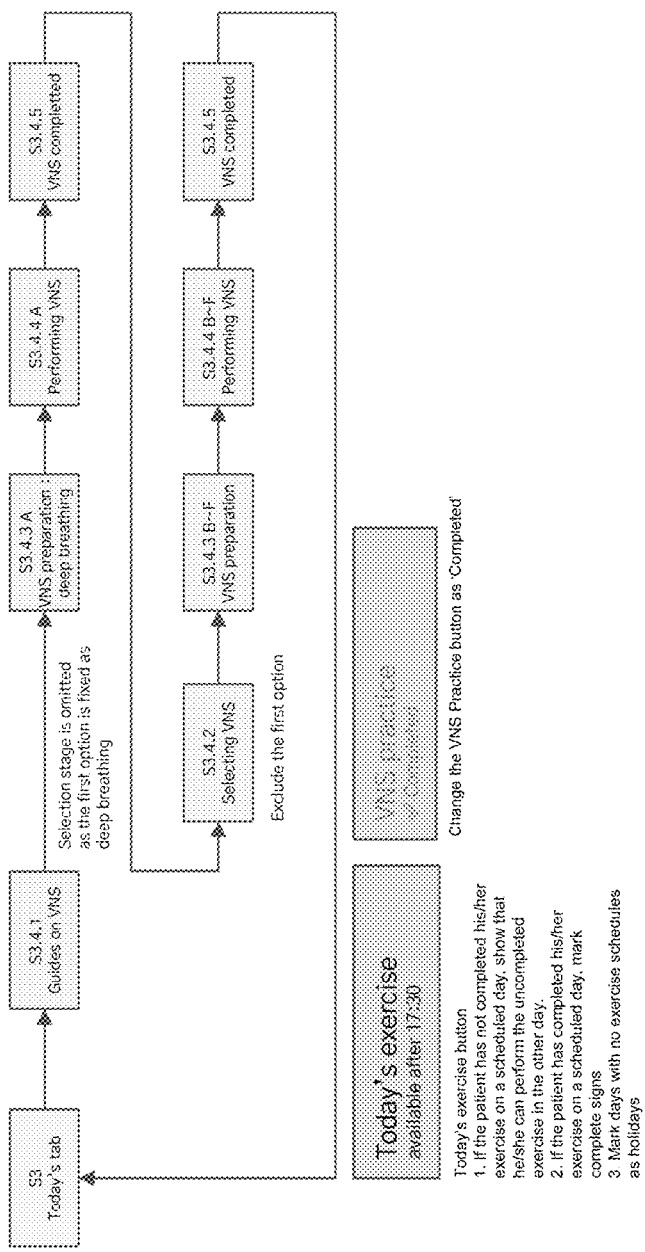
FIG. 27 illustrates a flow chart of an exemplary VNS workflow.
Figure 28:
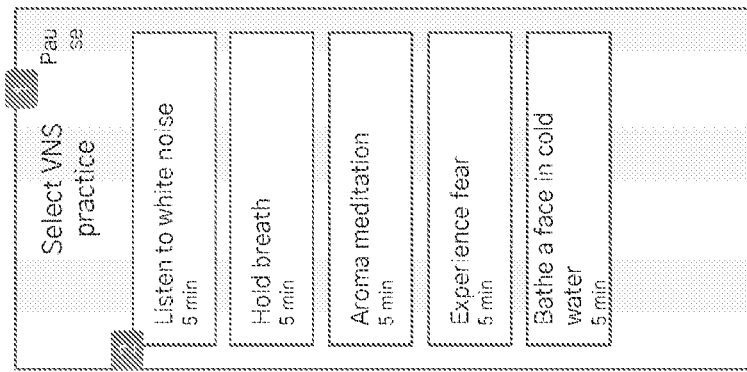
FIG. 28 illustrates an exemplary display showing different types of VNS module available for the subject to perform, including listening to white noise, holding the subject's breath, aroma meditation, experiencing fear, and bathing the subject's face in cold water.
Figure 29:
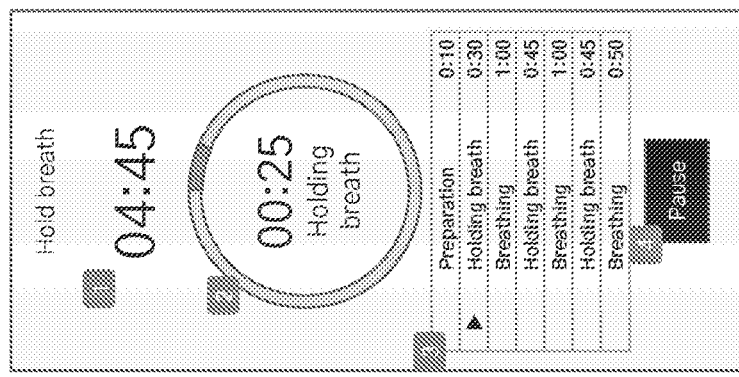
FIG. 29 illustrates exemplary display for a VNS module including holding the subject's breath.
Figure 30:
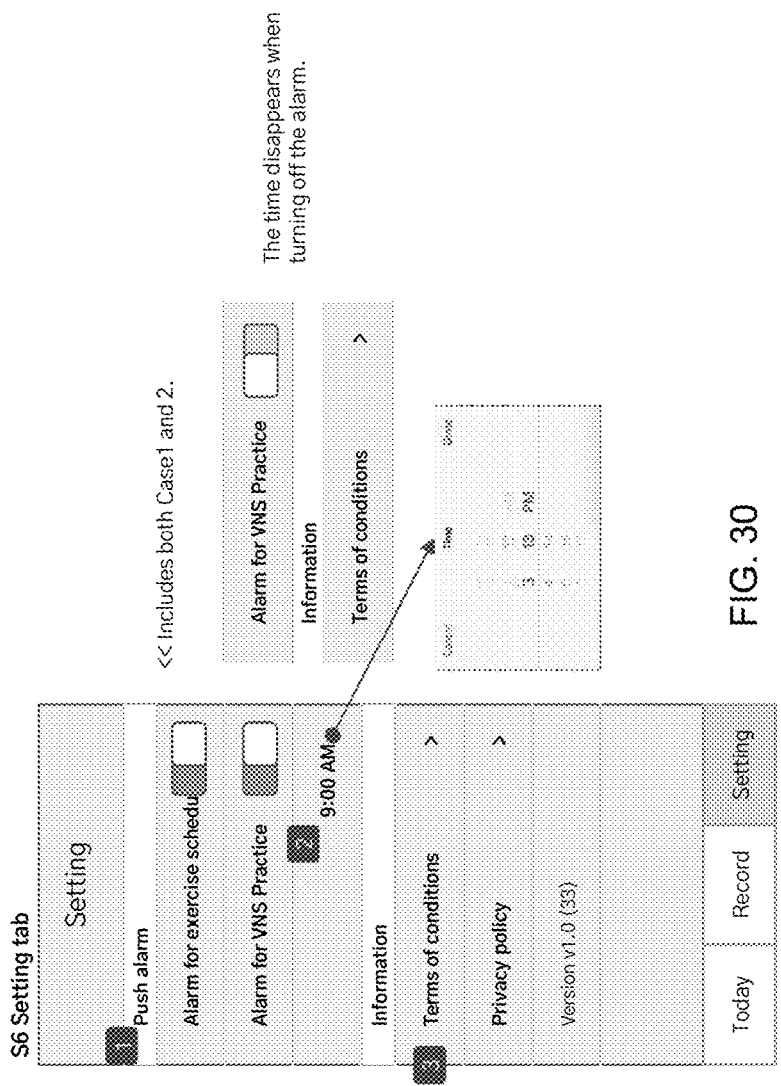
FIG. 30 illustrates an exemplary display showing a settings panel within the digital application, including options, for example, to adjust the time and/or date, turn on/off push alarms, and viewing terms and conditions.
Figure 31:
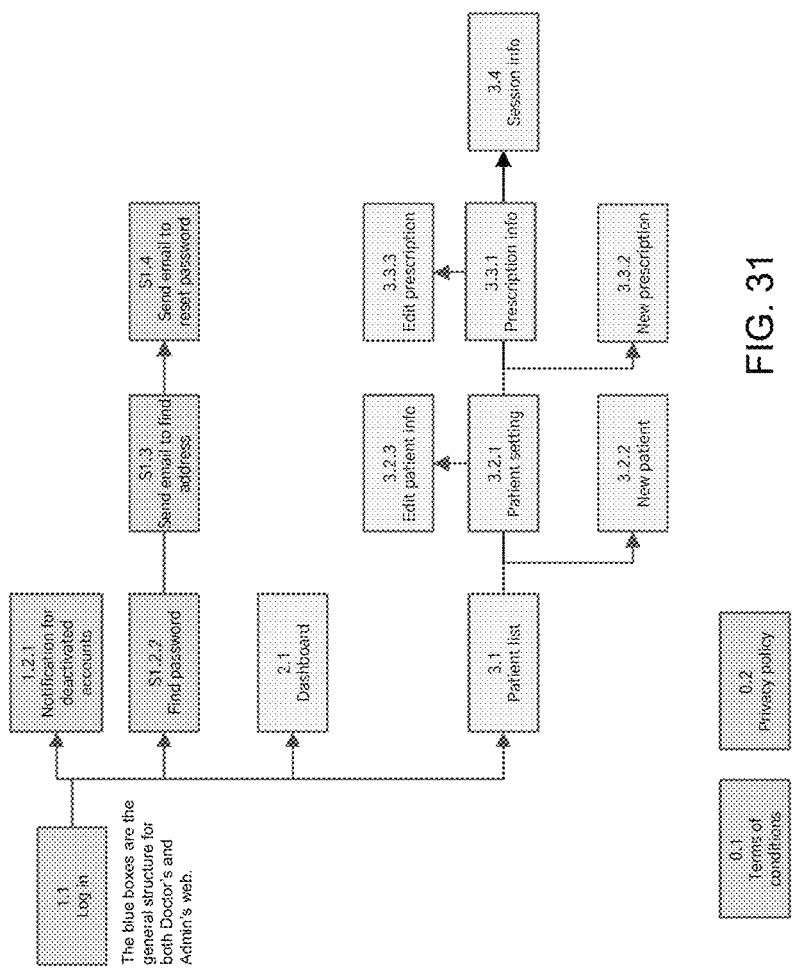
FIG. 31 illustrates an exemplary execution flow for a healthcare provider portal in a system of the present disclosure.

FIG. 21A depicts a flow chart illustrating an execution flow for login verification during a splash process at the starting of the digital application. Similarly, FIG. 21B also depicts a flow chart illustrating an execution flow for prescription verification during a splash process at the starting of the digital application. The prescription verification process may comprise, for example, determining if the treatment period has expired, determining whether the subject has been recently (e.g., within the last hour) performed a VNS module), determining if, based on the prescription, the subject's sessions for the day have been completed (e.g., the subject is compliant with the prescription). In such instances, the digital apparatus may notify the subject that there are no sessions available to be completed.

In some embodiments, the healthcare provider portal provides a healthcare provider with one or more options, and the one or more options provided to the healthcare provider are selected from the group consisting of adding or removing the subject, viewing or editing personal information for the subject, viewing adherence information for the subject, viewing a result of the subject for one or more at least partially completed digital therapeutic modules, prescribing one or more digital therapeutic modules to the subject, altering a prescription for one or more digital therapeutic modules, and communicating with the subject. In some embodiments, the one or more options comprise the viewing or editing personal information for the subject, and the personal information comprises one or more selected from the group consisting of an identification number for the subject, a name of the subject, a date of birth of the subject, an email of the subject, an email of the guardian of the subject, a contact phone number for the subject, a prescription for the subject, and one or more notes made by the healthcare provider about the subject. In some embodiments, the personal information comprises the prescription for the subject, and the prescription for the subject comprises one or more selected from the group consisting of a prescription identification number, a prescription type, a start date, a duration, a completion date, a number of scheduled or prescribed digital therapeutic modules to be performed by the subject, and a number of scheduled or prescribed digital therapeutic modules to be performed by the subject per day. In some embodiments, the one or more options comprise the viewing the adherence information, and the adherence information of the subject comprises one or more of a number of scheduled or prescribed digital therapeutic modules completed by the subject, and a calendar identifying one or more days on which the subject completed, partially completed, or did not complete one or more scheduled or prescribed digital therapeutic modules. In some embodiments, the one or more options comprise the viewing the result of the subject, and the result of the subject for one or more at least partially completed digital therapeutic modules comprises one or more selected from the group consisting of a time at which the subject started a scheduled or prescribed digital therapeutic module, a time at which the subject ended a scheduled or prescribed digital therapeutic module, and an indicator of whether the scheduled or prescribed digital therapeutic module was fully or partially completed.

Figure 32:
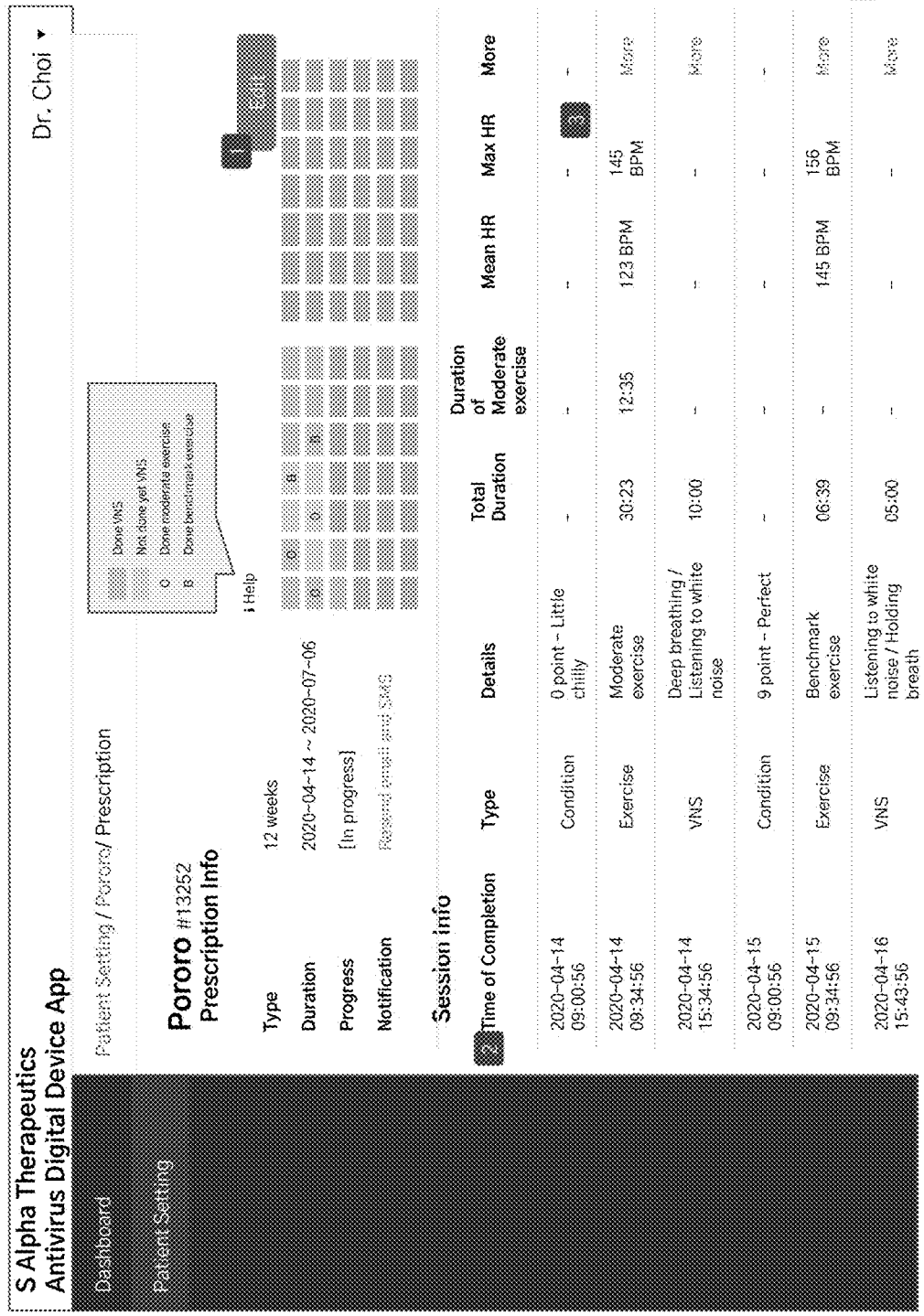
FIG. 32 illustrates an exemplary patient tab in a healthcare provider portal that displays detailed prescription information for a given patient.
Figure 33:
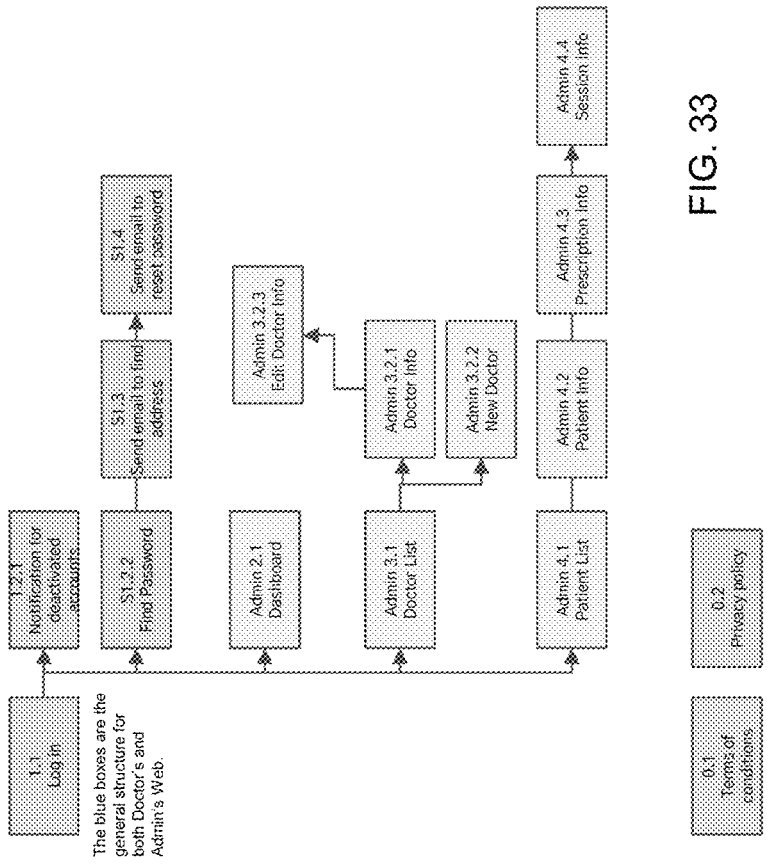
FIG. 33 illustrates a flow chart of an exemplary execution flow for an administrative portal in a system of the present disclosure.
Figure 34:
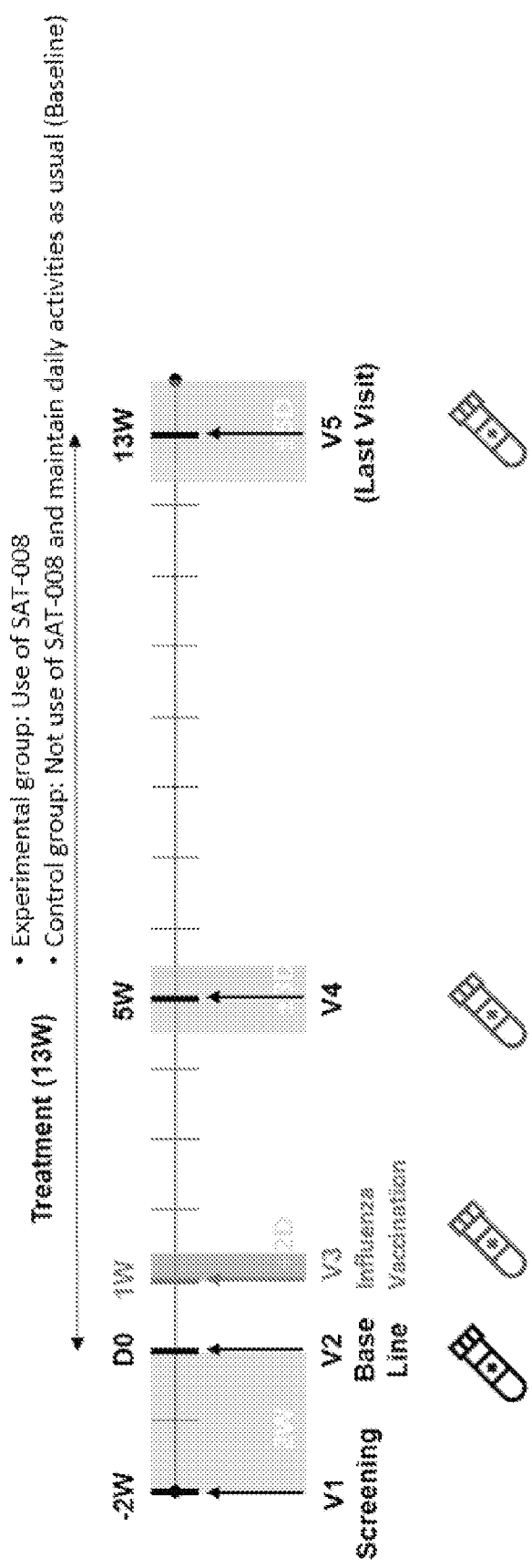
FIG. 34 illustrates an exemplary timeline guide for the clinical trial test.

A dashboard of a healthcare provider portal displays the number of all patients associated with the present doctor's account. A graph may be used to show the number of patients who have opened the digital application for patient per day in the most recent 90 days. The number of patients in progress may also be viewed. A graph may be used to show the number of patients who have completed the daily sessions per day in the most recent 90 days. A patient tab in a healthcare provider portal includes (1) Patient ID (the unique identification number temporarily given to each patient when adding them on the list), (2) Patient Name, (3) Search bar for searching by ID, Name, Email, Memo, etc., and (4) Add New Patient button for adding new patients. A patient tab in a healthcare provider portal displays (1) detailed patient information, (2) a button for editing patient information, (3) prescription information, (4) a button for adding a new prescription, (5) a progress status for different each prescription, and (6) a button or link for sending an email to the patient. A patient tab in a healthcare provider portal for adding a new patient displays (1) a button for adding a new patient, and (3) an error message displayed when required patient information has not been provided. A patient tab in a healthcare provider portal for editing information of an existing patient includes (1) is a button or link for resetting a password, (2) is a button for deleting a given patient, and (3) is a button for saving changes. FIG. 32 depicts a patient tab in a healthcare provider portal that displays detailed prescription information for a given patient. As shown, (1) is a button for editing prescription information, (2) displays the duration of the sessions attended by the patient or subject, and (3) shows an overview the treatment progress. Seven days are represented as a line or row of 7 squares. For 12 weeks, each 6 weeks may be presented separately. Different colors may be used to discern session statuses (e.g., grey for sessions not started, red for sessions not attended, yellow for sessions partially attended, and green for sessions fully attended). In some embodiments, the administrative portal provides an administrator with one or more options, and the one or more options provided to the administrator of the system are selected from the group consisting of adding or removing the healthcare provider, viewing or editing personal information for the healthcare provider, viewing or editing de-identified information of the subject, viewing adherence information for the subject, viewing a result of the subject for one or more at least partially completed digital therapeutic modules, and communicating with the healthcare provider. In some embodiments, the one or more options comprise the viewing or editing the personal information, and the personal information of the healthcare provider comprises one or more selected from the group consisting of an identification number for the healthcare provider, a name of the healthcare provider, an email of the healthcare provider, and a contact phone number for the healthcare provider. In some embodiments, the one or more options comprise the viewing or editing the de-identified information of the subject, and the de-identified information of the subject comprises one or more selected from the group consisting of an identification number for the subject, and the healthcare provider for the subject. In some embodiments, the one or more options comprise the viewing the adherence information for the subject, and the adherence information of the subject comprises one or more of a number of scheduled or prescribed digital therapeutic modules completed by the subject, and a calendar identifying one or more days on which the subject completed, partially completed, or did not complete one or more scheduled or prescribed digital therapeutic modules. In some embodiments, the one or more options comprise the viewing the result of the subject, and the result of the subject for one or more at least partially completed digital therapeutic modules comprises one or more selected from the group consisting of a time at which the subject started a scheduled or prescribed digital therapeutic module, a time at which the subject ended a scheduled or prescribed digital therapeutic module, and an indicator of whether the scheduled or prescribed digital therapeutic module was fully or partially completed.

A dashboard of an administrative portal shows (1) the number of doctors. A graph may be used to show the number of doctors that have visited the digital application per day in the most recent 90 days, (2) the number of all patients associated with the any doctor's account. A graph may be used to show the number of patients who have opened the digital application for patient per day in the most recent 90 days. The number of patients in progress may also be viewed. A graph may be used to show the number of patients who have completed the daily sessions per day in the most recent 90 days. A doctor tab in an administrative portal displays a list of doctors. The doctor tab further displays (1) a search bar for searching for various doctors by name, email, etc., (2) a button for adding a new doctor, (3) the doctor's ID, (4) a button for viewing detailed doctor information, and (5) deactivated doctor accounts. A doctor tab in an administrative portal displays a list of patients being cared for by a given doctor, with patient-identifying information redacted (*). The doctor tab further displays the doctor's account information, (2) a button for editing the doctor's account information, (3) a list of patients being cared for by the doctor, (4) a list of patient ID numbers, (5) a link or button for sending the doctor a registration email, (6) a notification that the doctor's account has been deactivated, which only appears for deactivated accounts, and (7 and 8) redacted or de-identified patient information.

With respect to certain embodiments of the present disclosure, only patients who have been prescribed by a healthcare provider can use the digital application. A patient can visit the doctor in order to be prescribed. The can doctor provide prescriptions on an n-week basis, where 'n' can be any number. The data of the patient's application can be accessed via the healthcare provider or administrative portal. In certain embodiments, a patient can perform exercises for 2-3 times a week and VNS for 10 minutes every day. In certain embodiments, 5~6 hours of time gap is required between the exercise and VNS. Generally, exercise can refer to performing aerobic exercises at a moderate level. Schedules for the exercises can be suggested based on the heart rate data measured during prior exercises via a wearable device (smart watch). In certain embodiments, mart watches that automatically connect with the health kit of the given platform (iOS, Android) can be used. Push alarms can be used to remind the patient of his/her schedule to perform exercises and VNS.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs). A processor in association with software may be used to implement a radio frequency transceiver for use in a WTRU, UE, terminal, base station, RNC, or any host computer.

In one aspect, the present disclosure also relates to a non-transitory computer readable medium having stored thereon software instructions for maintaining, optimizing, or strengthening an immune system of a subject in need thereof that, when executed by a processor, cause the processor to: display, by an electronic device to the subject, a first exercise module and/or a first vagal nerve stimulation module, each of the first modules comprising instructions for the subject to follow; sense, by a sensor in the electronic device, adherence by the subject to the instructions of the first modules; transmit, by the electronic device, adherence information, based on the adherence, to a server; receive, from the server, one or more second instructions based on the adherence information; and display, to the subject, a second exercise module and/or a second Vagal nerve stimulation module, the second modules comprising the one or more second instructions. In some embodiments, the digital application for maintaining, optimizing, or strengthening an immune system instructs a processor of the digital apparatus to execute operations comprising: generating digital therapeutic modules for maintaining, optimizing, or strengthening an immune system based on age and/or target heart rate.

In one aspect, the present disclose relates to the following embodiments.

The present disclosure relates to a method for use in an apparatus to provide antiviral digital immunity (ADI), the method comprising: generating an antiviral digital vaccine (ADV) that comprises one or more digital instructions causing a user's immune system at least one of natural killer (NK) cell recruitment, T cell boosting, or vagal nerve stimulation (VNS); and providing the one or more digital instructions via the apparatus.

The one or more digital instructions related to the NK cell recruitment may comprise vigorous exercise, moderate exercise and light exercise. The method may further comprise: determining a level of the vigorous exercise, the moderate exercise or the light exercise based on at least one of a heart rate (HR), a repetition maximum (RM), metabolic equivalents (METs), a maximal oxygen uptake capacity ($VO_{2max}$)/oxygen uptake reverse ($VO_2R$), or a rating of perceived exertion (RPE).

In some embodiments, the one or more digital instructions related to the T cell boosting comprise aerobic exercise and acute exercise. The method may further comprising: determining a level of the aerobic exercise or the acute exercise based on at least one of a HR, a RM, METs, a $VO_{2max}$/$VO_2R$, or a RPE.

In some embodiments, the one or more digital instructions related to the VNS comprise at least one of visual, auditory, tactual, gustatory, or olfactory stimulation that increases sIgA secretion.

In some embodiments, the method may further comprise: receiving a result of a user's performance on the one or more digital instructions; and generating, based on the result, a second ADV that comprises one or more digital instructions causing the user's immune system at least one of NK cell recruitment, T cell boosting, or VNS. In further embodiments, the user's performance on the one or more digital instructions is repeated predetermined multiple times.

The present disclosure relates to an apparatus to provide antiviral digital immunity (ADI), the apparatus comprising: a processor configured to: generate an antiviral digital vaccine (ADV) that comprises one or more digital instructions causing a user's immune system at least one of natural killer (NK) cell recruitment, T cell boosting, or vagal nerve stimulation (VNS); and provide the one or more digital instructions via the apparatus. In some embodiments, the one or more digital instructions related to the NK cell recruitment comprise vigorous exercise, moderate exercise and light exercise. In further embodiments, the processor is further configured to determine a level of the vigorous exercise, moderate exercise or the light exercise based on at least one of a heart rate (HR), a repetition maximum (RM), metabolic equivalents (METs), a maximal oxygen uptake capacity ($VO_{2max}$)/oxygen uptake reverse ($VO_2R$), or a rating of perceived exertion (RPE). In additional embodiments, the one or more digital instructions related to the T cell boosting comprise aerobic exercise and acute exercise. In yet further embodiments, the processor is further configured to determine a level of the aerobic exercise or the acute exercise based on at least one of a HR, a RM, METs, a $VO_{2max}$/$VO_2R$, or a RPE. In yet additional embodiments, the one or more digital instructions related to the VNS comprise at least one of visual, auditory, tactual, gustatory, or olfactory stimulation that increases sIgA secretion. In some embodiments, the processor is further configured to: receive a result of a user's performance on the one or more digital instructions; and generate, based on the result, a second ADV that comprises one or more digital instructions causing the user's immune system at least one of NK cell recruitment, T cell boosting, or VNS. In some embodiments, the user's performance on the one or more digital instructions is repeated predetermined multiple times.

The present disclosure relates to a method for providing a subject with antiviral digital immunity (ADI) using an antiviral digital vaccine (ADV), the method comprising: administering, by the subject, the ADV that comprises one or more digital instructions causing the subject's immune system at least one of natural killer (NK) cell recruitment, T cell boosting, or vagal nerve stimulation (VNS). In some embodiments, the one or more digital instructions related to the NK cell recruitment comprise vigorous exercise, moderate exercise and light exercise. In further embodiments, the one or more digital instructions related to the T cell boosting comprise aerobic exercise and acute exercise. In additional embodiments, the one or more digital instructions related to the VNS comprise at least one of visual, auditory, tactual, gustatory, or olfactory stimulation that increases sIgA secretion.

EXAMPLES

Example 1: Clinical Trial to Evaluate the Efficacy, Safety and Feasibility of a Method and Device of the Present Disclosure in Healthy Adults A single-center, randomized, open label, no-treatment controlled, medical device clinical trial was conducted to evaluate the efficacy, safety and feasibility in healthy adults aged 19 to under 45.

The selection criteria were: 1) healthy adult male and female aged 19 to 45; 2) person who received influenza vaccination the previous year; 3) those who are scheduled to receive influenza vaccine; 4) a person who is judged to be suitable as a subject based on the judgment of the investigator through the screening test (clinical findings, medical history, vital signs, body mass index, physical examination, laboratory test); 5) those who do not exercise regularly: as a result of physical activity evaluation using the International Physical Activity Questionnaires (IPAQ), persons who are under low intensity activity (does not correspond to IPAQ 2 or 3, or physical activity less than 600 MET-min/week); 6) for women of childbearing age, those who have agreed to avoid pregnancy or use appropriate contraceptive methods during the clinical trial period; for men, those who have agreed to use appropriate contraceptive methods during the clinical trial period; 7) a person who understands this clinical trial and is able to participate in good faith and agrees to abide by the restrictions; 8) those who agreed to collect blood during the visit and study period for follow-up; 9) A person who voluntarily agrees to participate in this clinical trial and the subject has voluntarily signed a written consent; and 10) those who have a smartphone and can use the application independently using the smartphone.

The exclusion criteria were those who have infectious disease (HIV, HBV, HCV) test results being positive, those who have uncontrolled diabetes (HbA1c 6.5% or more, or fasting (8 hours or more) plasma glucose 126 mg/dL or more), those who have a history of tumor, and those who have a history of autoimmune diseases. The exclusion criteria further includes: those with neurological, circulatory, respiratory, liver or kidney disease (excluding controlled hypertension (systolic/diastolic blood pressure less than 140/90 mmHg)), a person who has behavioral, cognitive, or mental illness that affects the understanding and compliance of the clinical trial protocol when judged by the investigator, persons with a history of acute infectious diseases, those who had fever exceeding 37.5° C. in body temperature within 1 month before screening, prior to screening, those who have immunosuppressants, immunomodulators, immunoglobulins, blood-derived agents, or other drugs that may affect immunity, as determined by the investigator, such as those who received an immunosuppressant within 2 months prior to screening or who intend to administer it during the clinical trial period, those who received an immunomodulator within 6 months prior to screening, and those who have received immunoglobulins or blood-derived products within 3 months prior to screening. In addition, the exclusion criteria include: those who received a live vaccine within 28 days prior to screening, persons who received killed vaccines within 14 days before screening, those who are taking medications not approved by the investigator, a person with a history of alcohol or drug abuse affecting participation in the clinical trial, people who are currently smoking, pregnant and lactating women, those who have applied/administered medical devices/drugs for other clinical trial within 6 months prior to screening or plan to apply/administer them during the trial period, a person who is judged to be unsuitable for participation in a clinical trial by the investigator.

The overall clinical trial period was 12 months after approval of the clinical trial protocol of each institution IRB (however, the clinical trial period was changed depending on the registration status). The clinical trial period for each subject was about 29 weeks. There were two groups for the trial: test group was screened for 4 weeks, medical device treated for 13 weeks (including vaccination) and followed-up in 12 weeks based on medical device termination; and control group was screened for 4 weeks, no medical device treated (maintained the same daily life as before clinical participation) for 13 weeks (including vaccination), and followed-up for in 12 weeks (based on medical device termination).

The first set target heart rate changes given the feedbacks on the exercises include: Easy>+3 BPM; Normal>0 BPM; Hard>−3 BPM. Records of weekly benchmark exercise used to calculate and update the target heart rate as the following (the target heart rate is within the heart rate range between the minimum and maximum value)
  the record is decreased to 10 seconds or more >+3 BPM
  the record is decreased/increased to 0-10 seconds>0 BPM
  the record increased to 10 or more seconds>−3 BPM Schedules for the patient were provided to perform exercises (including both moderate and benchmark exercises) 2 or 3 times per week. Given the total duration of the prescription (e.g. 5 weeks) on odd weeks (e.g., week 1, 3, 5), moderate exercise was scheduled on day 2 and 4 (twice a week) on even weeks (e.g., week 2, 4), moderate exercise was scheduled on day 1 and 3, and benchmark exercise was scheduled on day 6 (three times a week). Patient can change the designed exercise schedule. Only the date of which the patient performs exercise can be changed (The total number of exercises designed for each week cannot be changed). The starting date of the prescription counts as the first day of the week.

Here, benchmark exercise aims to identify changes in the patient's stamina by making the patient repeatably perform a same set of exercise every once in two weeks. All kinds of exercises performed during this time are referred to as benchmark exercise. Benchmark exercise was scheduled on the last day of each week but was changed upon the patient's will. Based on the time record of weekly benchmark exercise, new target heart rate was calculated in the following way:
  The record decreased to 10 or more seconds>+3 BPM
  The record decreased/increased to 0-10 seconds>0 BPM
  The record increased to 10 or more seconds>3 BPM
*10 seconds and 3 BPM were used as arbitrary.

The clinical trial was designed as a single institution, open, controlled, and investigator-led medical device clinical trial to evaluate the efficacy, safety and feasibility of exemplary application in healthy. Thereafter, the test group continued to use the medical device for clinical trials for 12 weeks, and the control group maintained daily activities. Both groups visited the institute at 1 week (Visit 3), 5 weeks (Visit 4), and 13 weeks (Visit 5) from baseline time points for laboratory testing (including immunity indicator testing) and evaluation of quality of life questionnaire & safety (Including influenza symptom identification).

Drugs that may have a clinically significant effect on the immune system during the clinical trial were prohibited. Immunosuppressants, immunomodulators, immunoglobulins, blood-derived agents, or other drugs that may affect immunity, all vaccines other than influenza vaccine, and other drugs that were not approved by the investigator.

NK cell change amount for innate immunity evaluation at 1 week (V3), 5 weeks (V4), and 13 weeks (V5) was compared to baseline (primary efficacy endpoint). In the secondary efficacy endpoint, changes in the following indicators at 1, 5, and 13 weeks from baseline:
  CD4+ T cells, CD8+ T cells
  B cell
  Pro-inflammatory cytokines (IL-6, TNF-a and IL-1b), Anti-inflammatory cytokine (IL-10), IFN-γ

Primary efficacy endpoint: Descriptive statistics (mean, standard deviation, median, minimum, and maximum) for each NK cell result and change amount compared to baseline at 5 weeks after the application of clinical trial medical devices were presented by each group, and Paired t-test or Wilcoxon signed-rank test identified changes in each treatment group. To test for differences between groups, a covariance analysis with corrected baseline values was performed.

Secondary efficacy endpoint: NK cell change amount for innate immunity evaluation at 1, 13, and 25 weeks compared to baseline: After applying the medical device for clinical trials, descriptive statistics (average, standard deviation, median, minimum, maximum) for each NK cell result and amount of change at each time point compared to baseline at 1 week, 13 weeks, and 25 weeks were presented by group. In order to test for differences between groups, a covariance analysis with corrected base values was performed. Amount of change by immune indicator* at 1, 5, 13, and 25 weeks compared to baseline: For each indicator, descriptive statistics (average, standard deviation, median, minimum, maximum) for the results at 1 week, 5 weeks, 13 weeks, and 25 weeks after the application of the medical device for clinical trials and the amount of change at each time point compared to the baseline were presented by group. To test for differences between groups, a covariance analysis with corrected baseline values was performed. *CD4+ T cells, CD8+ T cells, B cell, Pro-inflammatory cytokines (IL-6, TNF-a and IL-1b), Anti-inflammatory cytokine (IL-10), IFN-γ. Whether antibodies are produced after vaccination against influenza: the percentage and frequency of subjects who produce antibodies after influenza vaccination at 5, 13, and 25 weeks were presented, and the percentage of antibody generated during the clinical trial period was presented by group. Chi-square test or Fisher's exact test was used to test for differences between groups. Expression and severity of upper respiratory tract infection symptoms: the frequency and rate of symptoms of upper respiratory tract infection at 1, 5, 13, and 25 weeks were presented, and the expression and severity of symptoms were presented by group. To test for differences between groups, a chi-square test or Fisher's exact test was performed. Compliance: descriptive statistics (average, standard deviation, median, minimum, and maximum) for the compliance of the test groups were presented. Questionnaire of quality of life at 1, 5, 13, and 25 weeks compared to the baseline (SF-36): Quality of life (SF-36) scores at 1 week, 5 weeks, 13 weeks, and 25 weeks after the application of clinical trial medical devices and descriptive statistics for changes in each time point compared to the baseline (average, standard deviation, median, minimum, Maximum values) were presented for each group. To test for differences between groups, a covariance analysis with corrected baseline values was performed.

Drugs that may have a clinically significant effect on the immune system during the clinical trial were prohibited. Immunosuppressants, immunomodulators, immunoglobulins, blood-derived agents, or other drugs that may affect immunity, all vaccines other than influenza vaccine, and other drugs that were not approved by the investigator.

To test the adherence rate, the following scene requirements were used.

Figure 35:
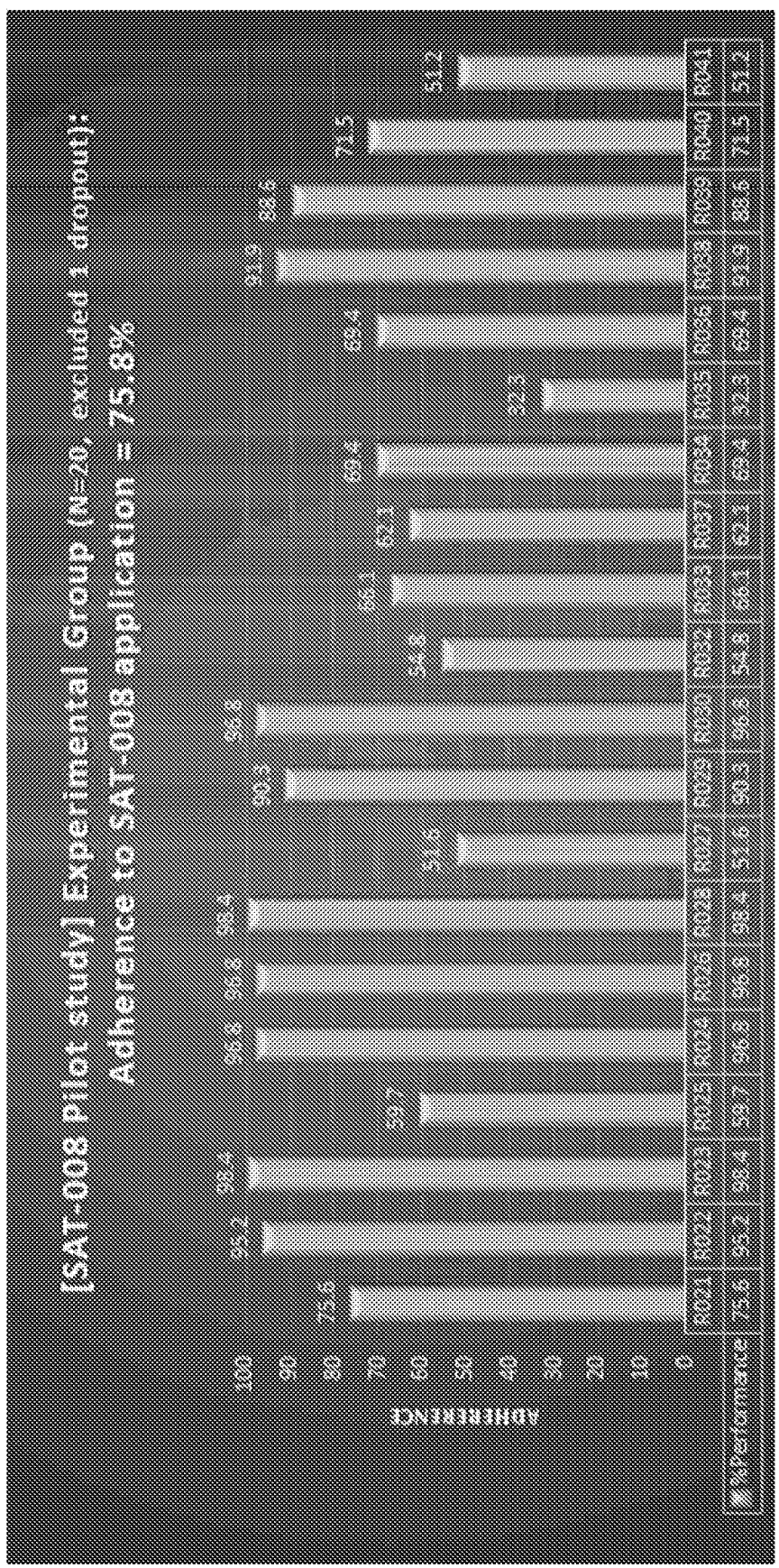
FIG. 35 is an exemplary graph illustrating an adherence rate of experimental group for an exemplary clinical trial test.
Figure 36:
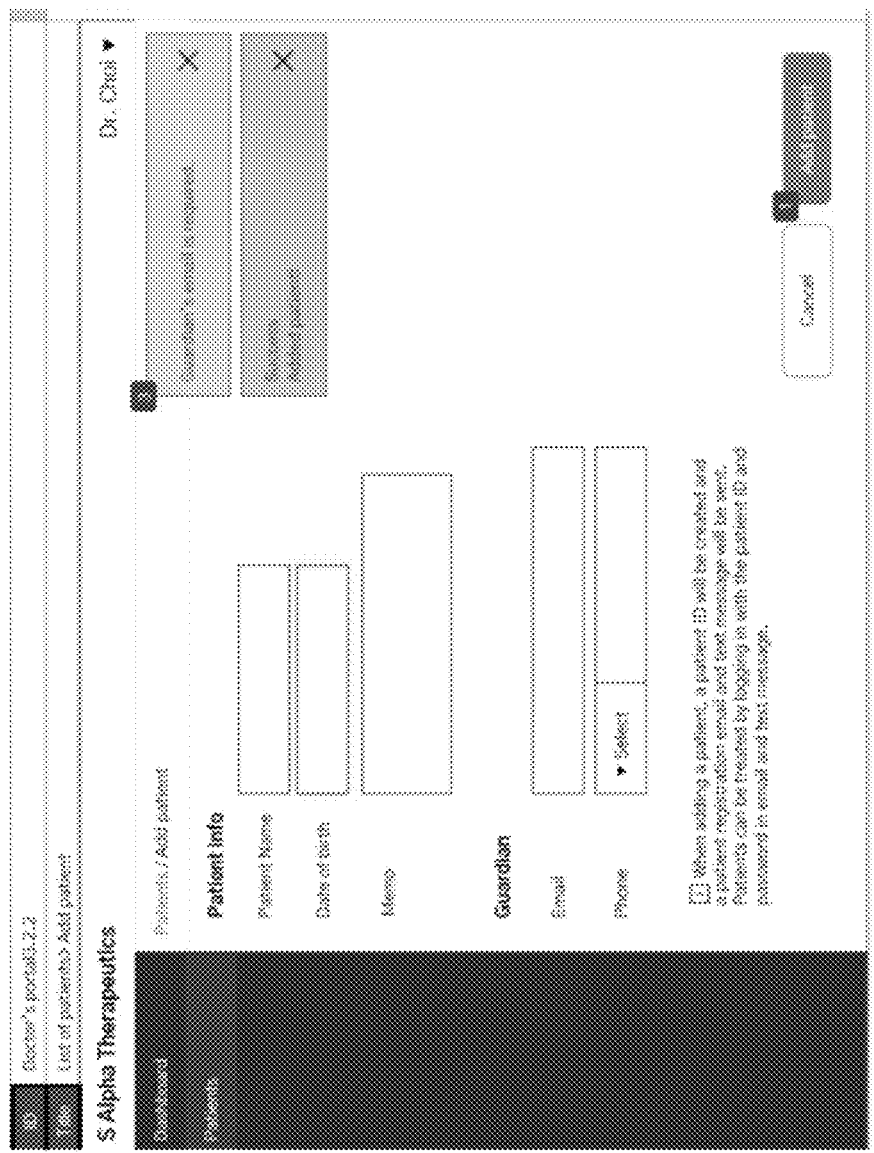
FIG. 36 illustrates an exemplary patient tab in a healthcare provider portal for adding a new patient.
Figure 37:
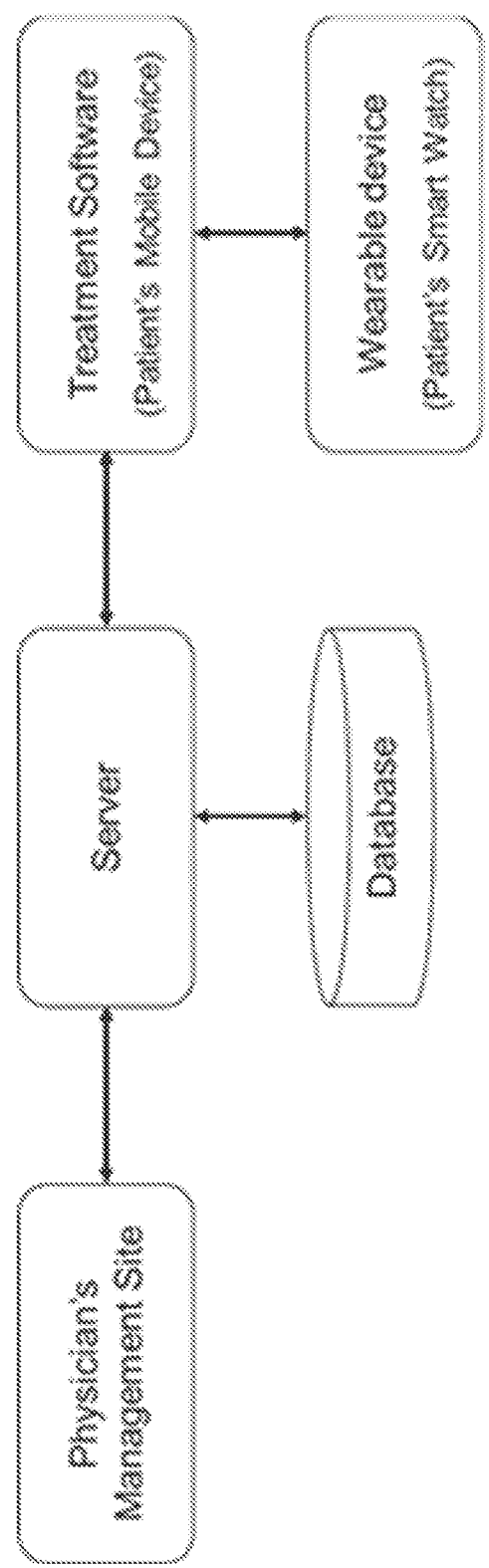
FIG. 37 illustrates a diagram of an exemplary product operating system.
Figure 38:
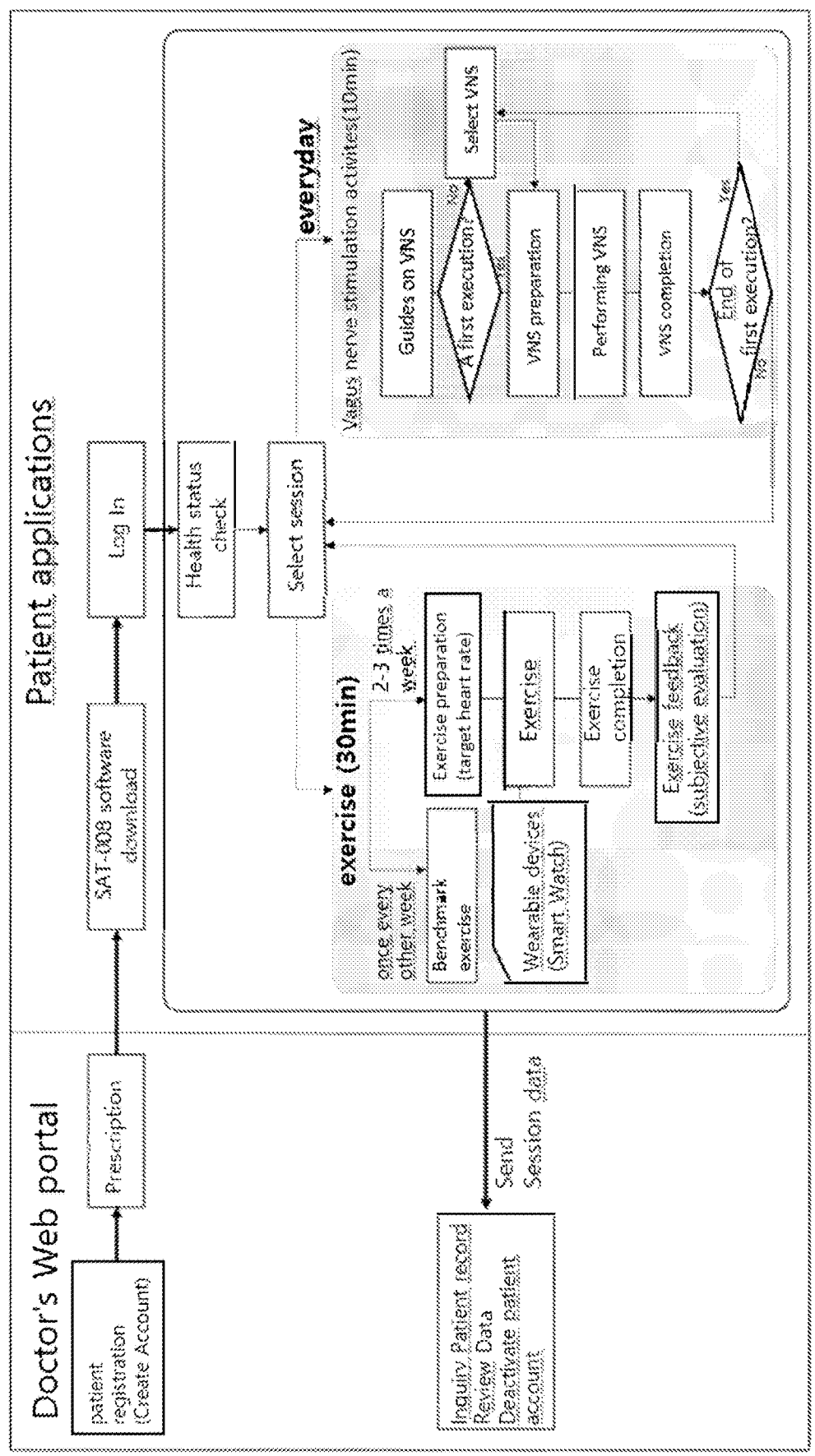
FIG. 38 illustrates an exemplary flow chart of an operation method for an exemplary clinical trial test.
Figure 39:
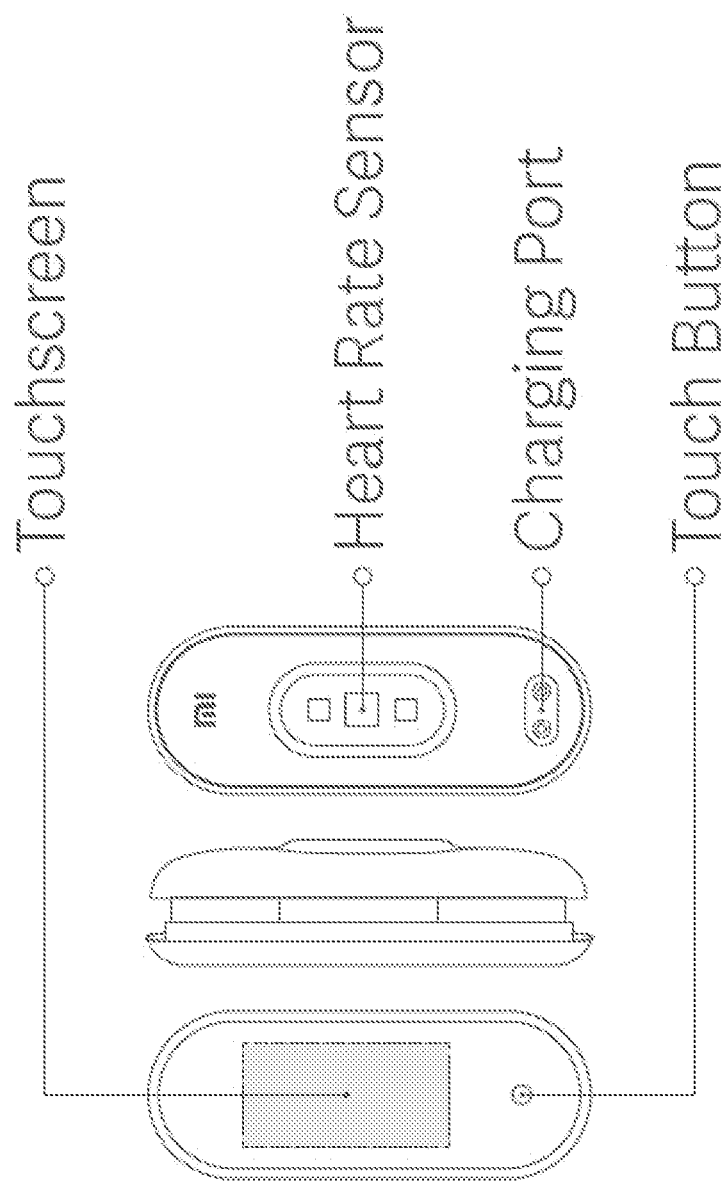
FIG. 39 illustrates an exemplary heart rate sensor.
Figure 40:
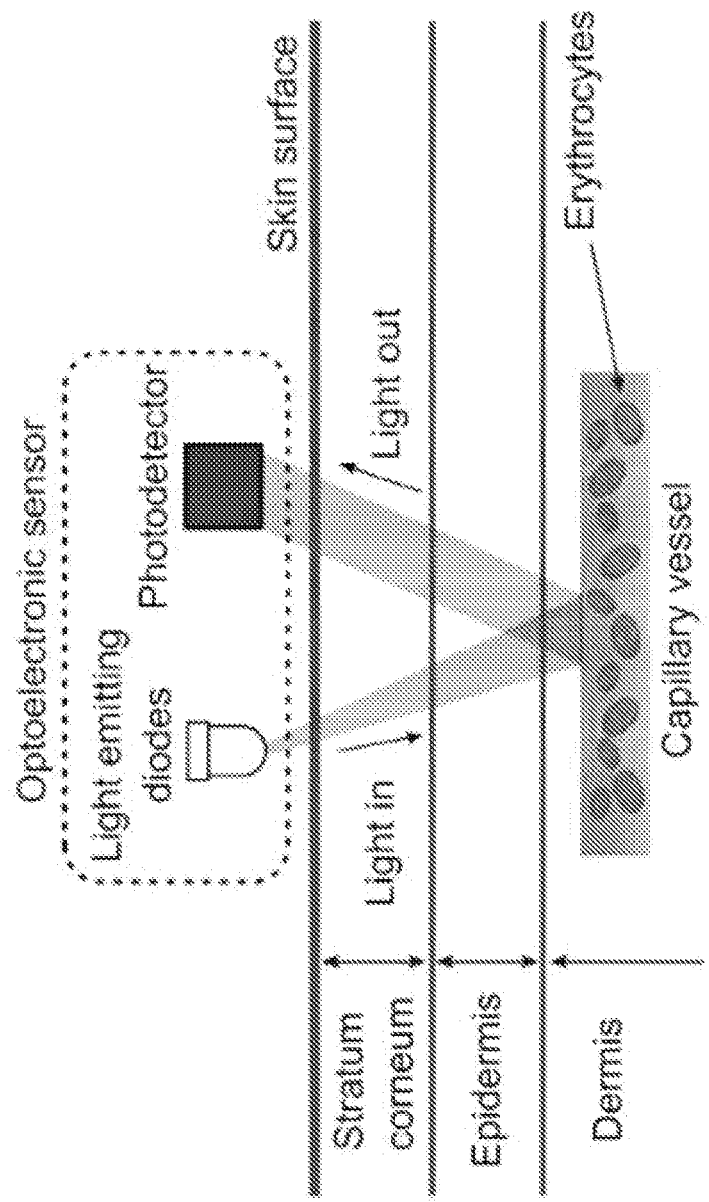
FIG. 40 illustrates an exemplary heart rate sensor is based on the principle of optical blood flow measurement.
Figure 41:
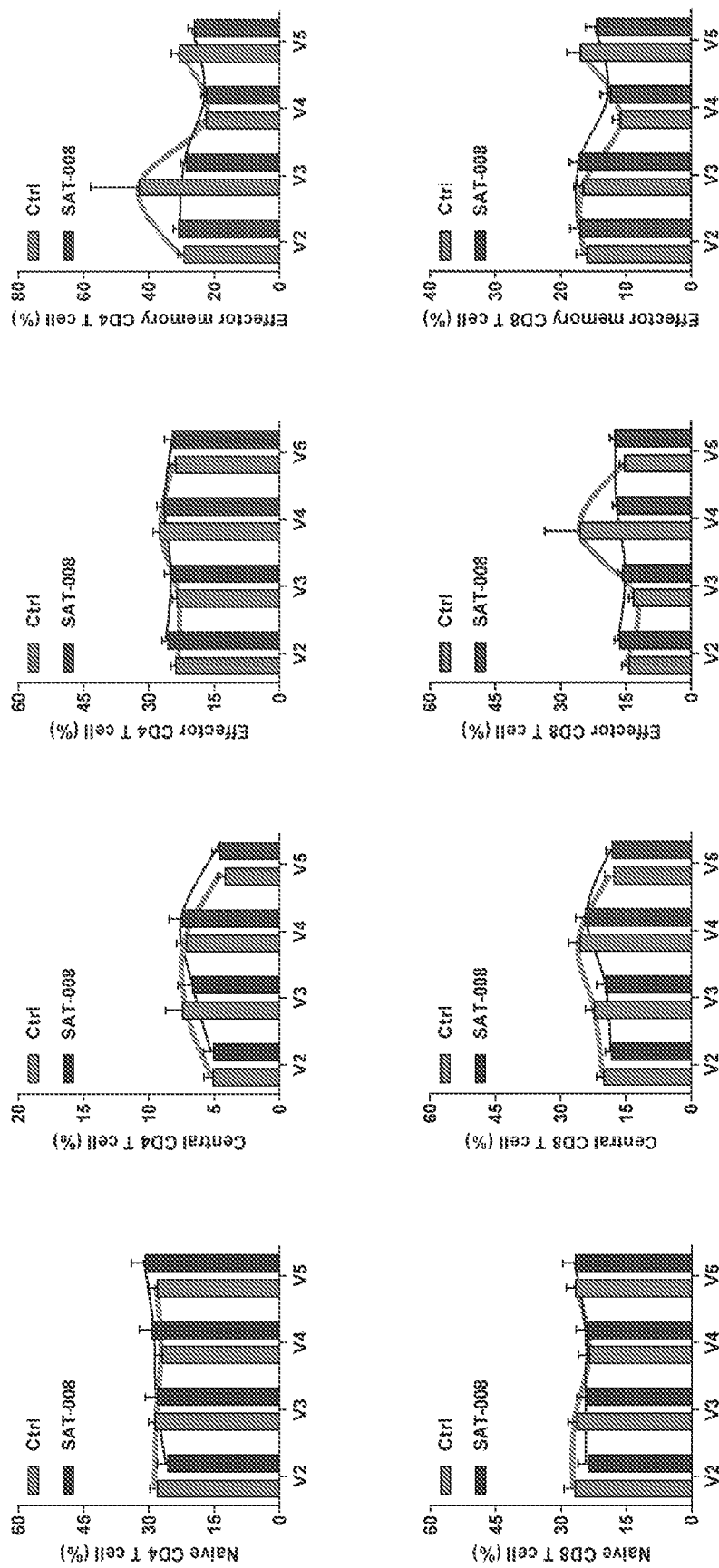
FIGS. 41-46 show graphs illustrating results of the exemplary clinical trial test.
Figure 42:
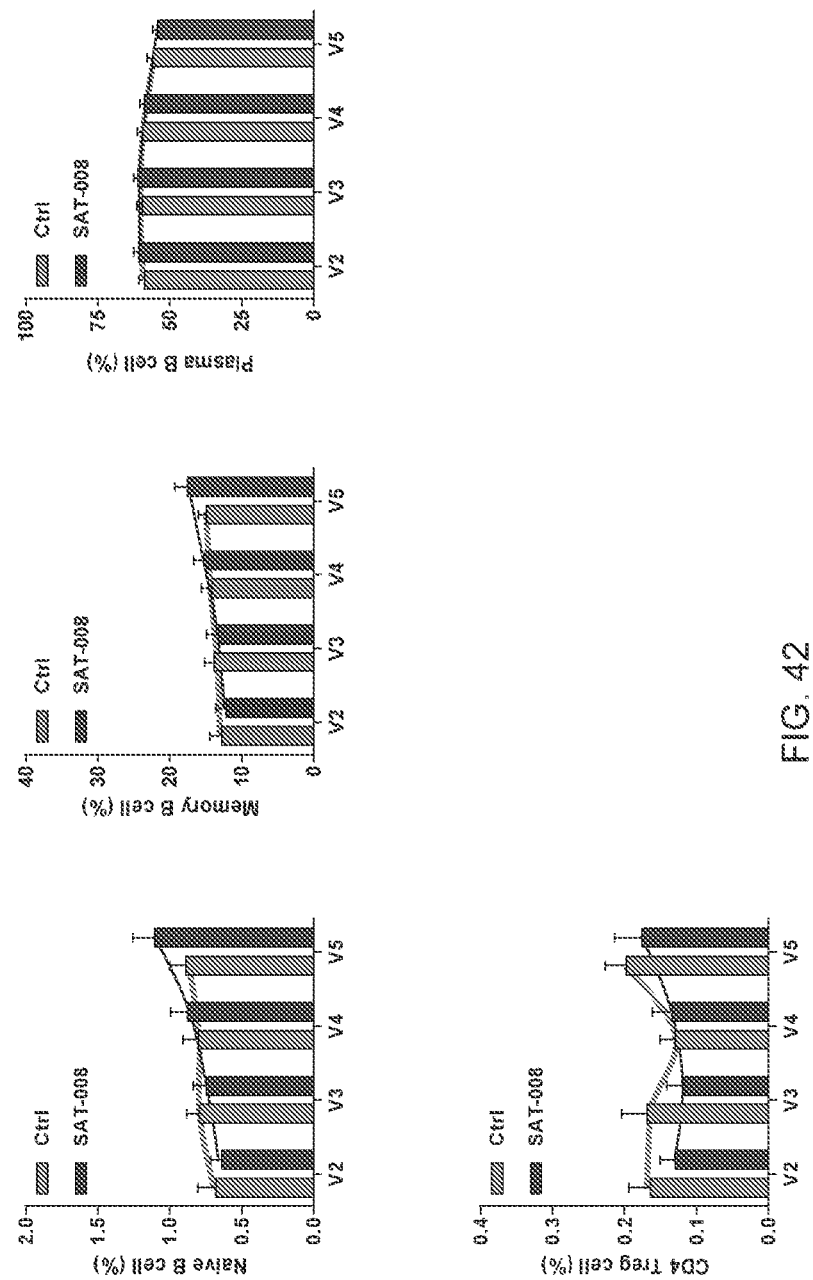
Figure 43:
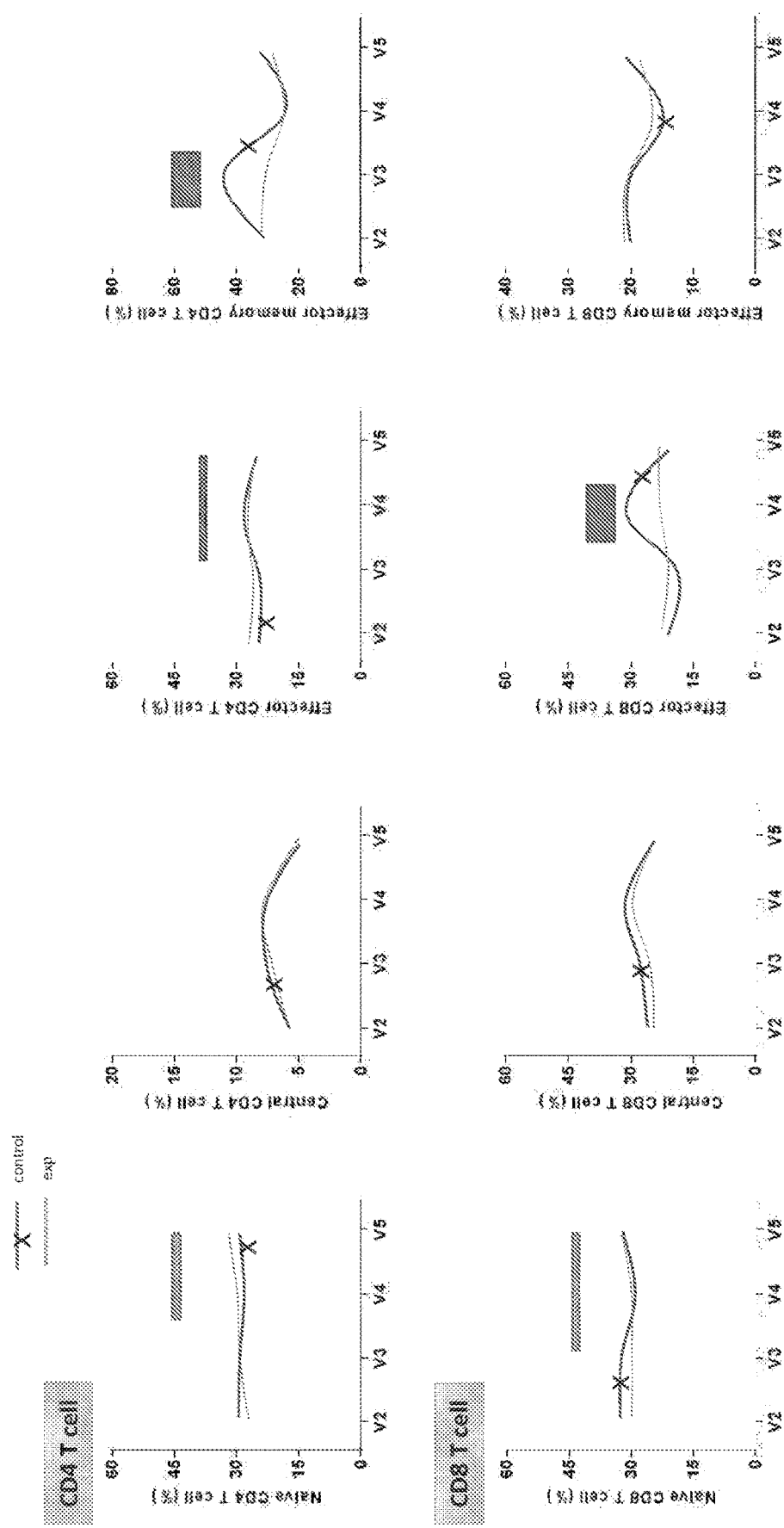
Figure 44:
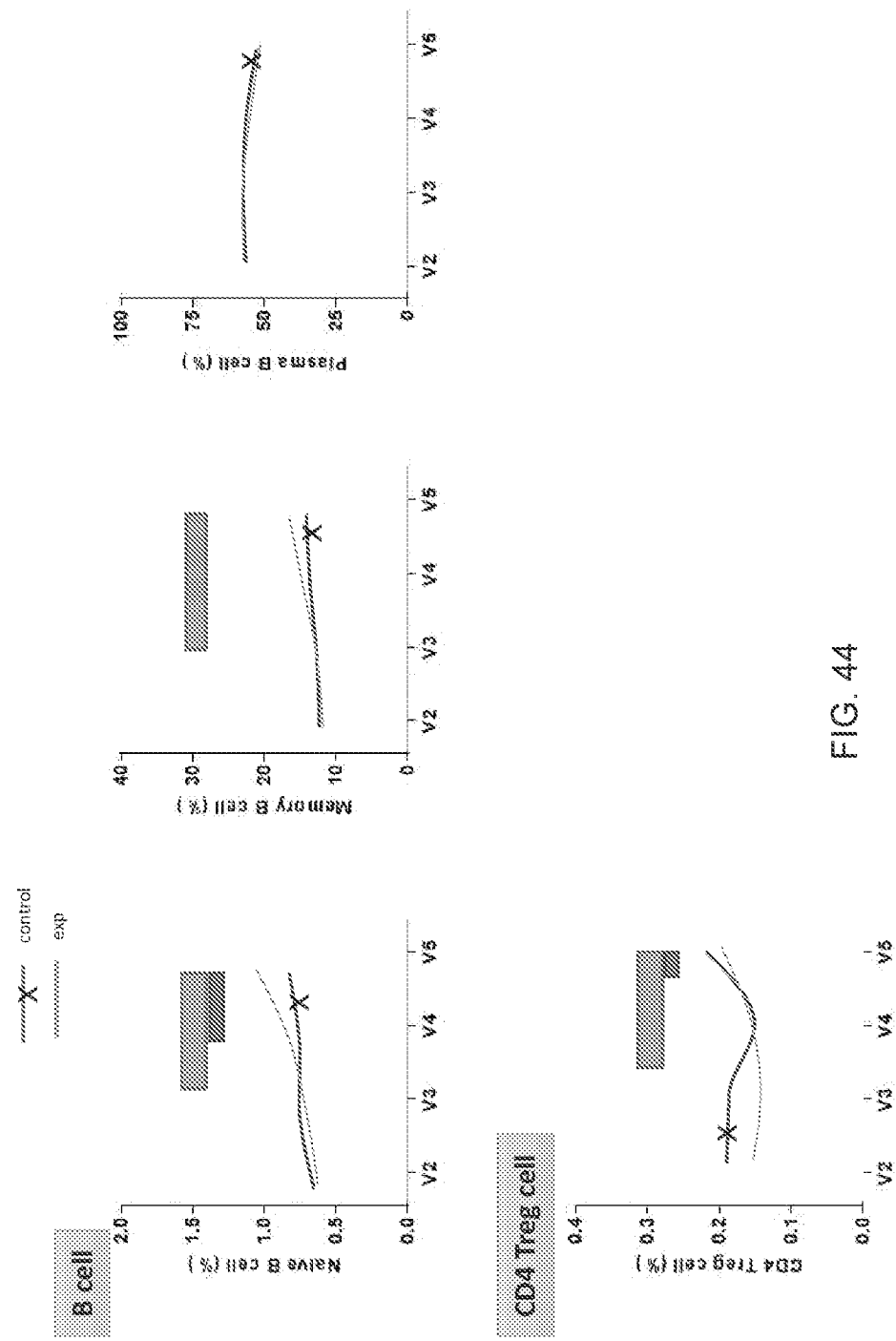
Figure 45:
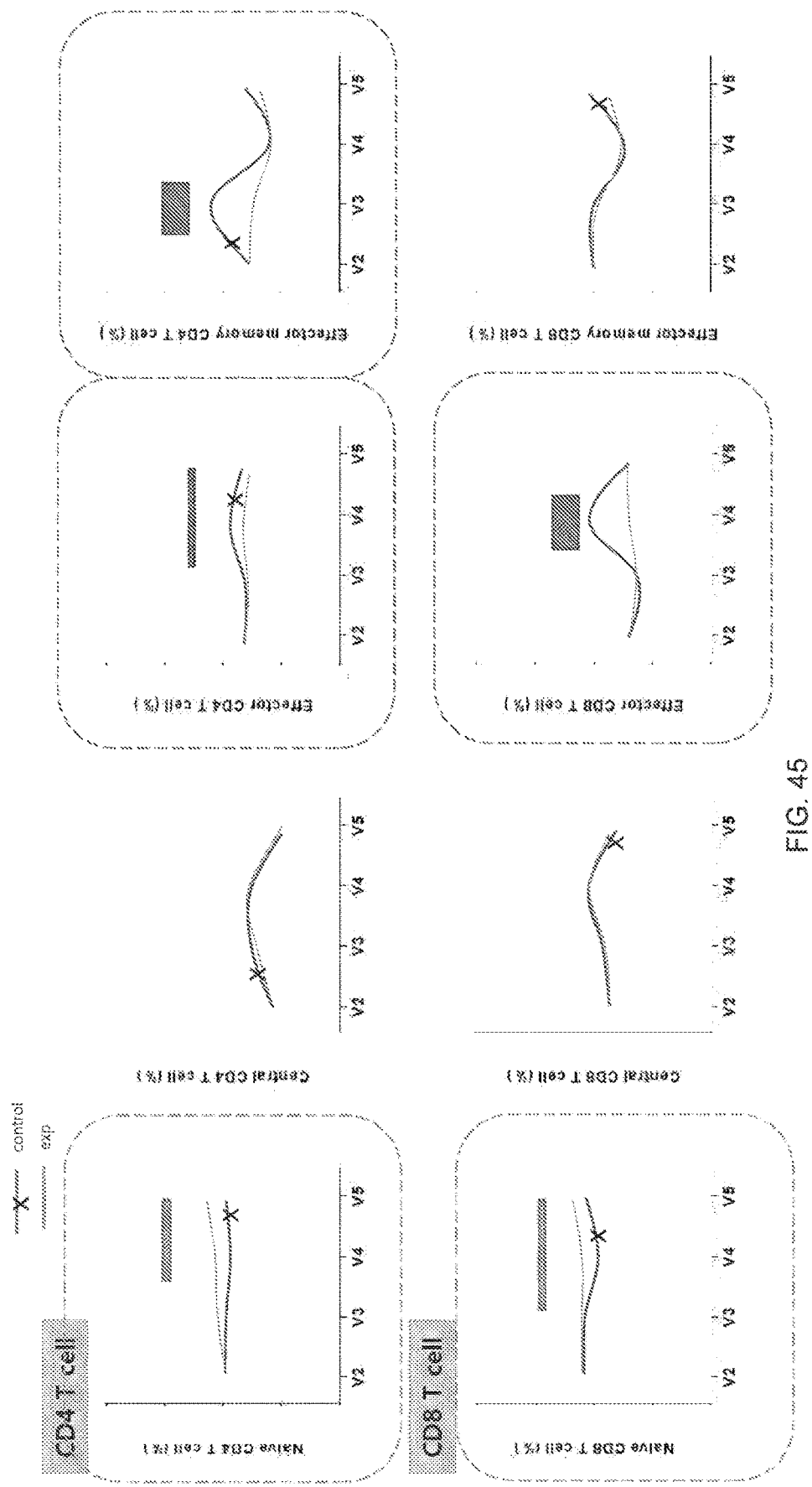
Figure 46:
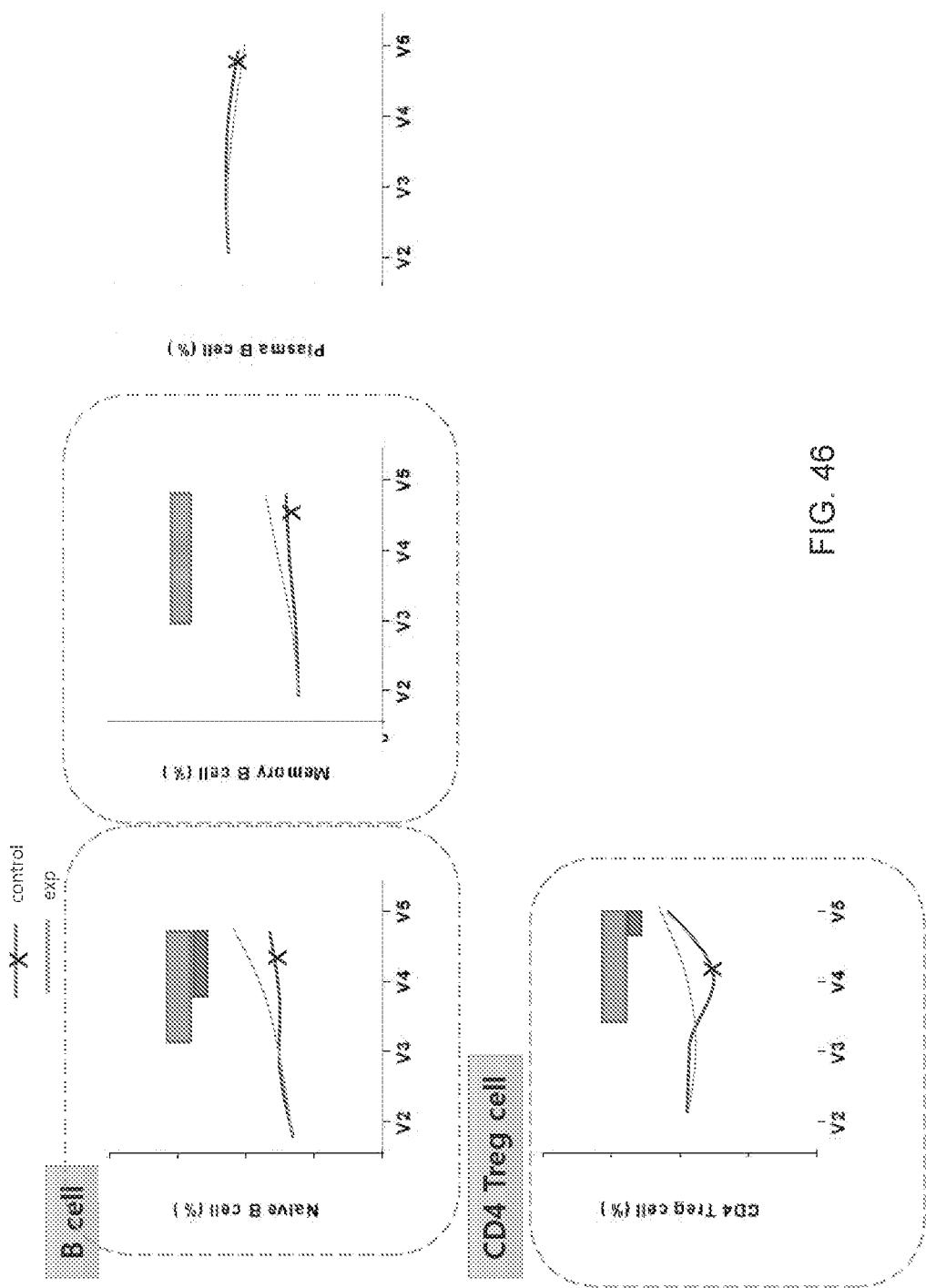

Warming up: Insert a "skip" button
Warming up: Change a default duration of 5 minutes to 3 minutes.
Appropriate external exercise: Add an indicator of duration (20-min)
Benchmark exercise: Add more exercise options (adherence rate increased)
Internal activity: Display heart rate during internal activity
Activity measures: Set a time window (5 minutes) to keep activity records in case the app is abruptly terminated
Today's condition: Add an "undo" button
Feedback function: Send an automatic alarm if the app is not used for 72 hours
Feedback function: Display a performance rate
Feedback function: Insert an automatic schedule alarm: D-7, D-1, D-day pop-up messages are required
Feedback function: Insert a goodbye scene or pop-up window if the last activity is completed.
Feedback function: Display a schedule progress FIG. 35 illustrates the adherence rate. 2 dropped out of 21 control cases, and 1 dropped out of 21 experimental cases. Here, more than 95% patients (20 out of 21) conducted all schedules of the app during 3 months, and more than 95% patients performed 75.8% of programs during 3 months.

Example 2: Details of Mobile Application

The operating system includes a patient mobile application (hereinafter "app"), a doctor's web portal, and a server connecting these two channels.

To use the application, physicians first log in to the doctor web portal, create an account for the patient to be prescribed through the doctor web portal, enter patient information, and prescribe the use of the app. The app is provided to patients in the form of a mobile app, the software needs to be downloaded to be prescribed and transmitted by the doctor, and the patient can log in to the app with the provided patient account and password to proceed, receiving activities for at least 10 minutes and maximum 30 minutes through the app (all activity records performed by patients are transmitted to the doctor web portal, and data transferred to the server is backed up once a day for loss prevention and restoration functions). The patient app divided into two sessions: exercise and immunity enhancing activity are performed after wearing a wearable device. Immunity enhancing activity was performed daily for a total of 10 minutes for a total of 5 minutes by selecting two of the five activities after deep breathing. Each schedule was adjusted by the patient, and all activities were paused or stopped halfway.

In detail, patients first access the app with their login account information, and after the first connection, the app ran without having to enter account information again. Then, the patients pressed the start button on the screen to proceed with the session. If a certain amount of time was not met at the end of the exercise, it was recorded as not performed. The vagus nerve stimulation activity was carried out in two different activities, and each activity must be carried out in succession to be recorded as completed. Patients can stop using the app at any time or when they feel uncomfortable, in the middle of a session, or between sessions, and can encourage session progress by themselves by setting push notifications for each session progress. In summary, a patient logged in, checked the health status of the day on the first screen, selected one session between exercise and immunity enhancing activity and performed the appropriate activity for each session, activity of each session was recorded. Of a certain time was not satisfied (e.g., 20 minutes for exercise and 10 minutes for vagus nerve stimulation), the activity was recorded as incomplete, and daily records were separately collected and checked. The first activity was exercise, and the second was vagus nerve stimulation activity. Exercise 2-3 times a week, the schedule can be freely set, and one exercise took 20 minutes. The vagus nerve stimulation activity was performed once a day and takes 10 minutes.

| Patient app home page screen | Health status check screen | Session selection screen | Session preparation screen | Session End Screen | Session recording screen |
|---|---|---|---|---|---|
| Patients log in by entering ID and PW | Answer your health status today | Choose between exercise and vagus nerve strengthening activity | Prepare for the session. (Top: exercise, bottom: vagus nerve strengthening activity) | At the end of the session, check the activity. (Top: exercise, bottom: vagus nerve strengthening activity) | You can check the patient's activity history |

In the test trial, the exercise sessions was conducted 2-3 times a week, a total of 30 minutes, including 5 minutes of warm-up, 20 minutes of exercise, and 5 minutes of clean-up before starting (before exercise, a target heart rate is suggested). During exercise, the wearable device Mi Smart Band (Xiaomi, China) was worn on the wrist to measure and transmit the heart rate to the patient app. The "Stop Exercise" button can be pressed to stop. After exercise, subjective evaluation of the intensity of the exercise was performed to adjust the target intensity of the next exercise. The exercise schedule was replaced with a benchmark exercise once every two weeks to see how the patient's physical strength changes. It consists of a total of 9 exercises, and each exercise was performed and the activity time was recorded and compared with the previous record. The target heart rate for the next exercise was adjusted according to the benchmark exercise performance (±3 bpm).

The vagus nerve stimulation activity was performed daily, and two activities were performed. The first activity was performed for 5 minutes with deep breathing, and the next activity is performed by selecting one of 5 activities. Examples of vagus nerve stimulation activities includes Deep breathing→Inhale and exhale according to the on-screen guide.
Listening to white noise→In a comfortable position, listen to the sounds of nature provided by the app.
Stopping breathing→Follow the on-screen guide to stop breathing and breathe every 30 seconds.
Aroma Meditation→After preparing aromas such as scented candles and diffusers, proceed with meditation according to the voice guide of the app.
Horror experience→A sense of fear through colors is presented and gazes at the screen.
Soak your face in cold water→Prepare cold water and soak your face in cold water according to the app's guide. After soaking for 10 seconds, repeat the break of 1 minute and 30 seconds to perform for 5 minutes.

Example 3: Mechanism of Action

Physical activity was measured in metabolic equivalents (METs), where 1 MET is defined as the energy required to sit quietly. Moderate activity corresponds to 3-6 METs and high intensity activity corresponds to 6 METs or more. Converting these moderate-intensity activities into heart rate corresponds to 64-76% of the maximum heart rate, and the heart rate according to age can be estimated by the following equation (unit: bpm):

(Maximum heart rate−stable heart rate)×Target exercise intensity (%)+stable heart rate.

The maximum heart rate was calculated as 220. With reference to the heart rate organized by age group, the app presents the heart rate corresponding to the moderate exercise according to the patient's age group, and presents the "target heart rate" to reach it. The heart rate was measured in real time using the wearable device Xiaomi Mi Smart Band 4. The patient wore this device on one wrist before exercising, and the device's Photoplethysmogram (PPG) Heart rate sensor measured the heart rate and delivered it to the patient app. The PPG heart rate sensor is based on the principle of optical blood flow measurement called PPG. PPG is used to measure the change in blood volume of capillaries. Then, it is converted into an electrical signal, and the peak value from the measured value is displayed as heart rate. Exercise was simultaneously measured by subjective evaluation. In the app, the patient was asked to evaluate the exercise intensity after finishing exercise in 3 steps and to adjust the next target heart rate according to the result (±3 bpm).

It is designed to induce the immune system enhancing effect by setting the duration of this exercise to 20 minutes.

Example 4: Safety Report

Study Subject is as follows:
1) Screening n=53
2) Randomization n=42 (Experimental group: 21, Control group: 21)
3) Completed study subjects n=39 (v4 point: 40)
   A. Experimental group: 20
   B. Control group: 19 (completed v4: 20)
Experimental group: R031 (dropping out after V3 visit): taking steroid due to rash and tingling sense wearing mask; The steroid which was prescribed by dermatologist is not matched with criteria of inclusion (Methylon Tab. 4 mg, Ebastel Tab. 10 mg, Stogar Tab 10 mg/1 tab per day for 10 days). Control group: R009 (Dropping out after V2 visit): Taking Hormone (for treatment of secondary amenorrhea); and R010 (Finalization of V4 visit): Taking hormone (Senselibe Tab. 1T/d) after finalization of V4 visit No flu-like symptom in both groups: Experimental and control

| Adverse event (not related to device) | Experimental group (n = 21) | Control group (n = 21) |
|---|---|---|
| Menstrual pain | 3 | 1 |
| Operation due to myopia | 1 | 0 |
| Dysmenorrhea | 0 | 1 |
| Amenorrhea* | 0 | 1 |
| Headache | 1 | 0 |
| Lumbar pain | 0 | 1 |
| Inflammation of ear | 0 | 1 |
| Depression | 1 | 0 |
| Hemorrhoid | 0 | 1 |

*Amenorrhea was found to be before enrolling in the clinical trials, but was not found in the past medical history. The hormone prescription was decided by OBGY dept, after v2 visit and the subject was dropped in the middle of clinical trials.

| Adverse event (related to device) | Experimental group (n = 21) | Control group (n = 21) |
|---|---|---|
| Knee pain** | 1 | 0 |

**Knee pain is AE related device.

Experimental group includes: 1. Menstrual pain (3): 3 between v4-5, (Pain relieving: 2 subjects with EZN6, 1 subject with Tyrenol), 2. Operation of Uterine myoma(1): between V4-V5, Feroba taken after operation, 3. Headache (1): Between V4-V5: (Carol-F Tab. Naproxen)/EZN6, 4. depression(1): diagnosed as corona-blue, Lexapro), 5. knee pain(1): Twice external activities(exercise) due to the malfunction of application activation, two days prior to visit V3. The pain developed and continued until visit of V3. There is no medication).

Control group includes: 1. menstrual pain(1): Between V4-5, two times, Tyrenol, 2. dysmenorrhea(1): Prescribed with hormone and dropped in the middle of clinical trials, 3. amenorrhea(1): found to be before enrolling in the clinical trials, but was not found in the past medical history. The hormone prescription was decided by OBGY dept, after v2 visit and the subject was dropped in the middle of clinical trials, 4. hemorrhoid(1): Between V4-V5, drug for hemorrhoids, 5. Lumbar pain(1): No medication, and 6. Inflammation of ear: Advil one time medication.

Example 5: Research Outline

A single-center, randomized, open label, no-treatment controlled, digital device study was conducted to evaluate the efficacy, safety and feasibility of the app in healthy adults aged 19 to under 50. The purpose of this clinical trial is to evaluate the efficacy, safety and feasibility of the app in healthy adults. This study consisted of two groups, the control group (N=16, Visit 5: N=15) and the test group (SAT-008 group: N=16; Sub-Group: High Performers (N=6) and Low Performers (N=10)). For 13 weeks from baseline, the test group used a mobile application device, and the control group maintained the same daily routine as the baseline without using the app. Influenza vaccination was given at week 1 after baseline, and blood samples were collected at baseline, week 1, week 5, and week 13 to observe changes in immune cells compared to baseline in each group and between groups, and checked the change in influenza antibody production rate and titer compared to the vaccination day (week 1) between groups. The research was 12 months from the date of IRB approval.

The investigator (the doctor in charge) entered the information of the study subject through the doctor's website and made a prescription for the use of the mobile application, and the subject or agent who received the prescription was issued a login information to access the app. Research subjects installed the app on their smart phone (or smart phone that was paid for research), logged in, and ran.

The app consists of exercise activity and immunity strengthening activity, and exercise activity was performed 2-3 times a week, and immunity strengthening activity was performed daily. Subjects started by selecting exercise and immunity enhancing activities on the application screen. Before starting both activities, the app asked about the subject's physical condition. If the subject responds that he or she was not in good shape due to heat or body aches, the application's activity selection button was deactivated so that the activity cannot be performed that day.

Exercise activity was carried out for 30 minutes (including preparatory exercise and cleanup exercise) 2-3 times a week. During exercise, the study subject wore a wearable device (Smart Watch: Mi Smart Band 5.0) to pass the information the subject's exercise status to the application. If the subject felt difficulty during exercise, he or she stopped and resumed at any time. If the exercise time measured after the subject pressed the exercise end button is short, the exercise activity was not recorded.

Benchmark exercise was performed once every two weeks to check the change in physical strength of the study subjects. In the benchmark exercise, three sets of three exercises were performed and the time and number of exercise were measured. Performed this every other week and checked the changes in time and frequency.

Immune strengthening activity consists of five static activities, of which two activities were performed for 10 minutes every day. It took 5 minutes per activity, and two activities were performed in succession to be recorded as completing the activity.

Any activity could be stopped at any time, even if it is in progress, and could be restarted from the point of interruption, on the same day only. It was important for the subject to perform activities through the app consistently in accordance with the schedule, and by setting the push alarm function in the application, the activity schedule could be continuously encouraged.

The activity data was delivered to the investigator in real time, and the investigator checked the activity details of the research subject by accessing the doctor web.

This study was designed as a single-center, open label, control, and investigator-led study to evaluate the efficacy, safety and feasibility of a digital device for research in the form of a mobile application in healthy adults who will be vaccinated against influenza. At the screening visit (Visit 1), the subject voluntarily agreed in writing to participate in this study, and then proceed with the screening procedure. If it met the selection criteria and did not meet the exclusion criteria, the study subjects were randomly assigned 1:1 to the test group (using a digital device for research) and the control group (maintaining daily activities) (visit 2). In the case of the test group, the digital device for research was used 7 times a week. In the case of the control group, daily activities were maintained as before participation in the study, and no intervention was performed.

The following medical history was collected regardless of the period: uncontrolled diabetes (HbA1c 6.5% or more, or fasting (8 hours or more) plasma glucose 126 mg/dL or more); tumor; autoimmune disease; neurological disease; circulatory disease; respiratory diseases; liver or kidney disease; acute infectious disease. The following medical history was investigated according to the relevant period: fever exceeding 38° C. body temperature (within 4 weeks before screening). Both the test group and the control group visited the conducting institution one week later (Visit 3) and receive influenza vaccination. Thereafter, the test group continued to use the research digital device for 12 weeks, the control group maintained their daily activities. Both groups visited the implementation site at 5 weeks (Visit 4) and 13 weeks (Visit 5) from the time of baseline, and was assessed for laboratory tests and immunological indicators, quality of life questionnaires, and safety (including identification of influenza symptoms).

Major selection criteria included healthy adult male and female aged 19 to 45, person who received influenza vaccination the previous year, those who are scheduled to receive influenza vaccine, a person who is judged to be suitable as a subject based on the judgment of the investigator through the screening test (clinical findings, medical history, vital signs, body mass index, physical examination, laboratory test), those who do not exercise regularly: As a result of physical activity evaluation using the International Physical Activity Questionnaires (IPAQ), persons who are under low intensity activity (does not correspond to IPAQ 2 or 3, or physical activity less than 600 MET-min/week). For women of childbearing age, those who have agreed to avoid pregnancy or use appropriate contraceptive methods during the clinical trial period; for men, those who have agreed to use appropriate contraceptive methods during the clinical trial period. A person who understands this clinical trial and is able to participate in good faith and agrees to abide by the restrictions. Those who agreed to visit for follow-up and blood collection during the study period. A person who voluntarily agrees to participate in this research and has signed a written consent form. Those who can use the application using a smartphone.

Major Selection Exclusion Criteria include: those who have some medical history, such as current infectious disease (HIV, HBV, HCV) test results are positive, those who have uncontrolled diabetes (HbA1c 6.5% or more, or fasting (8 hours or more) plasma glucose 126 mg/dL or more), those with a history of tumor, persons with a history of autoimmune diseases.

Major selection exclusion criteria further include: those with neurological, circulatory, respiratory, liver or kidney disease (excluding controlled hypertension (systolic/diastolic blood pressure less than 140/90 mmHg)), a person who has behavioral, cognitive, or mental illness that affects the understanding and compliance of the clinical trial protocol when judged by the investigator, persons with a history of acute infectious diseases, those who had fever exceeding 37.5° C. in body temperature within 4 weeks month before screening, prior to screening, persons who use other drugs like immunosuppressants, immunomodulators, immunoglobulins, blood-derived agents, or other drugs that may affect immunity, as determined by the investigator, as follows:

Those who received an immunosuppressant within 60 days prior to screening or who intend to administer it during the clinical trial period Those who received an immunomodulator within 6 months prior to screening Those who have received immunoglobulins or blood-derived products within 3 months prior to screening In addition, major selection exclusion criteria include those who received a live vaccine within 28 days prior to screening, persons who received killed vaccines within 14 days before screening, those who are taking medications not approved by the investigator, in the judgment of the investigator, a person with a history of alcohol or drug abuse affecting participation in the clinical trial, people who are currently smoking, pregnant and lactating women, those who have applied/administered medical devices/drugs for other clinical trial within 6 months prior to screening or plan to apply/administer them during the trial period, and a person who is judged to be unsuitable for participation in a clinical trial by the investigator.

Primary efficacy endpoint included NK cell change amount for innate immunity evaluation at 5 weeks compared to baseline, and secondary efficacy endpoint included as follows:

Changes in the number and activity of NK cells for the evaluation of innate immunity at 1 and 13 weeks compared to baseline.

Changes in the following indicators at 1, 5, and 13 weeks compared to the baseline CD4+ T cells, CD8+ T cells: B cell Pro-inflammatory cytokines (IL-6, TNF-a and IL-1b), Anti-inflammatory cytokine (IL 10), IFN-γ.

Changes in antibody production rate and antibody titer after influenza vaccination of blood samples collected at weeks 5 and 13 compared to the vaccination day.

Influenza-like symptoms (fever and cough or sore throat above 37.8° C.) or confirmed influenza on the vaccination day, visit 4, visit 5.

Compliance.

Questionnaire of quality of life at 1, 5, 13, and 25 weeks compared to the baseline (SF-36).

| Inspection/Visit Schedule | | | | | |
|---|---|---|---|---|---|
| Visit No. | Screening 1 | Baseline 2 | Vaccination date 3 | Interim visit 4 | End/Discontinuation 5 |
| Visiting week | ~-W2 | D0 | W1 | W5 | W13 |
| Visit window (Day) | | | ±2 Days | ±3 Days | ±5 Days |
| Acquiring written consent Screening numbering | O | | | | |
| Demographic Information Survey | O | | | | |
| Medical history/drug administration history investigation | O | O | | | |
| Height/weight | O | O | ◇ | O | O |
| Vital signs | O | O | ◇ | O | O |
| Physical examination | O | O | ◇ | O | O |
| Physical activity evaluation | O | O | ◇ | O | O |
| Laboratory tests | O | | | | O |
| Immune serum test | O | | | | |
| Pregnancy test | O | | | | |
| Immunity indicator test | | O | ◇ | O | O |
| Selection/exclusion criteria check | O | O | | | |
| Random numbering | | O | | | |
| Quality of life questionnaire | | O | ◇ | O | O |
| Education on how to use digital devices for research (test group only) | | O | | | |
| Use of research digital devices (test group only) | | O | O | O | O |
| Influenza vaccination | | | O | | |
| Influenza antibody test (at Visits 3-5) | | | ◇ | O | O |
| Check of influenza-like symptoms and confirmation | | | ◇ | O | O |
| Check of adverse events | | | O | | O |
| Check of concomitant drugs | | | O | O | |
| Compliance check | | | O | O | O |

The Screening Visit (Visit 1) and the Baseline Visit (Visit 2) may take place on the same date. If it is carried out on the same day, duplicate inspections are conducted only once. Baseline testing is performed prior to use of the research digital device. The date of visit to the implementing institution afterwards is based on the baseline visit (visit 2). In the case of dropout or early termination, the same inspection and evaluation as the termination visit shall be performed. All procedures related to the study was made after obtaining written consent. Demographic information survey: Survey demographic information (age, gender, etc.) Vital signs (blood pressure, respiratory rate, pulse rate, body temperature) were measured at each visit. Physical activity was evaluated using the shortened Korean version of the International Physical Activity Questionnaire. If there was a test result measured within 4 weeks prior to screening, it was used. However, if a clinically significant abnormal result existed under the judgment of the researcher, an additional test was performed at the time of screening. Hematological tests: Hb, Hct, RBC, WBC, Differential WBC count, Platelets count; Blood biochemical tests: Na, K, Cl, P, Ca, Creatinine, BUN, Uric acid, ALT, AST, ALP, CPK, Total bilirubin, Amylase, Lipase, Albumin, Total protein, HbA1c, FBG (FPG); Urinalysis: pH, Specific gravity, Nitrite, Protein, Glucose, Ketone bodies, Bilirubin, Urobilinogen, Occult blood, WBC, etc. Immunoserum test included HBsAg, HCV Ab, and HIV Ab. For women of childbearing age, a pregnancy test was done at Visit 1 and a urine HCG or serum HCG test was performed. Immuno-marker tests included NK cell, CD4+ T cells, CD8+ T cells, Pro-inflammatory cytokines (IL-6, TNF-a and IL-1b), Anti-inflammatory cytokine (IL-10), and IFN-γ. Quality of life was assessed using the SF-36 questionnaire. Research subjects assigned to the test group were to continue to use the research digital device for 13 weeks from the baseline visit and were automatically deactivated at the end. If the visit to the institution and the day of the exercise overlapped, the exercise was performed after the visit to the institution was completed. If the symptoms or symptoms that existed before the application of the research digital device/drug (influenza vaccine) were worsened after the application of the research digital device/pharmaceutical, it was reported as an abnormal case. Abnormal cases related to influenza vaccines were identified by dividing them into local and systemic, and whether or not there are influenza-like symptoms was checked. 30 minutes after influenza vaccination, acute abnormalities such as anaphylaxis was checked.

Descriptive statistics (mean, standard deviation, median, minimum, maximum) for the NK cell result and the amount of change compared to the baseline at 5 weeks after the application of the digital device for research were presented by group, and changes within each group were checked with a paired t-test or a Wilcoxon signed-rank test. Covariance analysis was performed to test for differences between groups.

Secondary efficacy endpoint includes the followings: 1) changes in the number and activity of NK cells for innate immunity assessment at 1 and 13 weeks compared to baseline, 2) after applying the research digital device, descriptive statistics (mean, standard deviation, median, minimum, maximum) for the NK cell results at week 1 and week 13 and the amount of change at each time point compared to the baseline were presented for each group. In order to test for differences between groups, a covariance analysis with corrected base values was performed, 3) the amount of change by immunity index* at 1, 5, 13 weeks compared to baseline, 4) for each indicator, descriptive statistics (mean, standard deviation, median, minimum, maximum) for the results at week 1, week 5, and week 13 after applying the digital device for research and the amount of change at each time point compared to the baseline were presented by group. To test for differences between groups, a covariance analysis with corrected baseline values was performed. *CD4+ T cells, CD8+ T cells, B cell, Pro-inflammatory cytokines (IL-6, TNF-a and IL-1b), Anti-inflammatory cytokine (IL-10), IFN-γ. 5) changes in antibody production rate and antibody titer after influenza vaccination, 6) the ratio of influenza antibodies at 1 week (before vaccination on the day of vaccination), 5 weeks, and 13 weeks was presented for each group, and changes within the group were confirmed by paired t-test or Wilcoxon signed-rank test for intra-group difference testing. Covariance analysis was performed to test for differences between groups, 7) influenza-like symptoms and confirmation, 8) the frequency and ratio of influenza-like symptoms or confirmation of influenza-like symptoms at 1, 5, and 13 weeks were presented, the incidence and severity of each symptom are presented by group, and the chi-square test or Fisher's exact test was conducted to test the differences between groups, 9) compliance, 10) descriptive statistics (mean, standard deviation, median, minimum, maximum) for each section (exercise and immunization activity) and total sessions for the number of completion, discontinuation, and non-perform of the test group at 1, 5, and 13 weeks.) were presented, 11) questionnaire on the quality of life at 1, 5, and 13 weeks compared to baseline (SF-36), 12) after applying the digital device for research, descriptive statistics (mean, standard deviation, median, minimum, maximum value) for each item's score of the quality of life questionnaire (SF-36) at 1, 5, and 13 weeks and the amount of change at each time point compared to the baseline were presented for each group, and an analysis of variance was conducted to test the differences by item in the quality of life questionnaire between groups.

The number of subjects with expression, expression rate (%), and expression number for Treatment-Emergent Adverse Event (TEAE), Adverse Device Effect (ADE), Serious Adverse Event (SAE), and Serious Adverse Device Effect (SADE), that occur after the application of research digital devices, were presented. And Two-sided 95% confidence intervals for the expression rate (%) were presented. To test whether there was a difference in the incidence of adverse events between groups, a chi-square test or Fisher's exact test was performed.

Descriptive statistics (number of study subjects, average, standard deviation, median, minimum, maximum) for each time point and the amount of change at each time point compared to the baseline value for the vital sign result were presented. Changes within the group were confirmed with the paired t-test or the Wilcoxon signed-rank test. In addition, two-sample t-test or Wilcoxon rank sum test was performed to test the differences between groups for changes before and after the application of the research digital device. For each item of physical examination, the results showing clinically significant abnormalities (Abnormal/CS) at least once after the application of the research digital device were listed.

For the laboratory test results, continuous variables provide descriptive statistics (number of subjects, average, standard deviation, median, minimum, maximum) for each time point and the amount of change at each time point compared to the baseline value. Changes within the group were confirmed with the paired t-test or the Wilcoxon signed-rank test. In addition, two-sample t-test or Wilcoxon rank sum test was performed to test the differences between groups for changes before and after the application of the research digital device. In addition, the frequency and percentage of subjects who show clinically significant abnormalities (Abnormal/CS) at least once after the application of research digital device for each of the laboratory tests were presented. If necessary, it was divided into normal or clinically insignificant abnormality (Normal or Abnormal/NCS) and clinically significant abnormality (Abnormal/CS), and was presented in the form of a shift table. McNemar's test for intragroup changes was performed to check for differences between visits FIGS. 41-68 show the results from the above clinical studies. All data analysis was performed based on normalization with baseline V2 (folder change).

Figure 47:
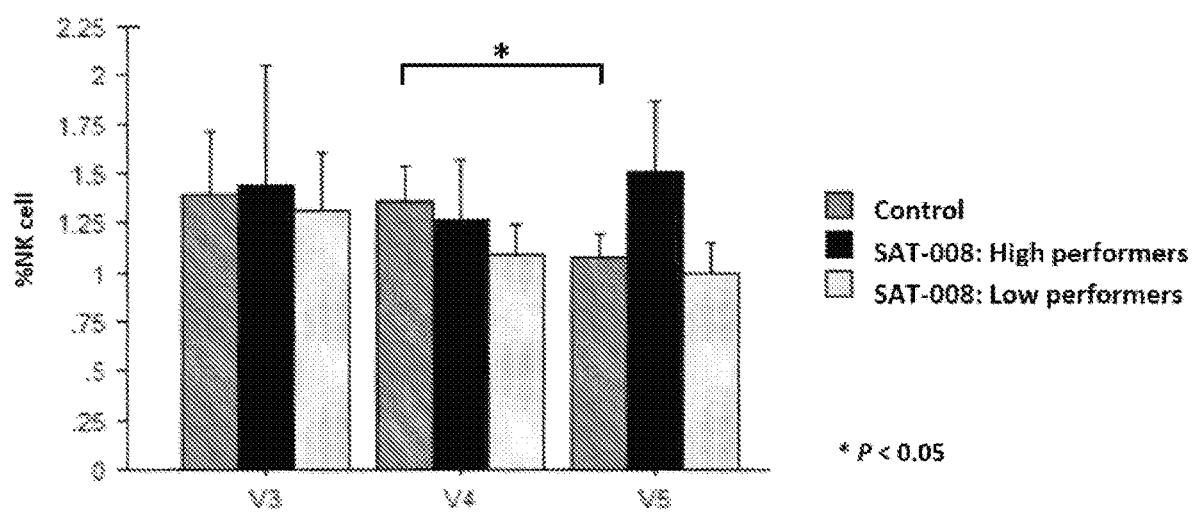
FIG. 47 shows a graph illustrating results of NK cells populations among groups in the time of each visiting (V3) (1 week), V4 (5 weeks), and V5 (13 weeks) (Anova analysis).
Figure 48:
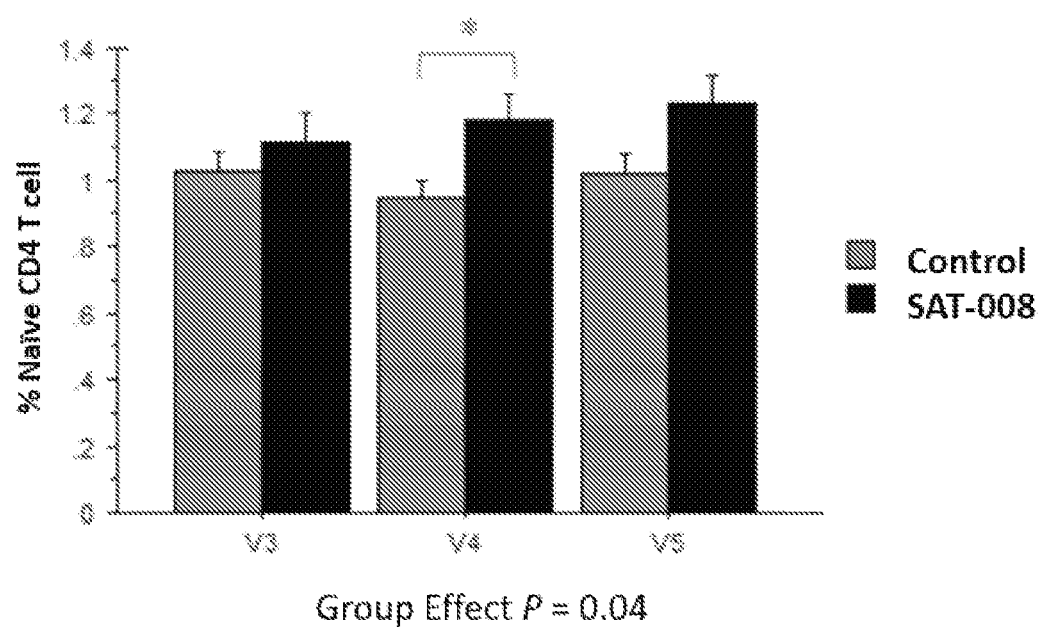
FIG. 48 shows a graph illustrating results of Naive CD4 T cell among groups in the time of each visiting V3, V4, and V5.
Figure 49:
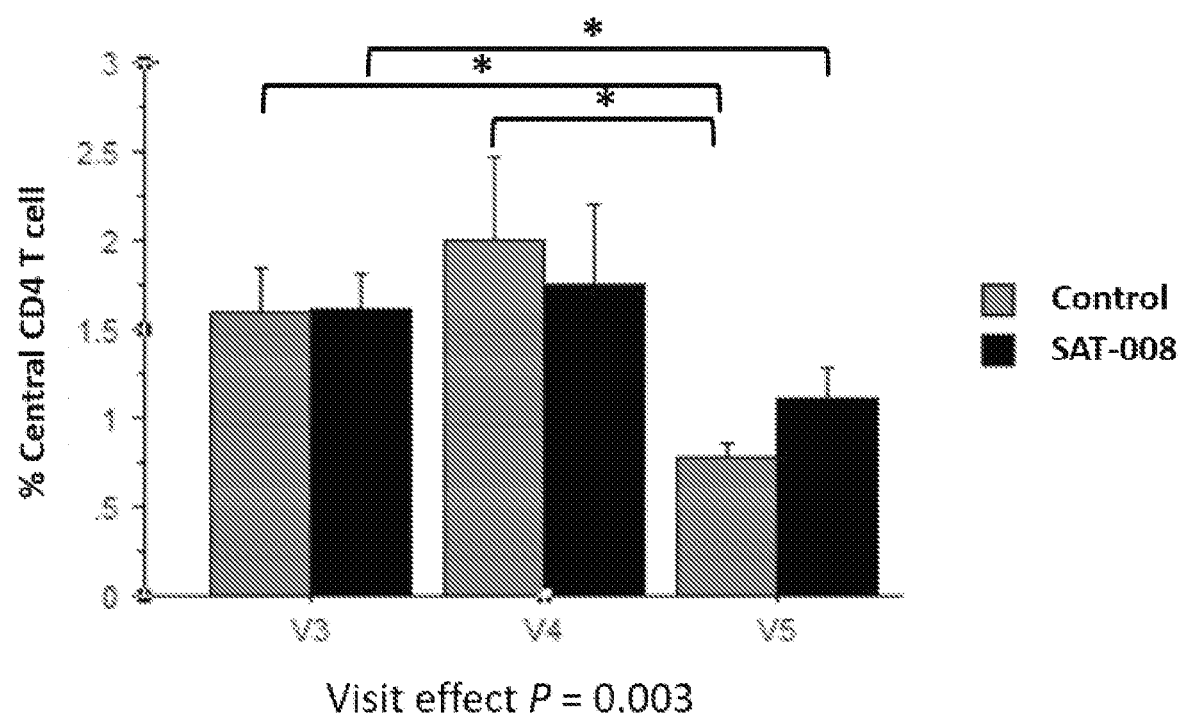
FIG. 49 shows a graph illustrating results of Central CD4 T cell among groups in the time of each visiting V3, V4, and V5.
Figure 50:
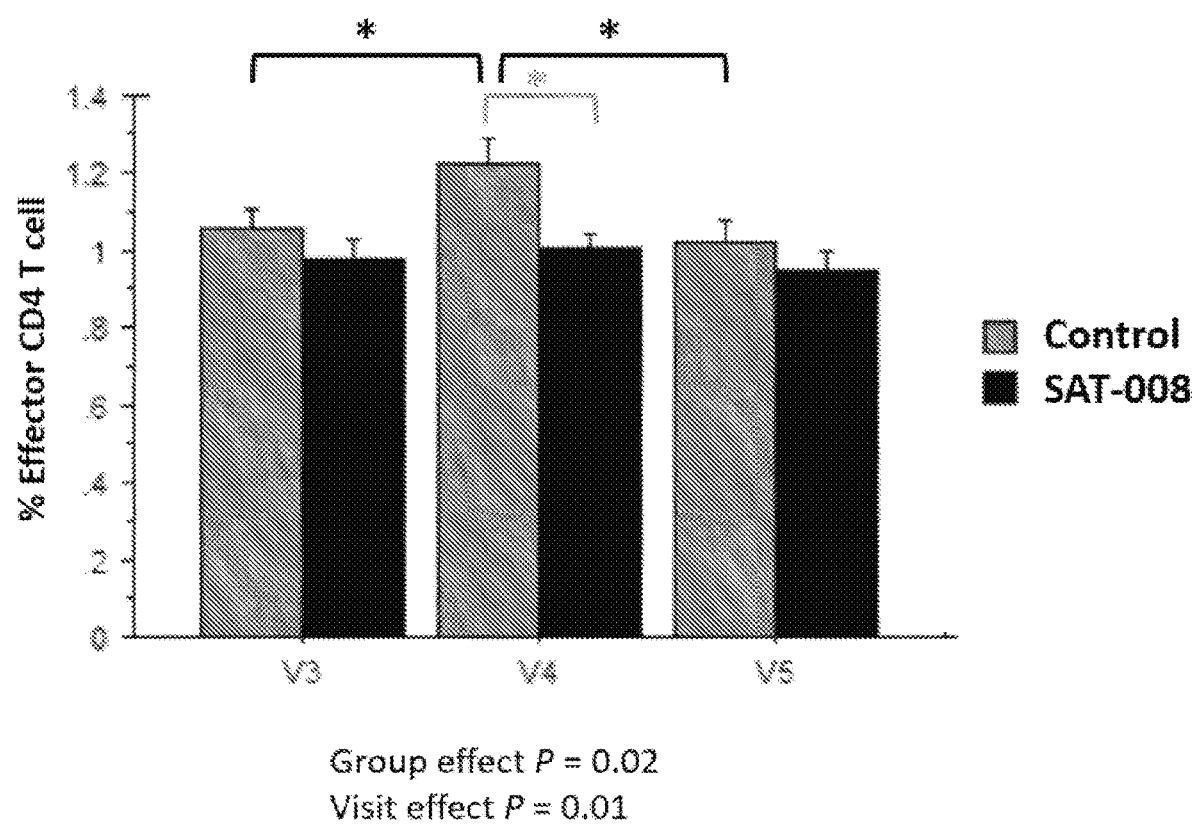
FIG. 50 shows a graph illustrating results of Effector CD4 T cell among groups in the time of each visiting V3, V4, and V5.
Figure 51:
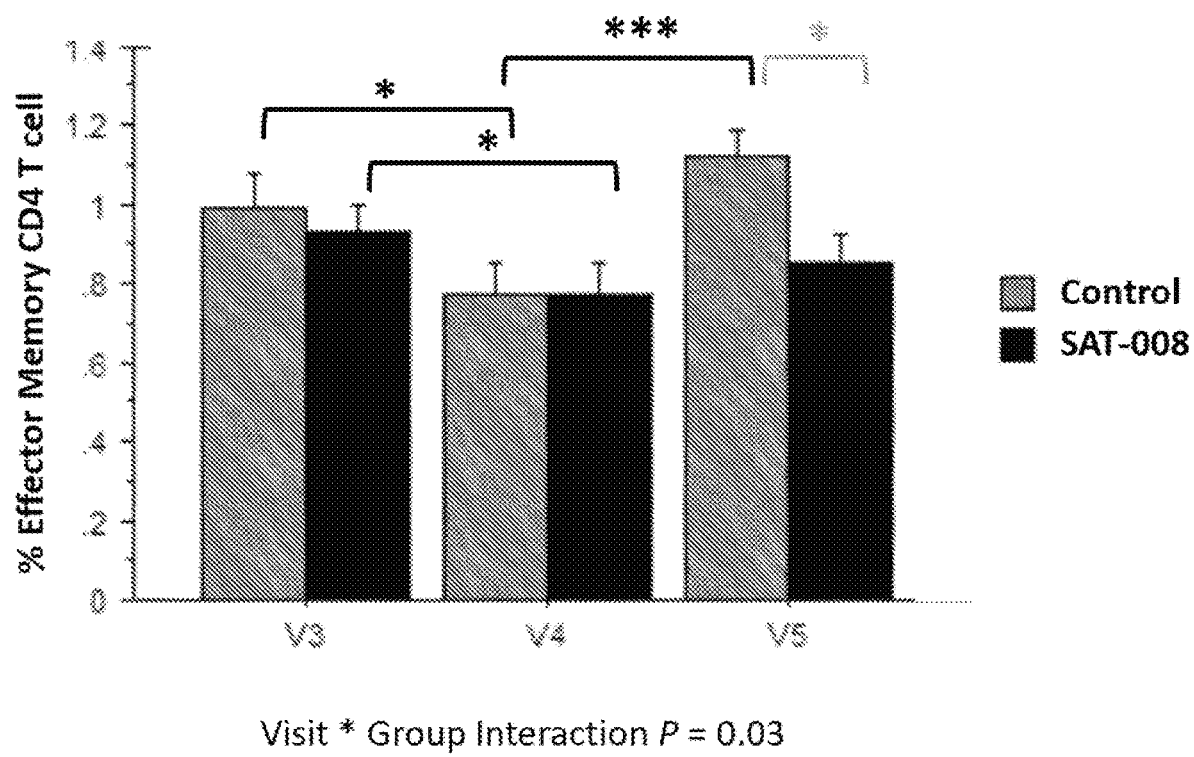
FIG. 51 shows a graph illustrating results of Effector Memory CD4 T cell among groups in the time of each visiting V3, V4, and V5.
Figure 52:
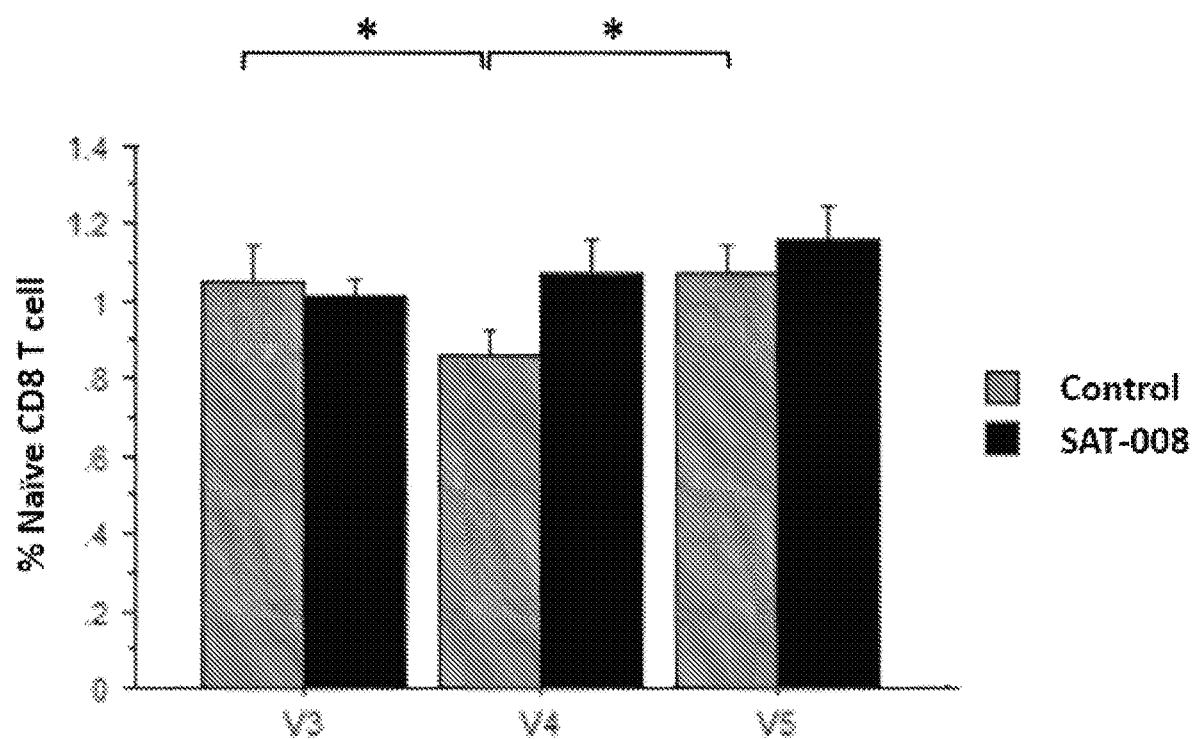
FIG. 52 shows a graph illustrating results of Naive CD8 T cell among groups in the time of each visiting V3, V4, and V5.
Figure 53:
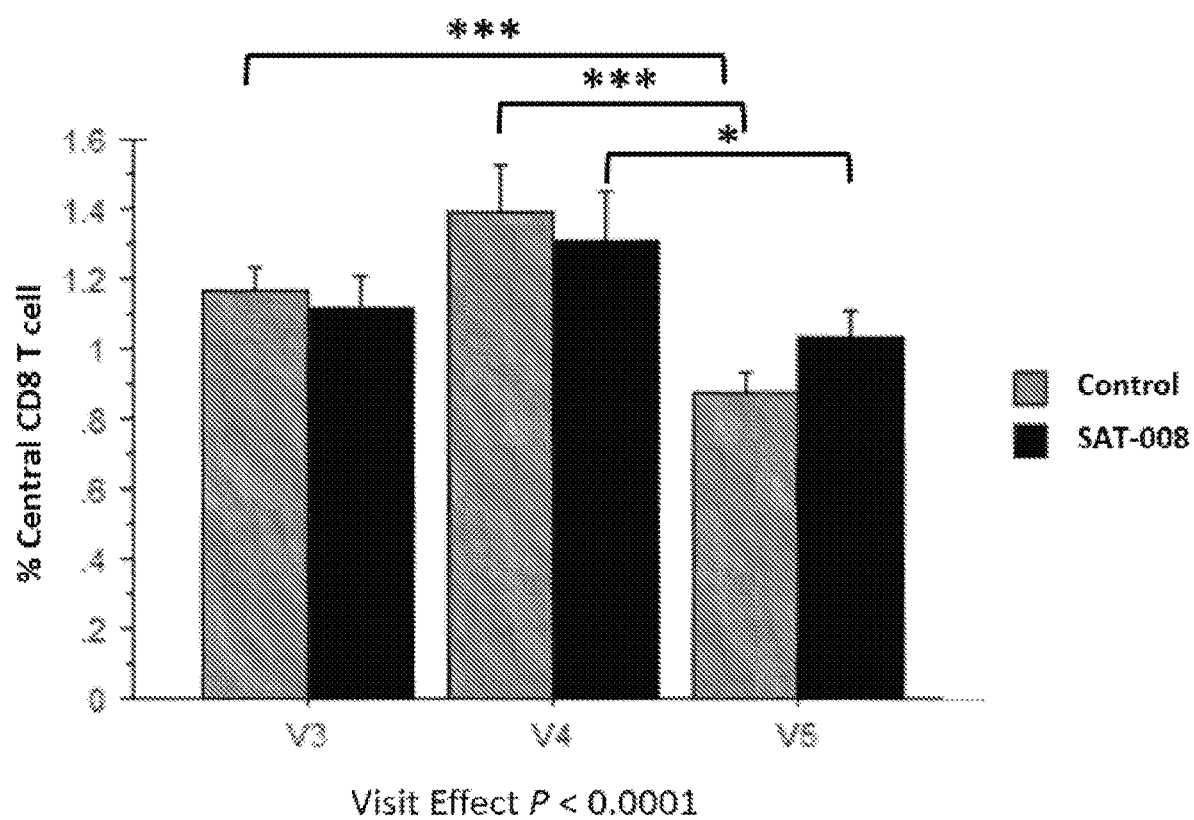
FIG. 53 shows a graph illustrating results of Central CD8 T cell among groups in the time of each visiting V3, V4, and V5.
Figure 54:
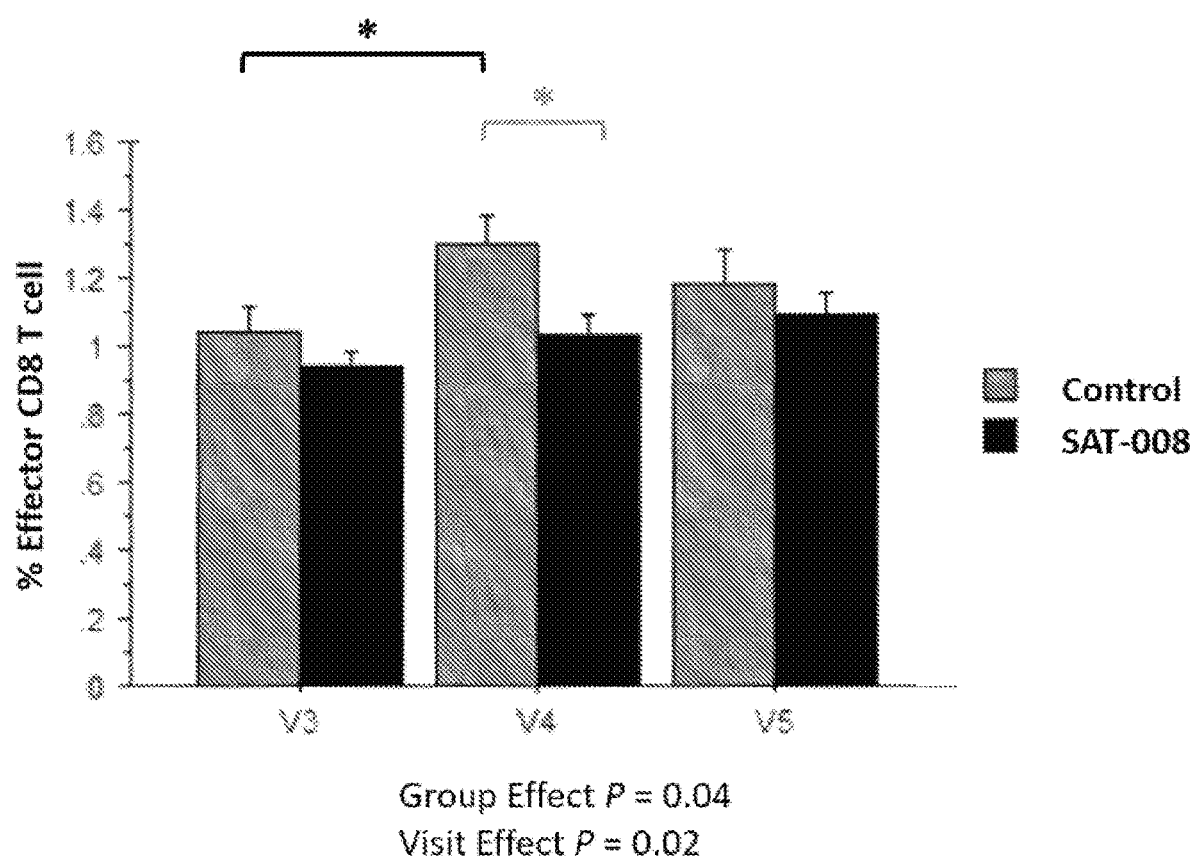
FIG. 54 shows a graph illustrating results of Effector CD8 T cell among groups in the time of each visiting V3, V4, and V5.
Figure 55:
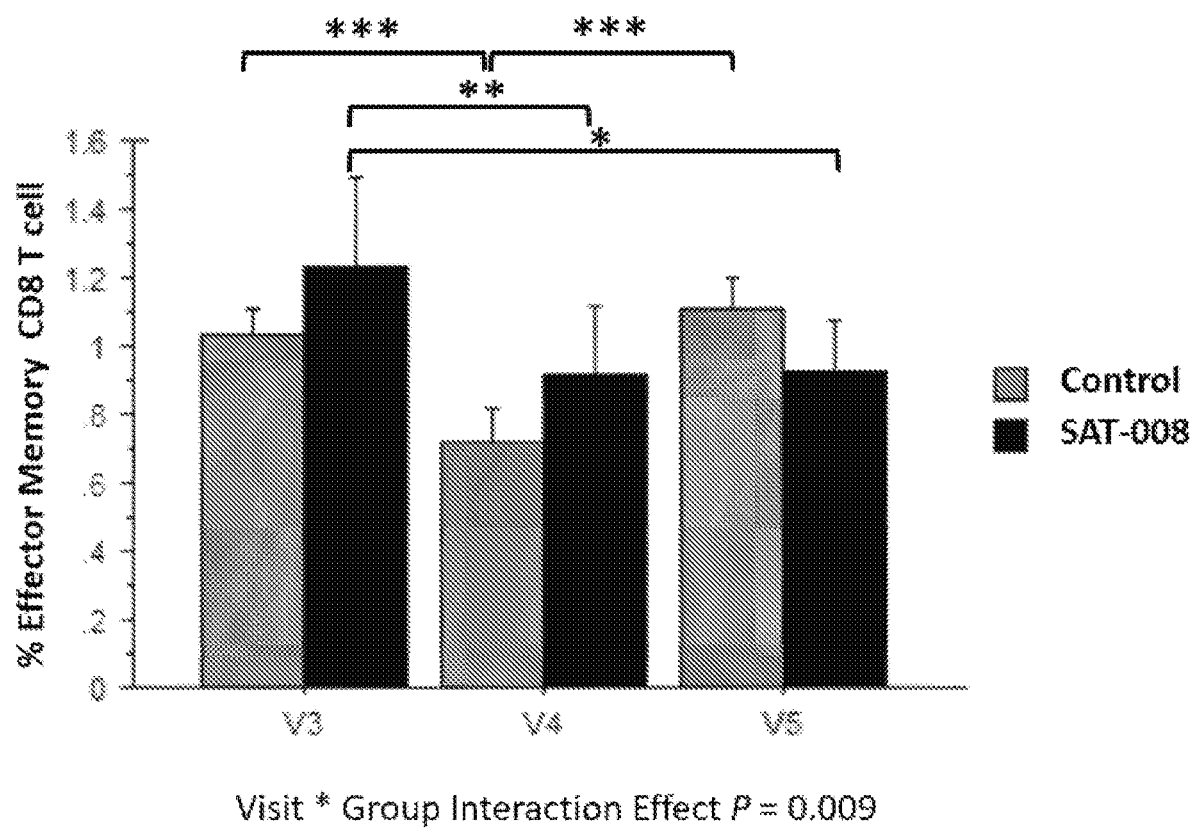
FIG. 55 shows a graph illustrating results of Effector Memory CD8 T cell among groups in the time of each visiting V3, V4, and V5.
Figure 56:
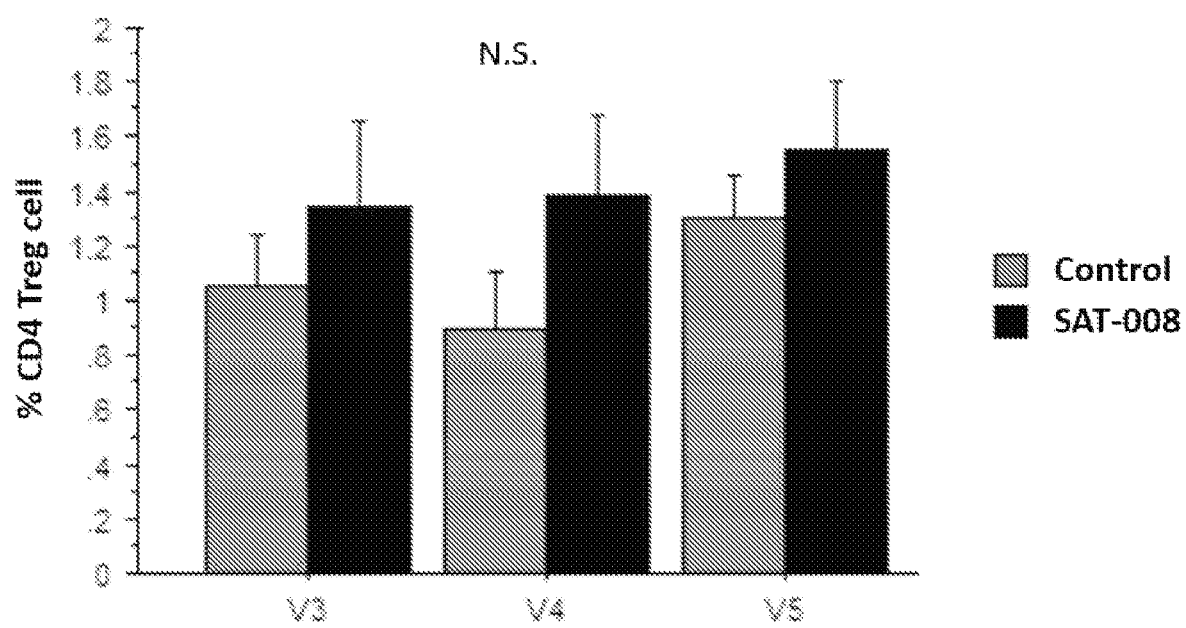
FIG. 56 shows a graph illustrating results of CD4 Treg (CD25+Foxp3+) cells populations for the control group and the experimental group in the time of each visiting V3, V4, and V5.
Figure 57:
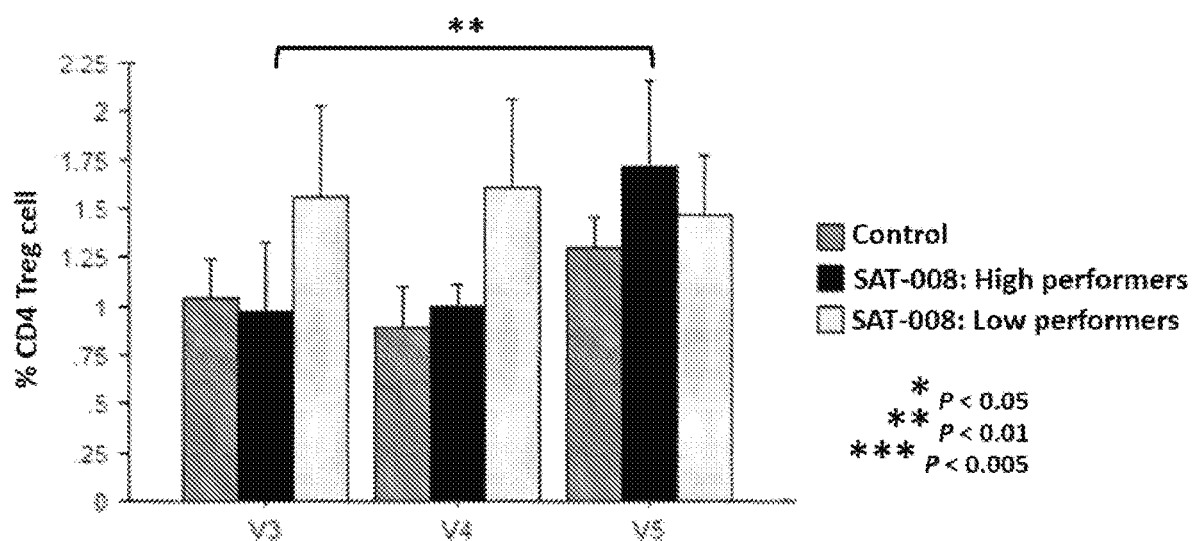
FIG. 57 shows a graph illustrating results of CD4 Treg (CD25+Foxp3+) cells populations for the control group, and high performer group, and the lower performer group in the time of each visiting V3, V4, and V5.
Figure 58:
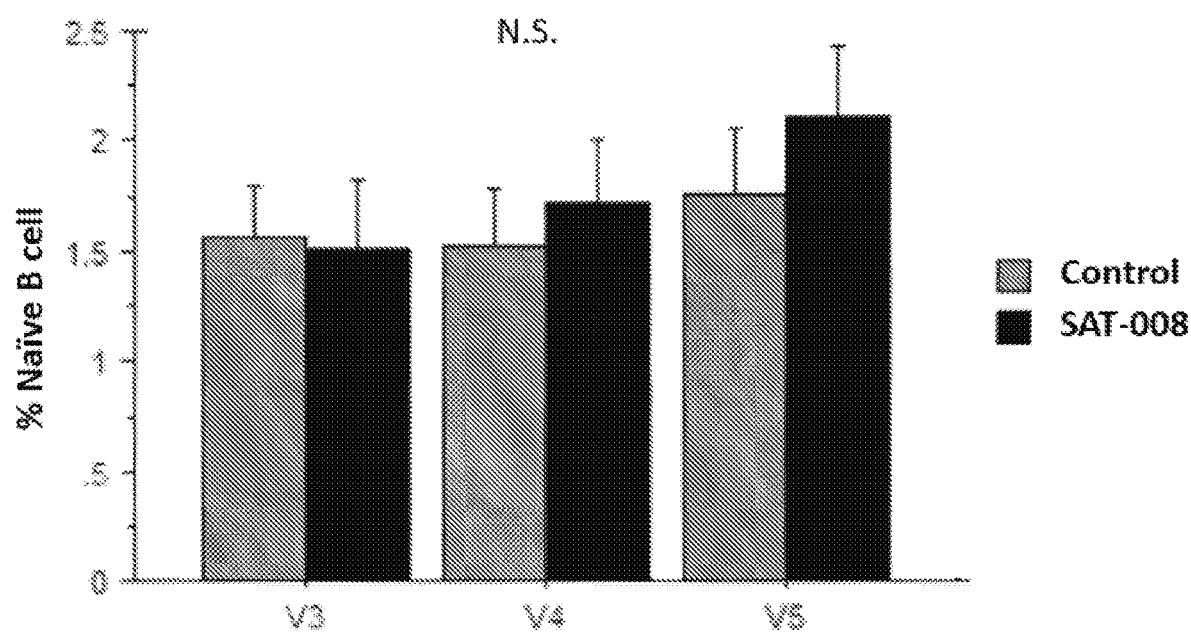
FIG. 58 shows a graph illustrating results of Naïve B cell among groups in the time of each visiting V3, V4, and V5.
Figure 59:
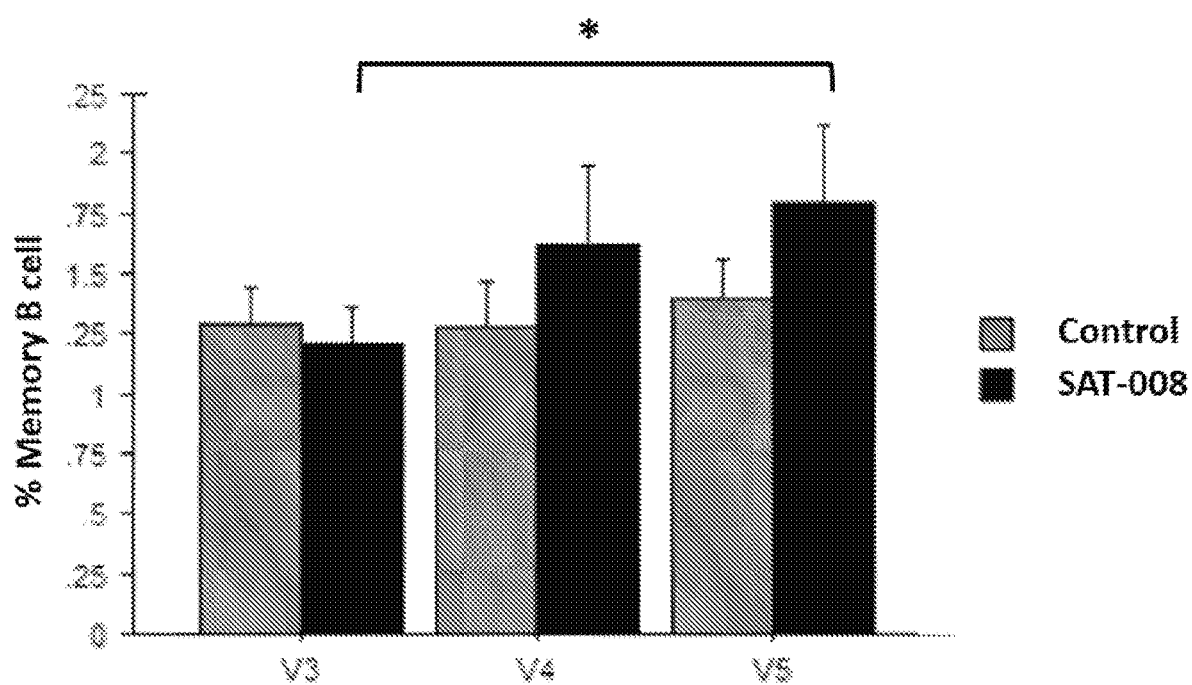
FIG. 59 shows a graph illustrating results of Memory B cell among groups in the time of each visiting V3, V4, and V5.
Figure 60:
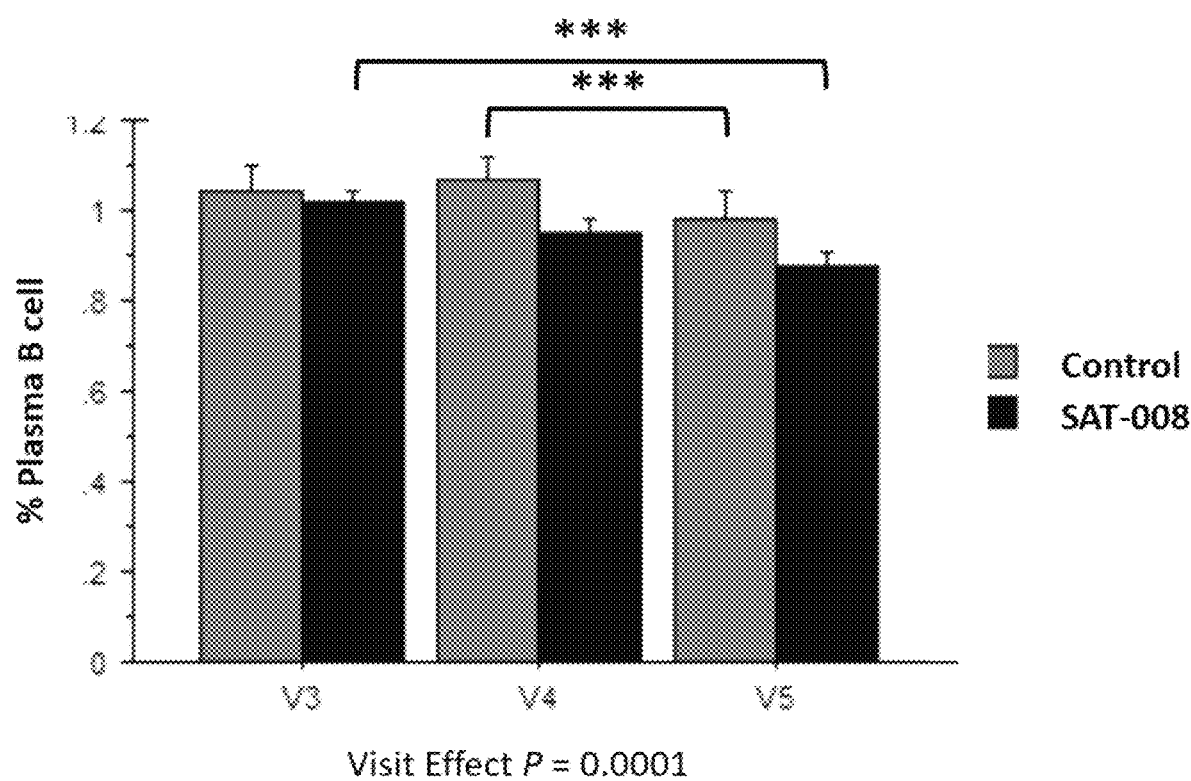
FIG. 60 shows a graph illustrating results of plasma B cell among groups in the time of each visiting V3, V4, and V5.
Figure 61:
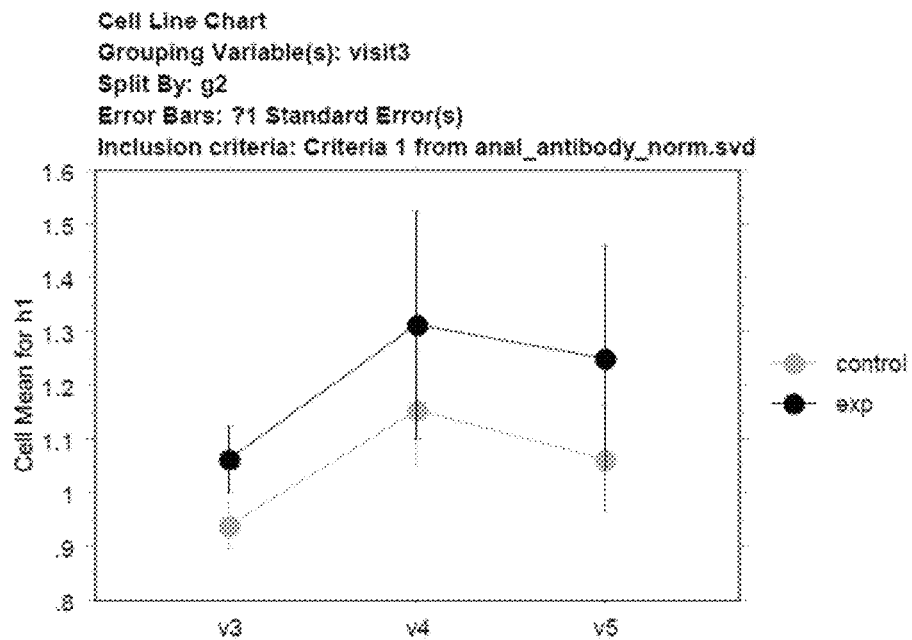
FIG. 61 shows a graph illustrating results of the antibody titer for the control group and the experimental group in the time of each visiting V3, V4, and V5 in H1N1 [A/Guandong-Maonan/SWL1536/2019].
Figure 62:
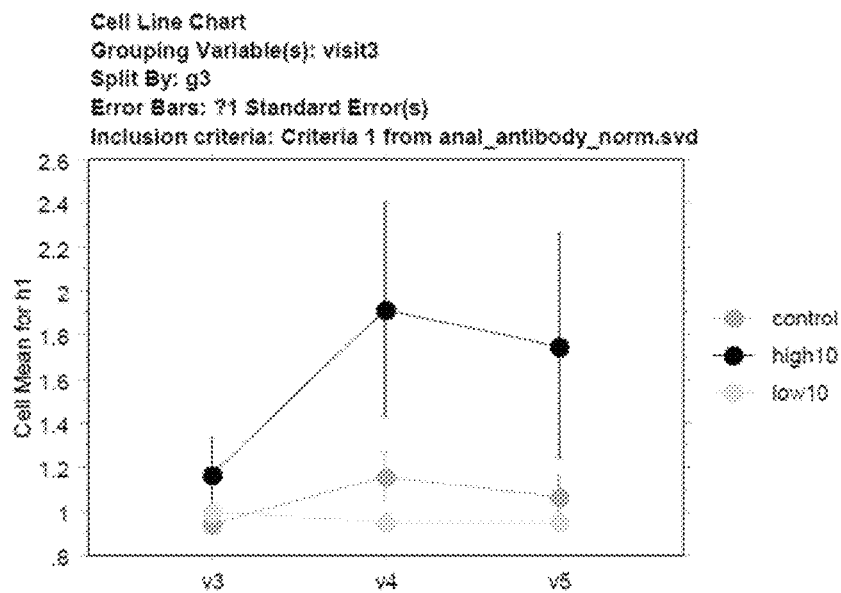
FIG. 62 shows a graph illustrating results of the antibody titer for the control group, and high performer group, and the lower performer group in the time of each visiting V3, V4, and V5 in H1N1 [A/Guandong-Maonan/SWL1536/2019].
Figure 63:
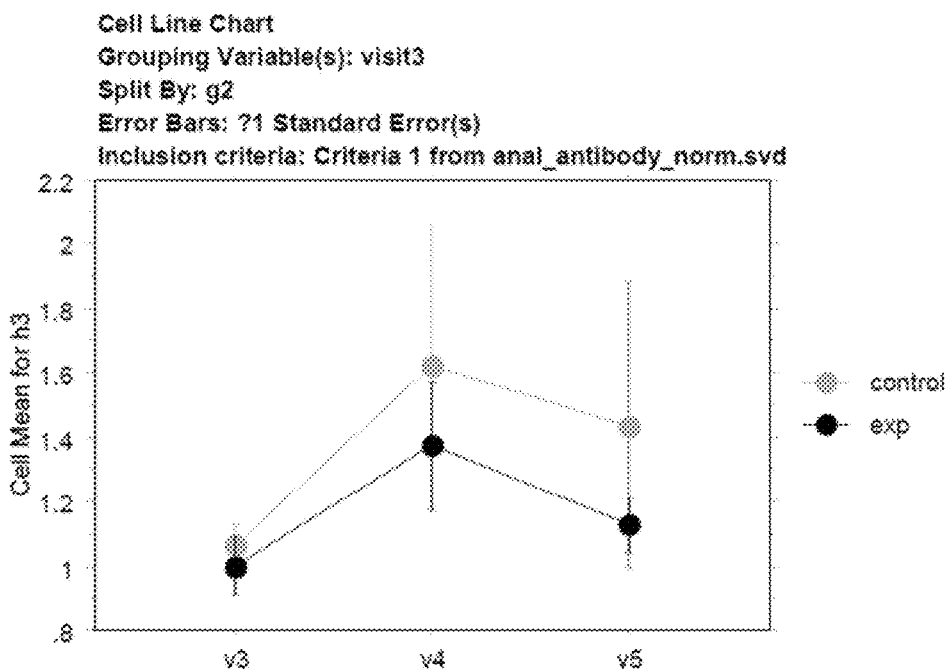
FIG. 63 shows a graph illustrating results of the antibody titer for the control group and the experimental group in the time of each visiting V3, V4, and V5 in H3N2[A/HongKong/2671/2019].
Figure 64:
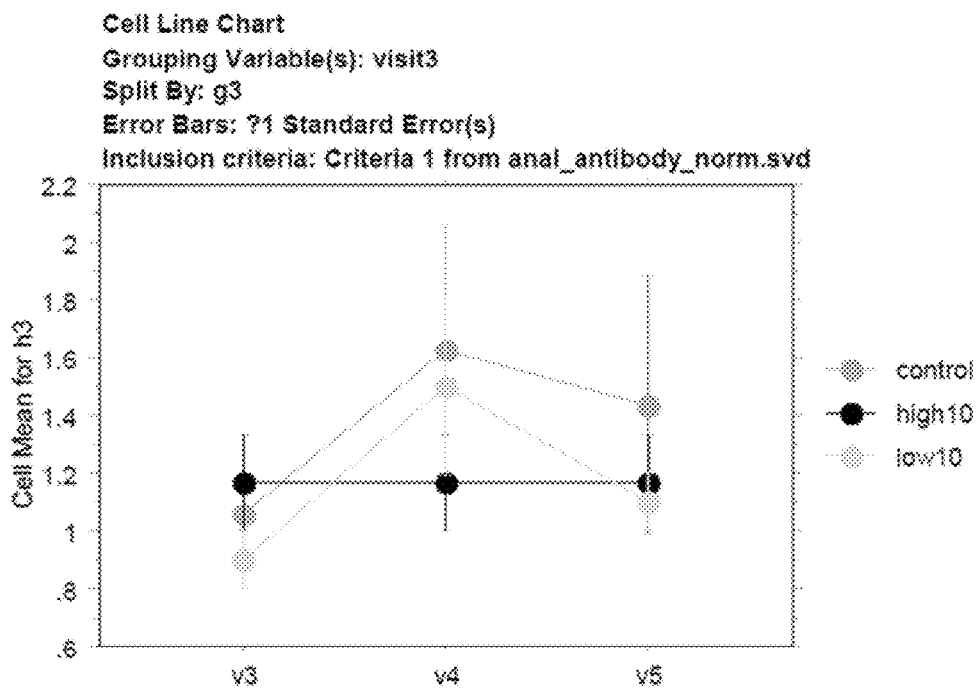
FIG. 64 shows a graph illustrating results of the antibody titer for the control group, and high performer group, and the lower performer group in the time of each visiting V3, V4, and V5 in H3N2[A/HongKong/2671/2019].
Figure 65:
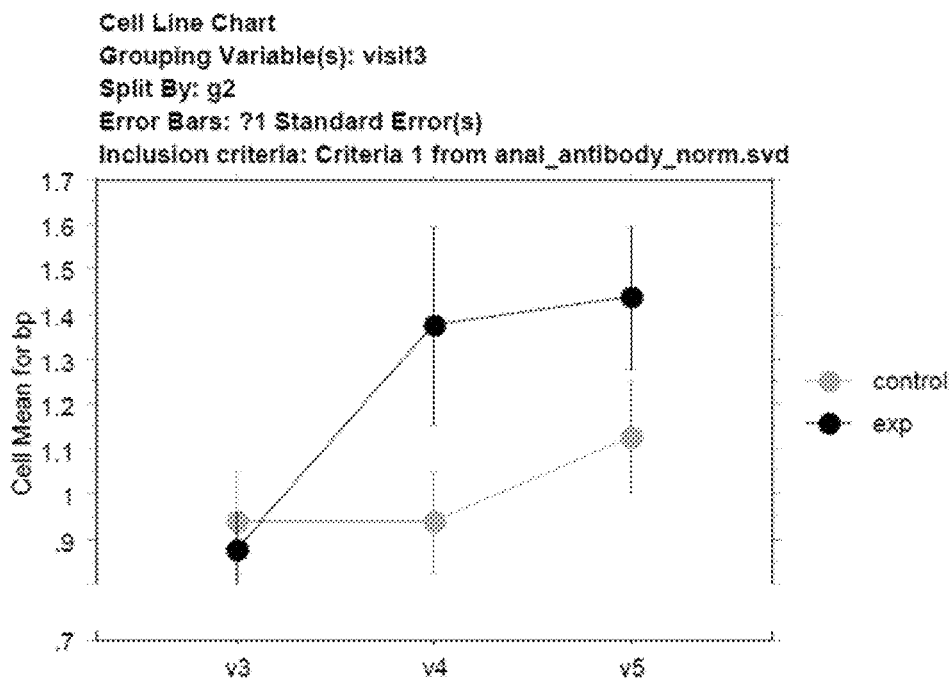
FIG. 65 shows a graph illustrating results of the antibody titer for the control group and the experimental group in the time of each visiting V3, V4, and V5 in B[B/Phuket/3073/2013].
Figure 66:
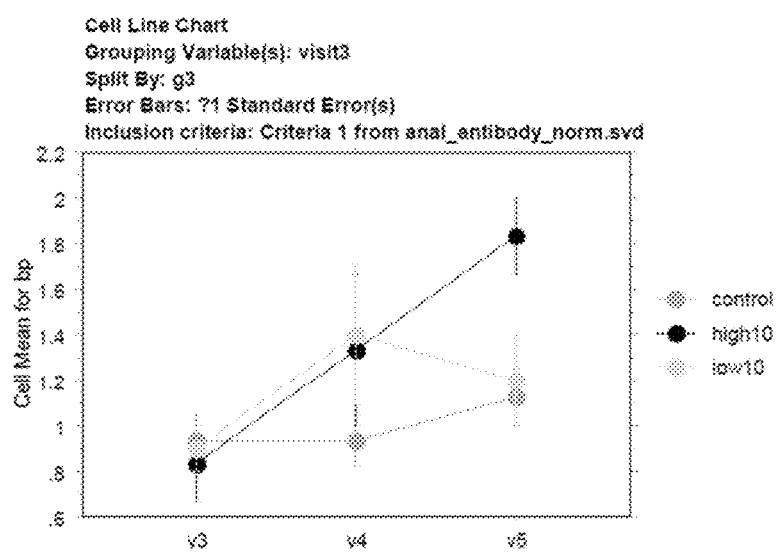
FIG. 66 shows a graph illustrating results of the antibody titer for the control group, and high performer group, and the lower performer group in the time of each visiting V3, V4, and V5 in B[B/Phuket/3073/2013].
Figure 67:
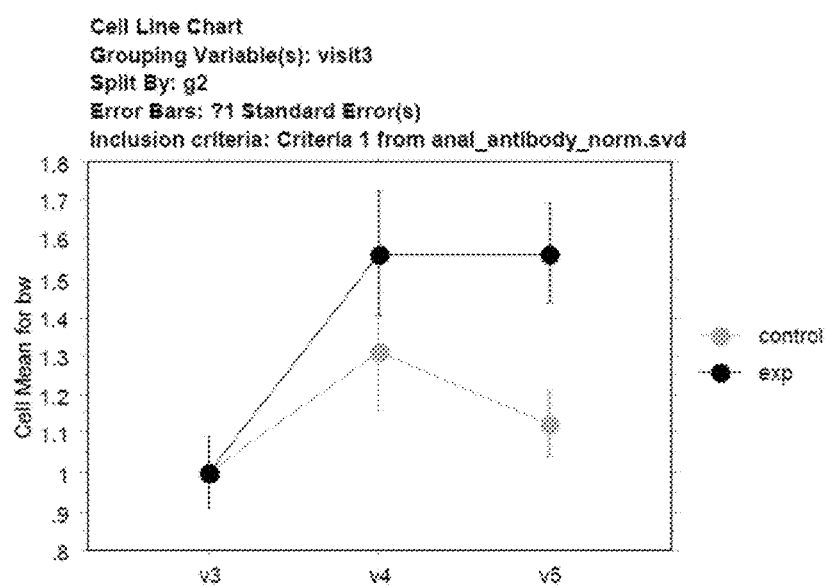
FIG. 67 shows a graph illustrating results of the antibody titer for the control group and the experimental group in the time of each visiting V3, V4, and V5 in B[B/Washington/02/2019].
Figure 68:
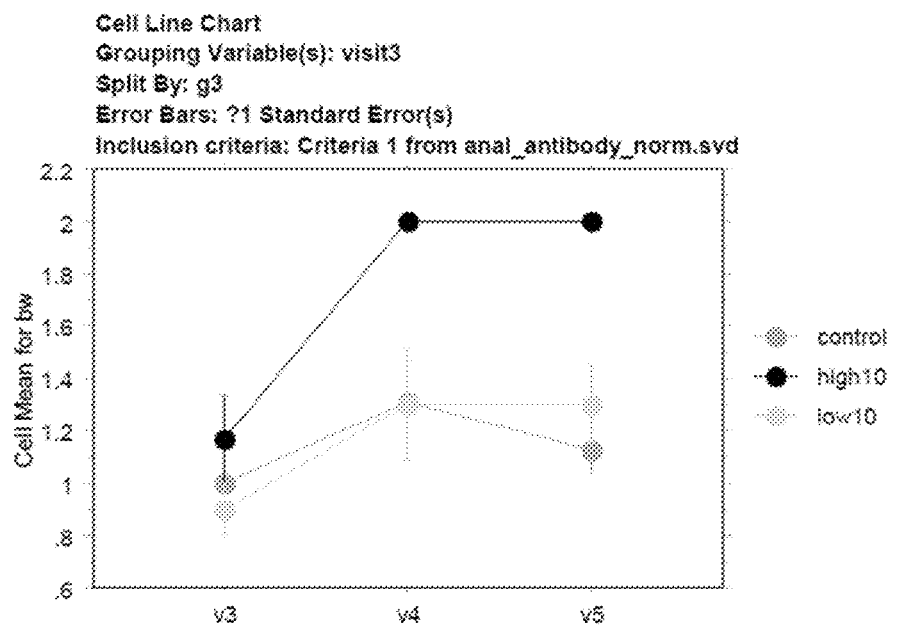
FIG. 68 shows a graph illustrating results of the antibody titer for the control group, and high performer group, and the lower performer group in the time of each visiting V3, V4, and V5 in B[B/Washington/02/2019].

FIG. 47 shows the difference of NK cells populations among groups in the time of each visiting (V3) (1 week), V4 (5 weeks), V5 (13 weeks) (Anova analysis). NK cell population decreased at Visit 5 compared to Visit 4 in control group, while there was no significant change between Visit 4 and Visit 5 in High Performers and Low Performers. According to the statistical analysis, Naive CD4 T cell showed significant group effect in V4 and V5 as shown in FIG. 48, Central CD4 T cell showed significant visit effect as shown in FIG. 49, Effector CD 4 cell showed significant visit effect and group effect in V4 as shown in FIG. 50, and Effector Memory CD 4 cell showed significant visit group interaction and visit effect as shown in FIG. 51. According to the statistical analysis, Naive CD8 T cell showed significant visit effect in control group as shown in FIG. 52, Central CD8 T cell showed significant visit effect as shown in FIG. 53, effector CD8 T cell showed significant visit effect and group effect as shown in FIG. 54, and effector CD8 T cell showed significant visit group interaction as shown in FIG. 55. FIGS. 56 and 57 showed the results of the difference of CD4 Treg (CD25+Foxp3+) cells populations among groups in the time of each visiting V3 (1 week), V4 (5 weeks), V5 (13 weeks) (t-test, $P<0.01$). The difference of populations of CD4 Treg cells was not significant between control group and experimental group significantly as shown in FIG. 56. CD4 Treg cells had a trend of increasing relevantly with visits and there is significant increasing of populations in high adherence group ($t=-4.25$, $P<0.01$) as shown in FIG. 57. FIG. 58 showed the results of the difference of Naive B cells populations among groups in the time of each visiting V3 (1 week), V4 (5 weeks), V5 (13 weeks) (t-test, $P<0.05$). The difference of populations of Naive B cells was not significant between control group and experimental group. FIG. 59 showed the results of the difference of Memory B cells populations among groups in the time of each visiting V3 (1 week), V4 (5 weeks), V5 (13 weeks) (t-test, $P<0.05$). The difference of populations of Memory B cells are significant between control group and experimental group. FIG. 60 showed the results of the difference of plasma B cells populations among groups in the time of each visiting V3 (1 week), V4 (5 weeks), V5 (13 weeks) (t-test, $P<0.05$). The difference of populations of Plasma B cells are significant between control group and experimental group.

The antibody titer test results are shown in FIGS. 61-68. All data analysis was performed based on normalization with baseline V2. ANOVA is used to determine whether there are any statistically significant differences between the groups.

In the case of the test group, after using the digital device for research, the number and activity of immune cells increases compared to baseline, and it is observed that the test group is improved even when compared to the control group. In addition, the influenza antibody production rate and titer changes in the test group are increased compared to the control group. These results serve as the basis for evaluating that the app is effective in improving immune function.

| Abbreviation | Meaning |
|---|---|
| Ab | Antibody |
| ADE | Adverse Device Effect |
| ADR | Adverse Drug Reaction |
| AE | Adverse Event |
| AI | Artificial Intelligence |
| DCF | Data Clarification Form |
| FAS | Full Analysis Set |
| IFN-γ | Interferon-γ |
| IL-10 | Interleukin-10 |
| IL-1β | Interleukin-β |
| IL-6 | Interleukin-6 |
| IPAQ | International Physical Activity Questionnaires |
| IRB | Institutional Review Board |
| LOCF | Last Observation Carried Forward |
| MET | Metabolic Equivalent |
| MFDS | Ministry of Food and Drug Safety |
| ML | Machine Learning |
| NK cells | Natural Killer Cells |
| PPS | Per Protocol Set |
| PT | Preferred Term |
| SADE | Serious Adverse Device Effect |
| SAE | Serious Adverse Event |
| SaMD | Software as a Medical Device |
| SOC | System Organ Class |
| TEAE | Treatment-Emergent Adverse Event |
| TNF-a | Tumor necrosis factor-α |

See Appendix for additional details regarding the above-referenced clinical trial. The results show maintaining, optimizing, or strengthening an immune system of a subject using the exemplary application described herein.

While the disclosure has been shown and described with reference to certain exemplary embodiments thereof, it will be understood by those skilled in the art that various changes in form and details may be made therein without departing from the spirit and scope of the disclosure as defined by the appended claims.

In one aspect, the present disclosure relates to the following embodiments.

Embodiment 1. A digital system for maintaining, optimizing, or strengthening an immune system of a subject for a virus disease, the digital system comprising: at least one memory storing a digital program; and at least one processor configured to execute the digital program to: provide, by a digital instruction generation unit to the subject, a first exercise module for NK cell recruitment and T cell boosting, and a first vagal nerve stimulation module for B cell maturation and sIgA secretion increasing, each of the first exercise module and the first vagal nerve stimulation module comprising one or more first instructions for the subject to follow, and collect, by an outcome analysis unit, the subject's performance results on the one or more first instructions using a sensor.

Embodiment 2. The digital system of embodiment 1, wherein the virus disease includes at least one of SARS, MERS, COVID-19, influenza, respiratory tract infection, or gastrointestinal infection.

Embodiment 3. The digital system of embodiment 1, wherein the first exercise module and the first vagal nerve stimulation module are provided with a lag time therebetween.

Embodiment 4. The digital system of embodiment 3, wherein the lag time is at least 3 hours.

Embodiment 5. The digital system of embodiment 1, wherein and the first exercise module comprises instructions for moderate exercise that recruits NK cells based on a predetermined target heart rate.

Embodiment 6. The digital system of embodiment 5, wherein the predetermined target heart rate is determined based on an age of the subject and a resting heart rate of the subject.

Embodiment 7. The digital system of embodiment 1, wherein the processor is further configured to provide at least one of a second exercise module and a second vagal nerve stimulation module based on the subject's performance results on the one or more first instructions, each of the second exercise module and the second vagal nerve stimulation module comprising one or more second instructions.

Embodiment 8. The digital system of embodiment 7, wherein the second exercise module is provided, the first exercise module comprises first instructions for moderate exercise that recruits NK cells based on a first target heart rate, the second exercise module comprises second instructions for moderate exercise that recruits NK cells based on a second target heart rate, and the second target heart rate is determined based on the subject's performance results on the one or more first instructions of the first exercise module.

Embodiment 9. The digital system of embodiment 8, wherein the first exercise module comprises instructions for benchmark exercise and the second target heart rate is determined based on the subject's performance results on the one or more instructions for benchmark exercise.

Embodiment 10. The digital system of embodiment 9, wherein the instructions for benchmark exercise are provided once every two weeks.

Embodiment 11. The digital system of embodiment 9 wherein the benchmark exercise comprises one or more exercises selected from the group consisting of jumping jacks, squats, and pushups.

Embodiment 12. The digital system of embodiment 8, wherein the second target heart rate is determined based on the subject's performance results on the one or more first instructions for moderate exercise.

Embodiment 13. The digital system of embodiment 7, wherein the processor is further configured to transmits the subject's performance results on the one or more first instructions to a server, and receives the one or more second instructions from the server based on the subject's performance results on the one or more first instructions.

Embodiment 14. The digital system of embodiment 5, wherein the instructions for the first vagal nerve stimulation module are provided every day, and the instructions for moderate exercise are provided two or three times a week.

Embodiment 15. The digital system of embodiment 5, wherein the first exercise module comprises instructions for 30-minute exercise per day including 5 minutes of warm-up, 20 minutes of moderate exercise, and 5 minutes of clean-up.

Embodiment 16. The digital system of embodiment 1, wherein the first vagal nerve stimulation module comprises instructions for 10-minute practice per day including two different activities each lasting for 5 minutes.

Embodiment 17. The digital system of embodiment 16, wherein each of the two different activities is selected from the group consisting of deep breathing, listening to white noise, holding breath, aroma meditation, soaking face in cold water, and cold massage.

Embodiment 18. The digital system of embodiment 16, wherein an activity performed first between the two different activities is fixed as deep breathing.

Embodiment 19. The digital system of embodiment 1, wherein the first exercise module comprises the one or more first instructions to stimulate a sympathetic nervous system of the subject.

Embodiment 20. The digital system of embodiment 1, wherein the first exercise module comprises at least one of moderate, aerobic, or acute exercise instructions.

Embodiment 21. The digital system of embodiment 1, wherein the first vagal nerve stimulation module comprises one or more instructions selected from the group consisting of sense stimulation instructions for sight, sound, touch, taste, and smell.

Embodiment 22. The digital system of embodiment 21, wherein the first vagal nerve stimulation module comprises one or more sense stimulation instructions for sight, and the one or more sense stimulation instructions for sight include one or more instructions to view one or more figures to stimulate autonomic nervous system.

Embodiment 23. The digital system of embodiment 22, wherein the figures comprise one or more images for inducing fear in the subject.

Embodiment 24. The digital system of embodiment 21, wherein the first vagal nerve stimulation module comprises one or more sense stimulation instructions for sound, and the one or more sense stimulation instructions for sound include one or more instructions to hear one or more sounds to cause horror or relaxation.

Embodiment 25. The digital system of embodiment 21, wherein the first vagal nerve stimulation module comprises one or more sense stimulation instructions for touch, and the one or more sense stimulation instructions for touch include one or more instructions for abdominal breathing, controlling rate of breathing, holding breath, cold massage, bathing face in cold water, coughing, or skin massage.

Embodiment 26. The digital system of embodiment 21, wherein the first vagal nerve stimulation module comprises one or more sense stimulation instructions for smell, and the one or more sense stimulation instructions for smell include one or more instructions to relax.

Embodiment 27. The digital system of embodiment 26, wherein the at least one processor configured to execute the digital program so that the digital system is further configured to release a scent for aroma therapy.

Embodiment 28. The digital system of embodiment 1, wherein the at least one processor is further configured to provide at least one of the first exercise module and the first vagal nerve stimulation module based on an outcome of a health professional's prescription for the subject.

Embodiment 29. An operating method of a digital system for maintaining, optimizing, or strengthening an immune system of a subject for a virus disease, the method comprising: providing, by a digital instruction generation unit to the subject, a first exercise module for NK cell recruitment and T cell boosting, and a first vagal nerve stimulation module for B cell maturation and sIgA secretion increasing, each of the first exercise module and the first vagal nerve stimulation module comprising one or more first instructions for the subject to follow, and collecting, by an outcome analysis unit, the subject's performance results on the one or more first instructions using a sensor.

Embodiment 30. A computer-readable recording medium storing a program to execute the method of embodiment 29 on an electronic device.

In one aspect, the present disclosure relates to the following additional embodiments.

Embodiment 1. A method of maintaining, optimizing, or strengthening an immune system of a subject, the method comprising: providing, by an electronic device to the subject, a first exercise module and/or a first vagal nerve stimulation module, each of the first modules comprising one or more first instructions for the subject to follow.

Embodiment 2. The method according to Embodiment 1, wherein the method activates or increases production of natural killer (NK) cells in the subject.

Embodiment 3. The method according to Embodiment 1 or 2, wherein the method reduces a change in a number of central T cells in the subject.

Embodiment 4. The method according to any one of Embodiments 1-3, wherein the method reduces a change in a number of effector T cells in the subject.

Embodiment 5. The method according to any one of Embodiments 1-4, wherein the method reduces a change in a number of effector memory T cells in the subject.

Embodiment 6. The method according to any one of Embodiments 1-5, wherein the method activates or increases production of naïve CD4 T cells in the subject.

Embodiment 7. The method according to Embodiment 6, wherein the naïve T cells are activated or increased within one month from the providing.

Embodiment 8. The method according to any one of Embodiments 1-7, wherein the method reduces a change in a number of central CD4 T cells in the subject.

Embodiment 9. The method according to any one of Embodiments 1-8, wherein the method reduces a change in a number of effector CD4 T cells in the subject.

Embodiment 10. The method according to any one of Embodiments 1-9, wherein the method reduces a change in a number of effector memory CD4 T cells in the subject.

Embodiment 11. The method according to any one of Embodiments 1-10, wherein the method reduces a change in a number of naive CD8 T cells in the subject.

Embodiment 12. The method according to any one of Embodiments 1-11, wherein the method reduces a change in a number of central CD8 T cells in the subject.

Embodiment 13. The method according to any one of Embodiments 1-12, wherein the method reduces a change in a number of effector CD8 T cells in the subject.

Embodiment 14. The method according to any one of Embodiments 1-13, wherein the method reduces a change in a number of effector memory CD8 T cells in the subject.

Embodiment 15. The method according to any one of Embodiments 1-14, wherein the method activates or increases production of CD4 Treg cells in the subject.

Embodiment 16. The method according to any one of Embodiments 1-15, wherein the method activates naïve B cells into maturation in the subject.

Embodiment 17. The method according to any one of Embodiments 1-16, wherein the method increases naïve B cells in the subject.

Embodiment 18. The method according to any one of Embodiments 1-17, wherein the method increases memory B cells in the subject.

Embodiment 19. The method according to any one of Embodiments 1-18, wherein the method decreases plasma B cells in the subject.

Embodiment 20. The method according to any one of Embodiments 1-19, further providing, by the electronic device to the subject, a second exercise module and/or a second vagal nerve stimulation module, each of the second modules comprising one or more second instructions, wherein the electronic device (i) comprises a sensor sensing adherence by the subject to the first instructions of the first modules, (ii) transmits adherence information, based on the adherence, to a server, and (iii) receives the one or more second instructions from the server based on the adherence information.

Embodiment 21. The method according to any one of Embodiments 1-20, wherein the first exercise module and the first vagal nerve stimulation module are provided with a lag time of at least 3 hours.

Embodiment 22. The method according to any one of Embodiments 1-21, wherein the first exercise module is provided, and the exercise module comprises one or more first instructions to stimulate a parasympathetic nervous system of the subject.

Embodiment 23. The method according to any one of Embodiments 1-22, wherein the first exercise module is provided, and the first exercise module comprises at least one of moderate, aerobic and acute exercise instructions.

Embodiment 24. The method according to Embodiment 23, wherein the first exercise module comprising moderate exercise instructions is provided, and maintaining, optimizing, or strengthening an immune system of the subject comprises stimulating NK cells.

Embodiment 25. The method according to any one of Embodiments 1-24, wherein moderate exercise is determined based on at least age and/or target heart rate.

Embodiment 26. The method according to Embodiment 25, wherein moderate exercise for an about 15 year old subject comprises a target heart rate of between about 126 and about 150 beats per minute (bpm), moderate exercise for an about 20 year old subject comprises a target heart rate of between about 124 and about 147 bpm, moderate exercise for an about 25 year old subject comprises a target heart rate of between about 122 and about 145 bpm, moderate exercise for an about 30 year old subject comprises a target heart rate of between about 120 and about 142 bpm, moderate exercise for an about 35 year old subject comprises a target heart rate of between about 117 and about 139 bpm, moderate exercise for an about 40 year old subject comprises a target heart rate of between about 115 and about 137 bpm, moderate exercise for an about 45 year old subject comprises a target heart rate of between about 113 and about 134 bpm, moderate exercise for an about 50 year old subject comprises a target heart rate of between about 111 and about 132 bpm, moderate exercise for an about 55 year old subject comprises a target heart rate of between about 109 and about 129 bpm, moderate exercise for an about 60 year old subject comprises a target heart rate of between about 107 and about 127 bpm, moderate exercise for an about 65 year old subject comprises a target heart rate of between about 105 and about 124 bpm, moderate exercise for an about 70 year old subject comprises a target heart rate of between about 102 and about 122 bpm, moderate exercise for an about 75 year old subject comprises a target heart rate of between about 100 and about 119 bpm, moderate exercise for an about 80 year old subject comprises a target heart rate of between about 98 and about 117 bpm, moderate exercise for an about 85 year old subject comprises a target heart rate of between about 96 and about 114, and moderate exercise for an about 95 year old subject comprises a target heart rate of between about 92 and about 109.

Embodiment 27. The method according to Embodiment 25 or 26, wherein the target heart rate is determined, at least in part, based on feedback from exercise performed prior to the providing.

Embodiment 28. The method according to Embodiment 27, wherein an increase in the subject's heart rate by greater than 1 bpm, greater than 2 bpm, greater than 3 bpm, greater than 4 bpm, greater than 5 bpm, greater than 6 bpm, greater than 7 bpm, greater than 8 bpm, greater than 9 bpm, greater than 10 bpm, greater than 15 bpm, or greater than 20 bpm relative to the target heart rate for the moderate exercise module results in a decrease in the target heart rate for a subsequent moderate exercise module.

Embodiment 29. The method according to Embodiment 27, wherein a decrease in the subject's heart rate by greater than 1 bpm, greater than 2 bpm, greater than 3 bpm, greater than 4 bpm, greater than 5 bpm, greater than 6 bpm, greater than 7 bpm, greater than 8 bpm, greater than 9 bpm, greater than 10 bpm, greater than 15 bpm, or greater than 20 bpm relative to the target heart rate for the moderate exercise module results in an increase in the target heart rate for a subsequent moderate exercise module.

Embodiment 30. The method according to any one of Embodiments 1-29, wherein moderate exercise is determined based on at least one of a heart rate (HR), a repetition maximum (RM), metabolic equivalents (METs), a maximal oxygen uptake capacity ($VO_{2max}$)/oxygen uptake reverse ($VO_2R$), or a rating of perceived exertion (RPE).

Embodiment 31. The method according to any one of Embodiments 1-30, wherein the first exercise module comprising aerobic exercise and/or acute exercise instructions is provided, and maintaining, optimizing, or strengthening an immune system of the subject comprises T cell boosting.

Embodiment 32. The method according to any one of Embodiments 1-31, wherein the first exercise module comprising aerobic exercise and/or acute exercise instructions is provided, and a level of the aerobic exercise and/or the acute exercise is determined prior to the providing.

Embodiment 33. The method according to any one of Embodiments 1-32, wherein the first exercise module comprising aerobic exercise and/or acute exercise instructions is provided, and a level of the aerobic exercise and/or the acute exercise is determined based on at least one of a HR, a RM, METs, a $VO_{2max}$/$VO_2R$, or a RPE.

Embodiment 34. The method according to any one of Embodiments 1-33, wherein the first exercise module comprising aerobic exercise instructions is provided, and maintaining, optimizing, or strengthening an immune system of the subject comprises emerging CD4+ T cells to activate the immune system.

Embodiment 35. The method according to any one of Embodiments 1-34, wherein the first exercise module comprising acute exercise instructions is provided, and maintaining, optimizing, or strengthening an immune system of the subject comprises removing pre-existing T cells to secure T cells zone for new T cells.

Embodiment 36. The method according any one of Embodiments 1-35, wherein the first exercise module comprises at least one first exercise instructions for simultaneous aerobic and acute exercise.

Embodiment 37. The method according to any one of Embodiments 1-36, wherein said one or more first instructions comprise instructions for resistance exercise, concurrent exercise, and/or benchmark exercise.

Embodiment 38. The method according to Embodiment 37, wherein the benchmark exercise comprises one or more selected from the group consisting of jumping jacks, squats, and pushups.

Embodiment 39. The method according to Embodiment 37 or 38, further comprising repeating the benchmark exercise at least one times in succession.

Embodiment 40. The method according to any one of Embodiments 1-39, wherein said one or more first instructions comprise one or more instructions for walking, biking, aerobic dance and/or swimming.

Embodiment 41. The method according to any one of Embodiments 1-40, wherein the first vagal nerve stimulation module is provided, and the vagal nerve stimulation module comprises one or more first instructions to stimulate a sympathetic nervous system of the subject.

Embodiment 42. The method according to Embodiment 41, wherein maintaining, optimizing, or strengthening an immune system of the subject comprises accelerating maturation of B-cells and/or differentiation of B cells to plasma cells.

Embodiment 43. The method according to Embodiment 41 or 42, wherein maintaining, optimizing, or strengthening an immune system of the subject comprises increasing a number responsive cells of the subject's immune system.

Embodiment 44. The method according to any one of Embodiments 1-43, wherein the first vagal nerve stimulation module is provided, and the vagal nerve stimulation module comprises at least one instructions selected from the group consisting of sense stimulation instructions for sight, sound, touch, taste, and smell.

Embodiment 45. The method according to Embodiment 44, wherein the vagal nerve stimulation module comprises one or more sense stimulation instructions for sight, and the one or more sense stimulation instructions for sight include one or more instructions to view one or more figures to stimulate autonomic nervous system.

Embodiment 46. The method according to Embodiment 45, wherein the electronic device receives and displays the figures.

Embodiment 47. The method according to Embodiment 45 or 46, wherein the figures comprise one or more images for inducing fear in the subject.

Embodiment 48. The method according to any one of Embodiments 44-47, wherein the vagal nerve stimulation module comprises one or more sense stimulation instructions for sound, and the one or more sense stimulation instructions for sound include one or more instructions to hear one or more sounds to cause horror or relaxation.

Embodiment 49. The method according to Embodiment 48, wherein the one or more sounds to cause relaxation comprise white noise.

Embodiment 50. The method according to Embodiment 48 or 49, wherein the electronic device receives and plays the sounds.

Embodiment 51. The method according to any one of Embodiments 44-50, wherein the vagal nerve stimulation module comprises one or more sense stimulation instructions for touch, and the one or more sense stimulation instructions for touch include one or more instructions for abdominal breathing, controlling rate of breathing, holding breath, cold massage, bathing face in cold water, coughing, and skin massage.

Embodiment 52. The method according to any one of Embodiments 44-51, wherein the vagal nerve stimulation module comprises one or more sense stimulation instructions for touch, and the one or more sense stimulation instructions for touch include one or more instructions for controlling rate of breathing.

Embodiment 53. The method according to any one of Embodiments 44-52, wherein the vagal nerve stimulation module comprises one or more sense stimulation instructions for smell, and the one or more sense stimulation instructions for smell include one or more instructions to relax.

Embodiment 54. The method according to any one of Embodiments 1-53, wherein the electronic device is configured to release a scent for aroma therapy.

Embodiment 55. The method according to any one of Embodiments 1-54, wherein the subject is less than or equal to about 45 years old.

Embodiment 56. The method according to Embodiment 55, wherein the first exercise module is provided prior to the first vagal nerve stimulation module.

Embodiment 57. The method according to any one of Embodiments 20-56, wherein the server receives the one or more second instructions from an external reviewer.

Embodiment 58. The method according to Embodiment 57, wherein the external reviewer comprises a health professional.

Embodiment 59. The method according to Embodiment 58, wherein the external reviewer comprises an artificial intelligence (AI).

Embodiment 60. The method according to any one of Embodiments 20-59, wherein the sensor comprises one or more of: a camera, an accelerometer, a magnetometer, a light sensor, a microphone, a proximity sensor, a touch sensor, a gyroscope, a Global Positioning System (GPS) sensor, an ambient light sensor, a fingerprint sensor, a pedometer, a heart rate sensor, a motion sensor, and a thermometer.

Embodiment 61. The method according to any one of Embodiments 20-60, wherein the sensor comprises a touch sensor, and wherein the subject provides the adherence information to the electronic device using the touch sensor.

Embodiment 62. The method according to any one of Embodiments 20-61, wherein the sensor comprises a motion sensor or an accelerometer, and wherein the device detects the adherence information using the motion sensor or the accelerometer.

Embodiment 63. The method according to any one of Embodiments 20-62, wherein the electronic device is selected from the group consisting of a smart phone, a smart watch, smart jewelry, and a head mounted display.

Embodiment 64. The method according to any one of Embodiments 1-63, further comprising repeating the method 2 times per week, 3 times per week, or more than 3 times per week.

Embodiment 65. The method according to any one of Embodiments 1-64, wherein the method treats or prevent a disease in the subject.

Embodiment 66. A system for maintaining, optimizing, or strengthening an immune system of a subject, comprising: an electronic device configured to execute a digital application comprising a first exercise module and/or a first vagal nerve stimulation module, for maintaining, optimizing, or strengthening an immune system of a subject; a healthcare provider portal configured to provide one or more options to a healthcare provider to perform one or more tasks to prescribe treatment for maintaining, optimizing, or strengthening an immune system of the subject based on information received from the digital application; and an administrative portal configured to provide one or more options to an administrator of the system to perform one or more tasks to manage access to the system by the healthcare provider.

Embodiment 67. The system according to Embodiment 66, wherein said maintaining, optimizing, or strengthening the immune system activates or increases production of natural killer (NK) cells in the subject.

Embodiment 68. The system according to Embodiment 66 or 67, wherein maintaining, optimizing, or strengthening the immune system reduces a change in a number of central T cells in the subject.

Embodiment 69. The system according to any one of Embodiments 66-68, wherein maintaining, optimizing, or strengthening the immune system reduces a change in a number of effector T cells in the subject.

Embodiment 70. The system according to any one of Embodiments 66-69, wherein maintaining, optimizing, or strengthening the immune system reduces a change in a number of effector memory T cells in the subject.

Embodiment 71. The system according to any one of Embodiments 66-70, wherein maintaining, optimizing, or strengthening the immune system activates or increases production of naïve CD4 T cells in the subject.

Embodiment 72. The system according to Embodiment 71, wherein the naïve T cells are activated or increased within one month from the providing.

Embodiment 73. The system according to any one of Embodiments 66-72, wherein maintaining, optimizing, or strengthening the immune system reduces a change in a number of central CD4 T cells in the subject.

Embodiment 74. The system according to any one of Embodiments 66-73, wherein maintaining, optimizing, or strengthening the immune system reduces a change in a number of effector CD4 T cells in the subject.

Embodiment 75. The system according to any one of Embodiments 66-74, wherein maintaining, optimizing, or strengthening the immune system reduces a change in a number of effector memory CD4 T cells in the subject.

Embodiment 76. The system according to any one of Embodiments 66-75, wherein maintaining, optimizing, or strengthening the immune system reduces a change in a number of naive CD8 T cells in the subject.

Embodiment 77. The system according to any one of Embodiments 66-76, wherein maintaining, optimizing, or strengthening the immune system reduces a change in a number of central CD8 T cells in the subject.

Embodiment 78. The system according to any one of Embodiments 66-77, wherein maintaining, optimizing, or strengthening the immune system reduces a change in a number of effector CD8 T cells in the subject.

Embodiment 79. The system according to any one of Embodiments 66-78, wherein maintaining, optimizing, or strengthening the immune system reduces a change in a number of effector memory CD8 T cells in the subject.

Embodiment 80. The system according to any one of Embodiments 66-79, wherein maintaining, optimizing, or strengthening the immune system activates or increases production of CD4 Treg cells in the subject.

Embodiment 81. The system according to any one of Embodiments 66-80, wherein maintaining, optimizing, or strengthening the immune system activates naïve B cells into maturation in the subject.

Embodiment 82. The system according to any one of Embodiments 66-81, wherein maintaining, optimizing, or strengthening the immune system increases naïve B cells in the subject.

Embodiment 83. The system according to any one of Embodiments 66-82, wherein maintaining, optimizing, or strengthening the immune system increases memory B cells in the subject.

Embodiment 84. The system according to any one of Embodiments 66-83, wherein maintaining, optimizing, or strengthening the immune system decreases plasma B cells in the subject.

Embodiment 85. The system according to any one of Embodiments 66-84, wherein the digital application instructs a processor of the electronic device to execute operations comprising: generating digital therapeutic modules comprising the first exercise module and/or the first vagal nerve stimulation module for maintaining, optimizing, or strengthening an immune system based on age and/or target heart rate.

Embodiment 86. The system according to any one of Embodiments 66-85, wherein the electronic device or another electronic device is further configured to execute a digital application comprising a second exercise module and/or a second vagal nerve stimulation module for maintaining, optimizing, or strengthening an immune system of a subject, each of the second modules comprising one or more second instructions, wherein the electronic device (i) comprises a sensor sensing adherence by the subject to the first instructions of the first modules, (ii) transmits adherence information, based on the adherence, to a server, and (iii) receives the one or more second instructions from the server based on the adherence information.

Embodiment 87. The system according to any one of Embodiments 66-86, wherein the first exercise module and the first vagal nerve stimulation module are provided with a lag time of at least 3 hours.

Embodiment 88. The system according to any one of Embodiments 66-87, wherein the first exercise module is provided, and the exercise module comprises one or more first instructions to stimulate a parasympathetic nervous system of the subject.

Embodiment 89. The system according to any one of Embodiments 66-88, wherein the first exercise module is provided, and the first exercise module comprises at least one of moderate, aerobic and acute exercise instructions.

Embodiment 90. The system according to Embodiment 89, wherein the first exercise module comprising moderate exercise instructions is provided, and maintaining, optimizing, or strengthening an immune system of the subject comprises stimulating NK cells.

Embodiment 91. The system according to any one of Embodiment 90, wherein moderate exercise is determined based on at least age and/or target heart rate.

Embodiment 92. The system according to Embodiment 91, wherein moderate exercise for an about 15 year old subject comprises a target heart rate of between about 126 and about 150 beats per minute (bpm), moderate exercise for an about 20 year old subject comprises a target heart rate of between about 124 and about 147 bpm, moderate exercise for an about 25 year old subject comprises a target heart rate of between about 122 and about 145 bpm, moderate exercise for an about 30 year old subject comprises a target heart rate of between about 120 and about 142 bpm, moderate exercise for an about 35 year old subject comprises a target heart rate of between about 117 and about 139 bpm, moderate exercise for an about 40 year old subject comprises a target heart rate of between about 115 and about 137 bpm, moderate exercise for an about 45 year old subject comprises a target heart rate of between about 113 and about 134 bpm, moderate exercise for an about 50 year old subject comprises a target heart rate of between about 111 and about 132 bpm, moderate exercise for an about 55 year old subject comprises a target heart rate of between about 109 and about 129 bpm, moderate exercise for an about 60 year old subject comprises a target heart rate of between about 107 and about 127 bpm, moderate exercise for an about 65 year old subject comprises a target heart rate of between about 105 and about 124 bpm, moderate exercise for an about 70 year old subject comprises a target heart rate of between about 102 and about 122 bpm, moderate exercise for an about 75 year old subject comprises a target heart rate of between about 100 and about 119 bpm, moderate exercise for an about 80 year old subject comprises a target heart rate of between about 98 and about 117 bpm, moderate exercise for an about 85 year old subject comprises a target heart rate of between about 96 and about 114, and moderate exercise for an about 95 year old subject comprises a target heart rate of between about 92 and about 109.

Embodiment 93. The system according to Embodiment 91 or 92, wherein the target heart rate is determined, at least in part, based on feedback from exercise performed prior to the providing.

Embodiment 94. The system according to Embodiment 93, wherein an increase in the subject's heart rate by greater than 1 bpm, greater than 2 bpm, greater than 3 bpm, greater than 4 bpm, greater than 5 bpm, greater than 6 bpm, greater than 7 bpm, greater than 8 bpm, greater than 9 bpm, greater than 10 bpm, greater than 15 bpm, or greater than 20 bpm relative to the target heart rate for the moderate exercise module results in a decrease in the target heart rate for a subsequent moderate exercise module.

Embodiment 95. The system according to Embodiment 93, wherein a decrease in the subject's heart rate by greater than 1 bpm, greater than 2 bpm, greater than 3 bpm, greater than 4 bpm, greater than 5 bpm, greater than 6 bpm, greater than 7 bpm, greater than 8 bpm, greater than 9 bpm, greater than 10 bpm, greater than 15 bpm, or greater than 20 bpm relative to the target heart rate for the moderate exercise module results in an increase in the target heart rate for a subsequent moderate exercise module.

Embodiment 96. The system according to any one of Embodiments 66-95, wherein moderate exercise is determined based on at least one of a heart rate (HR), a repetition maximum (RM), metabolic equivalents (METs), a maximal oxygen uptake capacity ($VO_{2max}$)/oxygen uptake reverse ($VO_2R$), or a rating of perceived exertion (RPE).

Embodiment 97. The system according to any one of Embodiments 66-96, wherein the first exercise module comprising aerobic exercise and/or acute exercise instructions is provided, and maintaining, optimizing, or strengthening an immune system of the subject comprises T cell boosting.

Embodiment 98. The system according to any one of Embodiments 66-97, wherein the first exercise module comprising aerobic exercise and/or acute exercise instructions is provided, and a level of the aerobic exercise and/or the acute exercise is determined prior to the providing.

Embodiment 99. The system according to any one of Embodiments 66-98, wherein the first exercise module comprising aerobic exercise and/or acute exercise instructions is provided, and a level of the aerobic exercise and/or the acute exercise is determined based on at least one of a HR, a RM, METs, a $VO_{2max}$/$VO_2R$, or a RPE.

Embodiment 100. The system according to any one of Embodiments 66-99, wherein the first exercise module comprising aerobic exercise instructions is provided, and maintaining, optimizing, or strengthening an immune system of the subject comprises emerging CD4+ T cells to activate the immune system.

Embodiment 101. The system according to any one of Embodiments 66-100, wherein the first exercise module comprising acute exercise instructions is provided, and maintaining, optimizing, or strengthening an immune system of the subject comprises removing pre-existing T cells to secure T cells zone for new T cells.

Embodiment 102. The system according to any one of Embodiments 66-101, wherein the first exercise module comprises at least one first exercise instructions for simultaneous aerobic and acute exercise.

Embodiment 103. The system according to any one of Embodiments 66-102, wherein said one or more first instructions comprise instructions for resistance exercise, concurrent exercise, and/or benchmark exercise.

Embodiment 104. The system according to Embodiment 103, wherein the benchmark exercise comprises one or more selected from the group consisting of jumping jacks, squats, and pushups.

Embodiment 105. The system according to Embodiment 103 or 104, further comprising repeating the benchmark exercise at least one times in succession.

Embodiment 106. The system according to any one of Embodiments 66-105, wherein said one or more first instructions comprise one or more instructions for walking, biking, aerobic dance and/or swimming.

Embodiment 107. The system according to any one of Embodiments 66-106, wherein the first vagal nerve stimulation module is provided, and the vagal nerve stimulation module comprises one or more first instructions to stimulate a sympathetic nervous system of the subject.

Embodiment 108. The system according to Embodiment 107, wherein maintaining, optimizing, or strengthening an immune system of the subject comprises accelerating maturation of B-cells and/or differentiation of B cells to plasma cells.

Embodiment 109. The system according to Embodiment 107 or 108, wherein maintaining, optimizing, or strengthening an immune system of the subject comprises increasing a number responsive cells of the subject's immune system.

Embodiment 110. The system according to any one of Embodiments 66-109, wherein the first vagal nerve stimulation module is provided, and the vagal nerve stimulation module comprises at least one instruction selected from the group consisting of sense stimulation instructions for sight, sound, touch, taste, and smell.

Embodiment 111. The system according to Embodiment 110, wherein the vagal nerve stimulation module comprises one or more sense stimulation instructions for sight, and the one or more sense stimulation instructions for sight include one or more instructions to view one or more figures to stimulate autonomic nervous system.

Embodiment 112. The system according to Embodiment 111, wherein the electronic device receives and displays the figures.

Embodiment 113. The system according to Embodiment 111 or 112, wherein the figures comprise one or more images for inducing fear in the subject.

Embodiment 114. The system according to any one of Embodiments 110-113, wherein the vagal nerve stimulation module comprises one or more sense stimulation instructions for sound, and the one or more sense stimulation instructions for sound include one or more instructions to hear one or more sounds to cause horror or relaxation.

Embodiment 115. The system according to Embodiment 114, wherein the one or more sounds to cause relaxation comprise white noise.

Embodiment 116. The system according to Embodiment 114 or 115, wherein the electronic device receives and plays the sounds.

Embodiment 117. The system according to any one of Embodiments 110-116, wherein the vagal nerve stimulation module comprises one or more sense stimulation instructions for touch, and the one or more sense stimulation instructions for touch include one or more instructions for abdominal breathing, controlling rate of breathing, holding breath, cold massage, bathing face in cold water, coughing, and skin massage.

Embodiment 118. The system according to any one of Embodiments 110-117, wherein the vagal nerve stimulation module comprises one or more sense stimulation instructions for touch, and the one or more sense stimulation instructions for touch include one or more instructions for controlling rate of breathing.

Embodiment 119. The system according to any one of Embodiments 110-118, wherein the vagal nerve stimulation module comprises one or more sense stimulation instructions for smell, and the one or more sense stimulation instructions for smell include one or more instructions to relax.

Embodiment 120. The system according to any one of Embodiments 66-119, wherein the electronic device is configured to release a scent for aroma therapy.

Embodiment 121. The system according to any one of Embodiments 66-120, wherein the subject is less than or equal to about 45 years old.

Embodiment 122. The system according to Embodiment 121, wherein the first exercise module is provided prior to the first vagal nerve stimulation module.

Embodiment 123. The system according to any one of Embodiments 66-122, wherein the server receives the one or more second instructions from an external reviewer.

Embodiment 124. The system according to Embodiment 123, wherein the external reviewer comprises a health professional.

Embodiment 125. The system according to Embodiment 124, wherein the external reviewer comprises an artificial intelligence (AI).

Embodiment 126. The system according to any one of Embodiments 66-125, wherein the sensor comprises one or more of: a camera, an accelerometer, a magnetometer, a light sensor, a microphone, a proximity sensor, a touch sensor, a gyroscope, a Global Positioning System (GPS) sensor, an ambient light sensor, a fingerprint sensor, a pedometer, a heart rate sensor, a motion sensor, and a thermometer.

Embodiment 127. The system according to any one of Embodiments 66-126, wherein the sensor comprises a touch sensor, and wherein the subject provides the adherence information to the electronic device using the touch sensor.

Embodiment 128. The system according to any one of Embodiments 66-127, wherein the sensor comprises a motion sensor or an accelerometer, and wherein the device detects the adherence information using the motion sensor or the accelerometer.

Embodiment 129. The system according to any one of Embodiments 66-128, wherein the electronic device is selected from the group consisting of a smart phone, a smart watch, smart jewelry, and ahead mounted display.

Embodiment 130. The system according to any one of Embodiments 66-129, further comprising repeating a method using the system 2 times per week, 3 times per week, or more than 3 times per week.

Embodiment 131. A computing system for maintaining, optimizing, or strengthening an immune system of a subject in need thereof, comprising: a display configured to provide, to the subject, a first exercise module and/or a first vagal nerve stimulation module, each of the first modules comprising one or more first instructions for the subject to follow; a transmitter configured to transmit adherence information to a server; and a receiver configured to receive, from the server, one or more second instructions based on the adherence information, wherein the display is further configured to provide, to the subject, a second exercise module and/or a second vagal nerve stimulation module, each of the second modules comprising the one or more second instructions.

Embodiment 132. The computing system according to Embodiment 131, wherein said maintaining, optimizing, or strengthening the immune system activates or increases production of natural killer (NK) cells in the subject.

Embodiment 133. The computing system according to Embodiment 131 or 132, wherein maintaining, optimizing, or strengthening the immune system reduces a change in a number of central T cells in the subject.

Embodiment 134. The computing system according to any one of Embodiments 131-133, wherein maintaining, optimizing, or strengthening the immune system reduces a change in a number of effector T cells in the subject.

Embodiment 135. The computing system according to any one of Embodiments 131-134, wherein maintaining, optimizing, or strengthening the immune system reduces a change in a number of effector memory T cells in the subject.

Embodiment 136. The computing system according to any one of Embodiments 131-135, wherein maintaining, optimizing, or strengthening the immune system activates or increases production of naïve CD4 T cells in the subject.

Embodiment 137. The computing system according to Embodiment 136, wherein the naïve T cells are activated or increased within one month from the providing.

Embodiment 138. The computing system according to any one of Embodiments 131-137, wherein maintaining, optimizing, or strengthening the immune system reduces a change in a number of central CD4 T cells in the subject.

Embodiment 139. The computing system according to any one of Embodiments 131-138, wherein maintaining, optimizing, or strengthening the immune system reduces a change in a number of effector CD4 T cells in the subject.

Embodiment 140. The computing system according to any one of Embodiments 131-139, wherein maintaining, optimizing, or strengthening the immune system reduces a change in a number of effector memory CD4 T cells in the subject.

Embodiment 141. The computing system according to any one of Embodiments 131-140, wherein maintaining, optimizing, or strengthening the immune system reduces a change in a number of naive CD8 T cells in the subject.

Embodiment 142. The computing system according to any one of Embodiments 131-141, wherein maintaining, optimizing, or strengthening the immune system reduces a change in a number of central CD8 T cells in the subject.

Embodiment 143. The computing system according to any one of Embodiments 131-142, wherein maintaining, optimizing, or strengthening the immune system reduces a change in a number of effector CD8 T cells in the subject.

Embodiment 144. The computing system according to any one of Embodiments 131-143, wherein maintaining, optimizing, or strengthening the immune system reduces a change in a number of effector memory CD8 T cells in the subject.

Embodiment 145. The computing system according to any one of Embodiments 131-144, wherein maintaining, optimizing, or strengthening the immune system activates or increases production of CD4 Treg cells in the subject.

Embodiment 146. The computing system according to any one of Embodiments 131-145, wherein maintaining, optimizing, or strengthening the immune system activates naïve B cells into maturation in the subject.

Embodiment 147. The computing system according to any one of Embodiments 131-146, wherein maintaining, optimizing, or strengthening the immune system increases naïve B cells in the subject.

Embodiment 148. The computing system according to any one of Embodiments 131-147, wherein maintaining, optimizing, or strengthening the immune system increases memory B cells in the subject.

Embodiment 149. The computing system according to any one of Embodiments 131-148, wherein maintaining, optimizing, or strengthening the immune system decreases plasma B cells in the subject.

Embodiment 150. The computing system according to any one of Embodiments 131-149, further comprising a sensor configured to sense adherence by the subject to the instructions of the first modules and generate adherence information.

Embodiment 151. The computing system according to any one of Embodiments 131-150, wherein the first exercise module and the first vagal nerve stimulation module are provided with a lag time of at least 3 hours.

Embodiment 152. The computing system according to any one of Embodiments 131-151, wherein the first exercise module is provided, and the exercise module comprises one or more first instructions to stimulate a parasympathetic nervous system of the subject.

Embodiment 153. The computing system according to any one of Embodiments 131-152, wherein the first exercise module is provided, and the first exercise module comprises at least one of moderate, aerobic and acute exercise instructions.

Embodiment 154. The computing system according to Embodiment 153, wherein the first exercise module comprising moderate exercise instructions is provided, and maintaining, optimizing, or strengthening an immune system of the subject comprises stimulating NK cells.

Embodiment 155. The computing system according to any one of Embodiments 131-154, wherein moderate exercise is determined based on at least age and/or target heart rate.

Embodiment 156. The computing system according to Embodiment 155, wherein moderate exercise for an about 15 year old subject comprises a target heart rate of between about 126 and about 150 beats per minute (bpm), moderate exercise for an about 20 year old subject comprises a target heart rate of between about 124 and about 147 bpm, moderate exercise for an about 25 year old subject comprises a target heart rate of between about 122 and about 145 bpm, moderate exercise for an about 30 year old subject comprises a target heart rate of between about 120 and about 142 bpm, moderate exercise for an about 35 year old subject comprises a target heart rate of between about 117 and about 139 bpm, moderate exercise for an about 40 year old subject comprises a target heart rate of between about 115 and about 137 bpm, moderate exercise for an about 45 year old subject comprises a target heart rate of between about 113 and about 134 bpm, moderate exercise for an about 50 year old subject comprises a target heart rate of between about 111 and about 132 bpm, moderate exercise for an about 55 year old subject comprises a target heart rate of between about 109 and about 129 bpm, moderate exercise for an about 60 year old subject comprises a target heart rate of between about 107 and about 127 bpm, moderate exercise for an about 65 year old subject comprises a target heart rate of between about 105 and about 124 bpm, moderate exercise for an about 70 year old subject comprises a target heart rate of between about 102 and about 122 bpm, moderate exercise for an about 75 year old subject comprises a target heart rate of between about 100 and about 119 bpm, moderate exercise for an about 80 year old subject comprises a target heart rate of between about 98 and about 117 bpm, moderate exercise for an about 85 year old subject comprises a target heart rate of between about 96 and about 114, and moderate exercise for an about 95 year old subject comprises a target heart rate of between about 92 and about 109.

Embodiment 157. The computing system according to Embodiment 155 or 156, wherein the target heart rate is determined, at least in part, based on feedback from exercise performed prior to the providing.

Embodiment 158. The computing system according to Embodiment 157, wherein an increase in the subject's heart rate by greater than 1 bpm, greater than 2 bpm, greater than 3 bpm, greater than 4 bpm, greater than 5 bpm, greater than 6 bpm, greater than 7 bpm, greater than 8 bpm, greater than 9 bpm, greater than 10 bpm, greater than 15 bpm, or greater than 20 bpm relative to the target heart rate for the moderate exercise module results in a decrease in the target heart rate for a subsequent moderate exercise module.

Embodiment 159. The computing system according to Embodiment 157, wherein a decrease in the subject's heart rate by greater than 1 bpm, greater than 2 bpm, greater than 3 bpm, greater than 4 bpm, greater than 5 bpm, greater than 6 bpm, greater than 7 bpm, greater than 8 bpm, greater than 9 bpm, greater than 10 bpm, greater than 15 bpm, or greater than 20 bpm relative to the target heart rate for the moderate exercise module results in an increase in the target heart rate for a subsequent moderate exercise module.

Embodiment 160. The computing system according to any one of Embodiments 131-159, wherein moderate exercise is determined based on at least one of a heart rate (HR), a repetition maximum (RM), metabolic equivalents (METs), a maximal oxygen uptake capacity ($VO_{2max}$)/oxygen uptake reverse ($VO_2R$), or a rating of perceived exertion (RPE).

Embodiment 161. The computing system according to any one of Embodiments 131-160, wherein the first exercise module comprising aerobic exercise and/or acute exercise instructions is provided, and maintaining, optimizing, or strengthening an immune system of the subject comprises T cell boosting.

Embodiment 162. The computing system according to any one of Embodiments 131-161, wherein the first exercise module comprising aerobic exercise and/or acute exercise instructions is provided, and a level of the aerobic exercise and/or the acute exercise is determined prior to the providing.

Embodiment 163. The computing system according to any one of Embodiments 131-162, wherein the first exercise module comprising aerobic exercise and/or acute exercise instructions is provided, and a level of the aerobic exercise and/or the acute exercise is determined based on at least one of a HR, a RM, METs, a $VO_{2max}$/$VO_2R$, or a RPE.

Embodiment 164. The computing system according to any one of Embodiment 131-163, wherein the first exercise module comprising aerobic exercise instructions is provided, and maintaining, optimizing, or strengthening an immune system of the subject comprises emerging CD4+ T cells to activate the immune system.

Embodiment 165. The computing system according to any one of Embodiments 131-164, wherein the first exercise module comprising acute exercise instructions is provided, and maintaining, optimizing, or strengthening an immune system of the subject comprises removing pre-existing T cells to secure T cells zone for new T cells.

Embodiment 166. The computing system according to any one of Embodiments 131-165, wherein the first exercise module comprises at least one first exercise instructions for simultaneous aerobic and acute exercise.

Embodiment 167. The computing system according to any one of Embodiments 131-166, wherein said one or more first instructions comprise instructions for resistance exercise, concurrent exercise, and/or benchmark exercise.

Embodiment 168. The computing system according to Embodiment 167, wherein the benchmark exercise comprises one or more selected from the group consisting of jumping jacks, squats, and pushups.

Embodiment 169. The computing system according to Embodiment 167 or 168, further comprising repeating the benchmark exercise at least one times in succession.

Embodiment 170. The computing system according to any one of Embodiments 131-169, wherein said one or more first instructions comprise one or more instructions for walking, biking, aerobic dance and/or swimming.

Embodiment 171. The computing system according to any one of Embodiments 131-170, wherein the first vagal nerve stimulation module is provided, and the vagal nerve stimulation module comprises one or more first instructions to stimulate a sympathetic nervous system of the subject.

Embodiment 172. The computing system according to Embodiment 171, wherein maintaining, optimizing, or strengthening an immune system of the subject comprises accelerating maturation of B-cells and/or differentiation of B cells to plasma cells.

Embodiment 173. The computing system according to Embodiment 171 or 172, wherein maintaining, optimizing, or strengthening an immune system of the subject comprises increasing a number responsive cells of the subject's immune system.

Embodiment 174. The computing system according to any one of Embodiments 131-173, wherein the first vagal nerve stimulation module is provided, and the vagal nerve stimulation module comprises at least one instructions selected from the group consisting of sense stimulation instructions for sight, sound, touch, taste, and smell.

Embodiment 175. The computing system according to Embodiment 174, wherein the vagal nerve stimulation module comprises one or more sense stimulation instructions for sight, and the one or more sense stimulation instructions for sight include one or more instructions to view one or more figures to stimulate autonomic nervous system.

Embodiment 176. The computing system according to Embodiment 175, wherein the electronic device receives and displays the figures.

Embodiment 177. The computing system according to Embodiment 174 or 175, wherein the figures comprise one or more images for inducing fear in the subject.

Embodiment 178. The computing system according to any one of Embodiments 174-177, wherein the vagal nerve stimulation module comprises one or more sense stimulation instructions for sound, and the one or more sense stimulation instructions for sound include one or more instructions to hear one or more sounds to cause horror or relaxation.

Embodiment 179. The computing system according to Embodiment 178, wherein the one or more sounds to cause relaxation comprise white noise.

Embodiment 180. The computing system according to Embodiment 178 or 179, wherein the electronic device receives and plays the sounds.

Embodiment 181. The computing system according to any one of Embodiments 174-180, wherein the vagal nerve stimulation module comprises one or more sense stimulation instructions for touch, and the one or more sense stimulation instructions for touch include one or more instructions for abdominal breathing, controlling rate of breathing, holding breath, cold massage, bathing face in cold water, coughing, and skin massage.

Embodiment 182. The computing system according to any one of Embodiments 174-181, wherein the vagal nerve stimulation module comprises one or more sense stimulation instructions for touch, and the one or more sense stimulation instructions for touch include one or more instructions for controlling rate of breathing.

Embodiment 183. The computing system according to any one of Embodiments 174-182, wherein the vagal nerve stimulation module comprises one or more sense stimulation instructions for smell, and the one or more sense stimulation instructions for smell include one or more instructions to relax.

Embodiment 184. The computing system according to any one of Embodiments 131-183, wherein the electronic device is configured to release a scent for aroma therapy.

Embodiment 185. The computing system according to any one of Embodiments 131-184, wherein the subject is less than or equal to about 45 years old.

Embodiment 186. The computing system according to Embodiment 185, wherein the first exercise module is provided prior to the first vagal nerve stimulation module.

Embodiment 187. The computing system according to any one of Embodiments 131-186, wherein the sensor comprises one or more of: a camera, an accelerometer, a magnetometer, a light sensor, a microphone, a proximity sensor, a touch sensor, a gyroscope, a Global Positioning System (GPS) sensor, an ambient light sensor, a fingerprint sensor, a pedometer, a heart rate sensor, a motion sensor, and a thermometer.

Embodiment 188. The computing system according to any one of Embodiments 131-187, wherein the sensor comprises a touch sensor, and wherein the subject provides the adherence information to the electronic device using the touch sensor.

Embodiment 189. The computing system according to any one of Embodiments 131-188, wherein the sensor comprises a motion sensor or an accelerometer, and wherein the device detects the adherence information using the motion sensor or the accelerometer.

Embodiment 190. The computing system according to any one of Embodiments 131-189, wherein the electronic device is selected from the group consisting of a smart phone, a smart watch, smart jewelry, and a head mounted display.

Embodiment 191. The computing system according to any one of Embodiments 131-190, further comprising repeating a method using the computing system 2 times per week, 3 times per week, or more than 3 times per week.

Embodiment 192. A non-transitory computer readable medium having stored thereon software instructions for maintaining, optimizing, or strengthening an immune system of a subject in need thereof that, when executed by a processor, cause the processor to: display, by an electronic device to the subject, a first exercise module and/or a first vagal nerve stimulation module, each of the first modules comprising instructions for the subject to follow; sense, by a sensor in the electronic device, adherence by the subject to the instructions of the first modules; transmit, by the electronic device, adherence information, based on the adherence, to a server; receive, from the server, one or more second instructions based on the adherence information; and display, to the subject, a second exercise module and/or a second vagal nerve stimulation module, the second modules comprising the one or more second instructions.

Embodiment 193. The non-transitory computer readable medium according to Embodiment 192, wherein said maintaining, optimizing, or strengthening the immune system activates or increases production of natural killer (NK) cells in the subject.

Embodiment 194. The non-transitory computer readable medium according to Embodiment 192 or 193, wherein maintaining, optimizing, or strengthening the immune system reduces a change in a number of central T cells in the subject.

Embodiment 195. The non-transitory computer readable medium according to any one of Embodiments 192-194, wherein maintaining, optimizing, or strengthening the immune system reduces a change in a number of effector T cells in the subject.

Embodiment 196. The non-transitory computer readable medium according to any one of Embodiments 192-195, wherein maintaining, optimizing, or strengthening the immune system reduces a change in a number of effector memory T cells in the subject.

Embodiment 197. The non-transitory computer readable medium according to any one of Embodiments 192-196, wherein maintaining, optimizing, or strengthening the immune system activates or increases production of naïve CD4 T cells in the subject.

Embodiment 198. The non-transitory computer readable medium according to Embodiment 197, wherein the naïve T cells are activated or increased within one month from the providing.

Embodiment 199. The non-transitory computer readable medium according to any one of Embodiments 192-198, wherein maintaining, optimizing, or strengthening the immune system reduces a change in a number of central CD4 T cells in the subject.

Embodiment 200. The non-transitory computer readable medium according to any one of Embodiments 192-199, wherein maintaining, optimizing, or strengthening the immune system reduces a change in a number of effector CD4 T cells in the subject.

Embodiment 201. The non-transitory computer readable medium according to any one of Embodiments 192-200, wherein maintaining, optimizing, or strengthening the immune system reduces a change in a number of effector memory CD4 T cells in the subject.

Embodiment 202. The non-transitory computer readable medium according to any one of Embodiments 192-201, wherein maintaining, optimizing, or strengthening the immune system reduces a change in a number of naive CD8 T cells in the subject.

Embodiment 203. The non-transitory computer readable medium according to any one of Embodiments 192-202, wherein maintaining, optimizing, or strengthening the immune system reduces a change in a number of central CD8 T cells in the subject.

Embodiment 204. The non-transitory computer readable medium according to any one of Embodiments 192-203, wherein maintaining, optimizing, or strengthening the immune system reduces a change in a number of effector CD8 T cells in the subject.

Embodiment 205. The non-transitory computer readable medium according to any one of Embodiments 192-204, wherein maintaining, optimizing, or strengthening the immune system reduces a change in a number of effector memory CD8 T cells in the subject.

Embodiment 206. The non-transitory computer readable medium according to any one of Embodiments 192-205, wherein maintaining, optimizing, or strengthening the immune system activates or increases production of CD4 Treg cells in the subject.

Embodiment 207. The non-transitory computer readable medium according to any one of Embodiments 192-206, wherein maintaining, optimizing, or strengthening the immune system activates naïve B cells into maturation in the subject.

Embodiment 208. The non-transitory computer readable medium according to any one of Embodiments 192-207, wherein maintaining, optimizing, or strengthening the immune system increases naïve B cells in the subject.

Embodiment 209. The non-transitory computer readable medium according to any one of Embodiments 192-208, wherein maintaining, optimizing, or strengthening the immune system increases memory B cells in the subject.

Embodiment 210. The non-transitory computer readable medium according to any one of Embodiments 192-209, wherein maintaining, optimizing, or strengthening the immune system decreases plasma B cells in the subject.

Embodiment 211. The non-transitory computer readable medium of Embodiment 210, wherein the processor further generates digital therapeutic modules comprising the first exercise module and/or the first vagal nerve stimulation module for maintaining, optimizing, or strengthening an immune system based on age and/or target heart rate.

Embodiment 212. The non-transitory computer readable medium according to Embodiment 210 or 211, wherein the first exercise module and the first vagal nerve stimulation module are provided with a lag time of at least 3 hours.

Embodiment 213. The non-transitory computer readable medium according to any one of Embodiments 192-212, wherein the first exercise module is provided, and the exercise module comprises one or more first instructions to stimulate a parasympathetic nervous system of the subject.

Embodiment 214. The non-transitory computer readable medium according to any one of Embodiments 192-213, wherein the first exercise module is provided, and the first exercise module comprises at least one of moderate, aerobic and acute exercise instructions.

Embodiment 215. The non-transitory computer readable medium according to Embodiment 214, wherein the first exercise module comprising moderate exercise instructions is provided, and maintaining, optimizing, or strengthening an immune system of the subject comprises stimulating NK cells.

Embodiment 216. The non-transitory computer readable medium according to any one of Embodiments 192-215, wherein moderate exercise is determined based on at least age and/or target heart rate.

Embodiment 217. The non-transitory computer readable medium according to Embodiment 216, wherein moderate exercise for an about 15 year old subject comprises a target heart rate of between about 126 and about 150 beats per minute (bpm), moderate exercise for an about 20 year old subject comprises a target heart rate of between about 124 and about 147 bpm, moderate exercise for an about 25 year old subject comprises a target heart rate of between about 122 and about 145 bpm, moderate exercise for an about 30 year old subject comprises a target heart rate of between about 120 and about 142 bpm, moderate exercise for an about 35 year old subject comprises a target heart rate of between about 117 and about 139 bpm, moderate exercise for an about 40 year old subject comprises a target heart rate of between about 115 and about 137 bpm, moderate exercise for an about 45 year old subject comprises a target heart rate of between about 113 and about 134 bpm, moderate exercise for an about 50 year old subject comprises a target heart rate of between about 111 and about 132 bpm, moderate exercise for an about 55 year old subject comprises a target heart rate of between about 109 and about 129 bpm, moderate exercise for an about 60 year old subject comprises a target heart rate of between about 107 and about 127 bpm, moderate exercise for an about 65 year old subject comprises a target heart rate of between about 105 and about 124 bpm, moderate exercise for an about 70 year old subject comprises a target heart rate of between about 102 and about 122 bpm, moderate exercise for an about 75 year old subject comprises a target heart rate of between about 100 and about 119 bpm, moderate exercise for an about 80 year old subject comprises a target heart rate of between about 98 and about 117 bpm, moderate exercise for an about 85 year old subject comprises a target heart rate of between about 96 and about 114, and moderate exercise for an about 95 year old subject comprises a target heart rate of between about 92 and about 109.

Embodiment 218. The non-transitory computer readable medium according to Embodiment 126 or 127, wherein the target heart rate is determined, at least in part, based on feedback from exercise performed prior to the providing.

Embodiment 219. The non-transitory computer readable medium according to Embodiment 218, wherein an increase in the subject's heart rate by greater than 1 bpm, greater than 2 bpm, greater than 3 bpm, greater than 4 bpm, greater than 5 bpm, greater than 6 bpm, greater than 7 bpm, greater than 8 bpm, greater than 9 bpm, greater than 10 bpm, greater than 15 bpm, or greater than 20 bpm relative to the target heart rate for the moderate exercise module results in a decrease in the target heart rate for a subsequent moderate exercise module.

Embodiment 220. The non-transitory computer readable medium according to Embodiment 218, wherein a decrease in the subject's heart rate by greater than 1 bpm, greater than 2 bpm, greater than 3 bpm, greater than 4 bpm, greater than 5 bpm, greater than 6 bpm, greater than 7 bpm, greater than 8 bpm, greater than 9 bpm, greater than 10 bpm, greater than 15 bpm, or greater than 20 bpm relative to the target heart rate for the moderate exercise module results in an increase in the target heart rate for a subsequent moderate exercise module.

Embodiment 221. The non-transitory computer readable medium according to any one of Embodiments 192-220, wherein moderate exercise is determined based on at least one of a heart rate (HR), a repetition maximum (RM), metabolic equivalents (METs), a maximal oxygen uptake capacity ($VO_{2max}$)/oxygen uptake reverse ($VO_2R$), or a rating of perceived exertion (RPE).

Embodiment 222. The non-transitory computer readable medium according to Embodiment 221, wherein the first exercise module comprising aerobic exercise and/or acute exercise instructions is provided, and maintaining, optimizing, or strengthening an immune system of the subject comprises T cell boosting.

Embodiment 223. The non-transitory computer readable medium according to any one of Embodiments 192-222, wherein the first exercise module comprising aerobic exercise and/or acute exercise instructions is provided, and a level of the aerobic exercise and/or the acute exercise is determined prior to the providing.

Embodiment 224. The non-transitory computer readable medium according to any one of Embodiments 192-223, wherein the first exercise module comprising aerobic exercise and/or acute exercise instructions is provided, and a level of the aerobic exercise and/or the acute exercise is determined based on at least one of a HR, a RM, METs, a $VO_{2max}$/$VO_2R$, or a RPE.

Embodiment 225. The non-transitory computer readable medium according to Embodiment 224, wherein the first exercise module comprising aerobic exercise instructions is provided, and maintaining, optimizing, or strengthening an immune system of the subject comprises emerging CD4+ T cells to activate the immune system.

Embodiment 226. The non-transitory computer readable medium according to any one of Embodiments 192-225, wherein the first exercise module comprising acute exercise instructions is provided, and maintaining, optimizing, or strengthening an immune system of the subject comprises removing pre-existing T cells to secure T cells zone for new T cells.

Embodiment 227. The non-transitory computer readable medium according to any one of Embodiments 192-226, wherein the first exercise module comprises at least one first exercise instructions for simultaneous aerobic and acute exercise.

Embodiment 228. The non-transitory computer readable medium according to any one of Embodiments 192-227, wherein said one or more first instructions comprise instructions for resistance exercise, concurrent exercise, and/or benchmark exercise.

Embodiment 229. The non-transitory computer readable medium according to Embodiment 228, wherein the benchmark exercise comprises one or more selected from the group consisting of jumping jacks, squats, and pushups.

Embodiment 230. The non-transitory computer readable medium according to Embodiment 228 or 229, further comprising repeating the benchmark exercise at least one times in succession.

Embodiment 231. The non-transitory computer readable medium according to any one of Embodiments 192-230, wherein said one or more first instructions comprise one or more instructions for walking, biking, aerobic dance and/or swimming.

Embodiment 232. The non-transitory computer readable medium according to any one of Embodiments 192-231, wherein the first vagal nerve stimulation module is provided, and the vagal nerve stimulation module comprises one or more first instructions to stimulate a sympathetic nervous system of the subject.

Embodiment 233. The non-transitory computer readable medium according to Embodiment 232, wherein maintaining, optimizing, or strengthening an immune system of the subject comprises accelerating maturation of B-cells and/or differentiation of B cells to plasma cells.

Embodiment 234. The non-transitory computer readable medium according to Embodiment 232 or 233, wherein maintaining, optimizing, or strengthening an immune system of the subject comprises increasing a number responsive cells of the subject's immune system.

Embodiment 235. The non-transitory computer readable medium according to any one of Embodiments 192-234, wherein the first vagal nerve stimulation module is provided, and the vagal nerve stimulation module comprises at least one instructions selected from the group consisting of sense stimulation instructions for sight, sound, touch, taste, and smell.

Embodiment 236. The non-transitory computer readable medium according to Embodiment 235, wherein the vagal nerve stimulation module comprises one or more sense stimulation instructions for sight, and the one or more sense stimulation instructions for sight include one or more instructions to view one or more figures to stimulate autonomic nervous system.

Embodiment 237. The non-transitory computer readable medium according to Embodiment 236, wherein the electronic device receives and displays the figures.

Embodiment 238. The non-transitory computer readable medium according to Embodiment 236 or 237, wherein the figures comprise one or more images for inducing fear in the subject.

Embodiment 239. The non-transitory computer readable medium according to any one of Embodiments 192-238, wherein the vagal nerve stimulation module comprises one or more sense stimulation instructions for sound, and the one or more sense stimulation instructions for sound include one or more instructions to hear one or more sounds to cause horror or relaxation.

Embodiment 240. The non-transitory computer readable medium according to Embodiment 239, wherein the one or more sounds to cause relaxation comprise white noise.

Embodiment 241. The non-transitory computer readable medium according to Embodiment 239 or 240, wherein the electronic device receives and plays the sounds.

Embodiment 242. The non-transitory computer readable medium according to any one of Embodiments 192-241, wherein the vagal nerve stimulation module comprises one or more sense stimulation instructions for touch, and the one or more sense stimulation instructions for touch include one or more instructions for abdominal breathing, controlling rate of breathing, holding breath, cold massage, bathing face in cold water, coughing, and skin massage.

Embodiment 243. The non-transitory computer readable medium according to any one of Embodiments 192-242, wherein the vagal nerve stimulation module comprises one or more sense stimulation instructions for touch, and the one or more sense stimulation instructions for touch include one or more instructions for controlling rate of breathing.

Embodiment 244. The non-transitory computer readable medium according to any one of Embodiments 192-243, wherein the vagal nerve stimulation module comprises one or more sense stimulation instructions for smell, and the one or more sense stimulation instructions for smell include one or more instructions to relax.

Embodiment 245. The non-transitory computer readable medium according to any one of Embodiments 192-244, wherein the electronic device is configured to release a scent for aroma therapy.

Embodiment 246. The non-transitory computer readable medium according to any one of Embodiments 192-245, wherein the subject is less than or equal to about 45 years old.

Embodiment 247. The non-transitory computer readable medium according to Embodiment 246, wherein the first exercise module is provided prior to the first vagal nerve stimulation module.

Embodiment 248. The non-transitory computer readable medium according to any one of Embodiments 192-247, wherein the server receives the one or more second instructions from an external reviewer.

Embodiment 249. The non-transitory computer readable medium according to Embodiment 248, wherein the external reviewer comprises a health professional.

Embodiment 250. The non-transitory computer readable medium according to Embodiment 249, wherein the external reviewer comprises an artificial intelligence (AI).

Embodiment 251. The non-transitory computer readable medium according to any one of Embodiments 192-250, wherein the sensor comprises one or more of: a camera, an accelerometer, a magnetometer, a light sensor, a microphone, a proximity sensor, a touch sensor, a gyroscope, a Global Positioning System (GPS) sensor, an ambient light sensor, a fingerprint sensor, a pedometer, a heart rate sensor, a motion sensor, and a thermometer.

Embodiment 252. The non-transitory computer readable medium according to any one of Embodiments 192-251, wherein the sensor comprises a touch sensor, and wherein the subject provides the adherence information to the electronic device using the touch sensor.

Embodiment 253. The non-transitory computer readable medium according to any one of Embodiments 192-252, wherein the sensor comprises a motion sensor or an accelerometer, and wherein the device detects the adherence information using the motion sensor or the accelerometer.

Embodiment 254. The non-transitory computer readable medium according to any one of Embodiments 192-253, wherein the electronic device is selected from the group consisting of a smart phone, a smart watch, smart jewelry, and a head mounted display.

Embodiment 255. The non-transitory computer readable medium according to any one of Embodiments 192-254, further comprising repeating a method using the non-transitory computer readable medium 2 times per week, 3 times per week, or more than 3 times per week.

What is claimed is:

1. A method of treating a virus disease in a subject in need thereof, the method comprising:
   providing a first exercise module and a first vagal nerve stimulation module, the first exercise module comprising at least one first exercise instruction selected from the group consisting of moderate, aerobic and acute exercise instructions for the subject to follow, and the first vagal nerve stimulation module comprising at least one first stimulation instruction selected from the group consisting of a sense stimulation instruction for sight, a sense stimulation instruction for sound, a sense stimulation instruction for touch, a sense stimulation instruction for taste and a sense stimulation instruction for smell for the subject to follow, thereby stimulating at least one of sympathetic nerve system and autonomic nervous system of the subject,
   detecting the subject's adherence to the at least one first exercise instruction and the at least one first stimulation instruction using a sensor, and
   providing a second exercise module and a second vagal nerve stimulation module based on the adherence information, the second exercise module comprising at least one second exercise instruction selected from the group consisting of moderate, aerobic and acute exercise instructions, and the second vagal nerve stimulation module comprising at least one second stimulation instruction selected from the group consisting of a sense stimulation instruction for sight, a sense stimulation instruction for sound, a sense stimulation instruction for touch, a sense stimulation instruction for taste and a sense stimulation instruction for smell for the subject to follow, thereby stimulating at least one of sympathetic nerve system and autonomic nervous system of the subject.

2. The method according to claim 1, wherein the method activates or increases production of natural killer (NK) cells in the subject.

3. The method according to claim 1, wherein the method reduces a change in a number of central T cells in the subject.

4. The method according to claim 1, wherein the at least one first stimulation instruction stimulates the autonomic nervous system.

5. The method according to claim 1, wherein the virus disease includes at least one of SARS, MERS, COVID-19, influenza, respiratory tract infection, or gastrointestinal infection.

6. The method according to claim 1, wherein the first exercise module and the first vagal nerve stimulation module are provided with a first lag time therebetween.

7. The method according to claim 6, wherein the first lag time is at least 3 hours.

8. The method according to claim 1, wherein the second exercise module and the second vagal nerve stimulation module are provided with a second lag time therebetween.

9. The method according to claim 8, wherein the second lag time is at least 3 hours.

10. The method according to claim 1, wherein the first exercise module is configured to provide a first moderate exercise instruction corresponding to a target heart rate, the target heart rate predetermined based on an age of the subject.

11. The method according to claim 10, comprising:
measuring an optical blood flow of the subject to measure a heart rate; and
adjusting the target heart rate based on the measured heart rate and the age of the subject.

12. The method according to claim 11, wherein the second exercise module and the second vagal nerve stimulation model is provided based on the adjusted target heart rate.

13. The method according to claim 12, wherein the at least one first exercise instruction comprises instructions for benchmark exercise, the benchmark exercise comprises one or more exercises selected from the group consisting of jumping jacks, squats, and pushups.

14. A digital system for treating a virus disease of a subject, the digital system comprising:
a processor configured to:
provide a first exercise module and a first vagal nerve stimulation module, the first exercise module comprising at least one first exercise instruction selected from the group consisting of moderate, aerobic, and acute exercise instructions for the subject to follow, and the first vagal nerve stimulation module comprising at least one first stimulation instruction selected from the group consisting of a sense stimulation instruction for sight, a sense stimulation instruction for sound, a sense stimulation instruction for touch, a sense stimulation instruction for taste and a sense stimulation instruction for smell for the subject to follow, thereby stimulating at least one of sympathetic nerve system and autonomic nervous system of the subject,
detect the subject's adherence to the at least one first exercise instruction and the at least one first stimulation instruction using a sensor, and
provide a second exercise module and a second vagal nerve stimulation module based on the adherence information, the second exercise module comprising at least one second exercise instruction selected from the group consisting of moderate, aerobic, and acute exercise instructions, and the second vagal nerve stimulation module comprising at least one second stimulation instruction selected from the group consisting of a sense stimulation instruction for sight, a sense stimulation instruction for sound, a sense stimulation instruction for touch, a sense stimulation instruction for taste and a sense stimulation instruction for smell for the subject to follow, thereby stimulating at least one of sympathetic nerve system and autonomic nervous system of the subject.

15. The digital system according to claim 14, wherein the first exercise module and the second exercise module activate or increase production of natural killer (NK) cells in the subject.

16. The digital system according to claim 14, wherein the first exercise module and the second exercise module reduce a change in a number of central T cells in the subject.

17. The digital system according to claim 14, wherein the at least one first stimulation instruction stimulates the autonomic nervous system.

18. The digital system according to claim 14, wherein the virus disease includes at least one of SARS, MERS, COVID-19, influenza, respiratory tract infection, or gastrointestinal infection.

19. A non-transitory computer readable medium storage configured to store one or more programs which, when executed by a processor, cause the processor to perform operations comprising:
providing a first exercise module and a first vagal nerve stimulation module, the first exercise module comprising at least one first exercise instruction selected from the group consisting of moderate, aerobic, or acute exercise instructions for the subject to follow, and the first vagal nerve stimulation module comprising at least one first stimulation instructions selected from the group consisting of a sense stimulation instruction for sight, a sense stimulation instruction for sound, a sense stimulation instruction for touch, a sense stimulation instruction for taste and a sense stimulation instruction for smell for the subject to follow, thereby stimulating at least one of sympathetic nerve system and autonomic nervous system of the subject,
detecting the subject's adherence to the at least one first exercise instruction and the at least one first stimulation instruction using a sensor, and
providing a second exercise module and a second vagal nerve stimulation module based on the adherence information, the second exercise module comprising at least one second exercise instruction selected from the group consisting of moderate, aerobic and acute exercise instructions, and the second vagal nerve stimulation module comprising at least one second stimulation instructions selected from the group consisting of a sense stimulation instruction for sight, a sense stimulation instruction for sound, a sense stimulation instruction for touch, a sense stimulation instruction for taste and a sense stimulation instruction for smell for the subject to follow, thereby stimulating at least one of sympathetic nerve system and autonomic nervous system of the subject.

20. The non-transitory computer readable medium storage according to claim 19, wherein the first exercise module and the second exercise module activate or increase production of natural killer (NK) cells in the subject.

21. The non-transitory computer readable medium storage according to claim 19, wherein the first exercise module and the second exercise module reduce a change in a number of central T cells in the subject.

* * * * *